US008685735B2

(12) United States Patent
McCarthy et al.

(10) Patent No.: US 8,685,735 B2
(45) Date of Patent: Apr. 1, 2014

(54) GENES FOR MODULATING COFFEE MATURATION AND METHODS FOR THEIR USE

(75) Inventors: James Gerard McCarthy, Noizay (FR); Jerome Spiral, Tours (FR); Victoria Caillet, Monnaie (FR)

(73) Assignee: Nestec S.A., Vevey (CH)

( * ) Notice: Subject to any disclaimer, the term of this patent is extended or adjusted under 35 U.S.C. 154(b) by 286 days.

(21) Appl. No.: 13/000,663

(22) PCT Filed: Jun. 23, 2009

(86) PCT No.: PCT/EP2009/057756
§ 371 (c)(1),
(2), (4) Date: Dec. 22, 2010

(87) PCT Pub. No.: WO2009/156371
PCT Pub. Date: Dec. 30, 2009

(65) Prior Publication Data
US 2011/0263023 A1    Oct. 27, 2011

(30) Foreign Application Priority Data
Jun. 23, 2008 (EP) .................................. 08158808

(51) Int. Cl.
C12N 15/82    (2006.01)
C12N 15/70    (2006.01)

(52) U.S. Cl.
USPC ..................... 435/419; 435/320.1; 435/252.3

(58) Field of Classification Search
USPC ........................................................ 800/290
See application file for complete search history.

(56) References Cited

U.S. PATENT DOCUMENTS 5,874,269 A * 2/1999 Stiles et al. .................... 435/189
6,617,433 B1    9/2003 Marraccini et al.
7,153,953 B2    12/2006 Marraccini et al.

FOREIGN PATENT DOCUMENTS

| EP | 1172441 | 1/2002 |
|----|---------|--------|
| KR | 10-2002-0078495 | * 6/2002 |
| WO | 0078983 | 12/2000 |
| WO | 2005063997 | 7/2005 |
| WO | 2006053169 | 5/2006 |
| WO | 2007005928 | 1/2007 |
| WO | 2007005980 | 1/2007 |
| WO | 2007022318 | 2/2007 |
| WO | 2008043268 | 4/2008 |
| WO | WO 2008070179 | * 6/2008 |

OTHER PUBLICATIONS

Banzai et al., molecular cloning and characterization of genes encoding BURP domain-containing protein in the mangrove, *Bruguiera gymnorrhiza*, 16 Trees, 87-93 (2002).*
Abe et al. (*Arabidopsis* AtMYC2 (bHLH) and AtMYB2 (MYB) function as transcriptional activators in abscisic acid signaling, 15 Plant Cell, 63-78 (2003)).*

(Continued)

*Primary Examiner* — Cynthia Collins
*Assistant Examiner* — Rebecca Coobs
(74) *Attorney, Agent, or Firm* — K&L Gates LLP

(57) ABSTRACT

Disclosed are isolated nucleic acids for modulating coffee maturation. Also disclosed are promoters derived from such genes. Methods for using the nucleic acids for improving quality attributes of coffee are provided. Also provided are methods for assessing the quality of plant-based agricultural products, such as coffee.

7 Claims, 31 Drawing Sheets

(56) References Cited

OTHER PUBLICATIONS

GenBank Accession No. DV712970.1 [online], [retrieved on Jan. 9, 2012], retrieved from the internet <http://www.ncbi.nlm.nih.gov/nucest/82506279>.*
Machine translation of Bae et al., Korean Patent Application No. 2002-78495 published Jun. 16, 2004.*
Friedberg, Automated protein function prediction—the genomic challenge, 7 Briefings in Bioinformatics, 225-242 (2006).*
Lin C et al: (2005), "Coffee and tomato share common gene repertoires as revealed by deep sequencing of seed and cherry transcripts," TAG Theoretical and Applied Genetics, 112(1), 114-130. XP002502102.
Poncet V et al: (2006), "SSR mining in coffee tree EST databases: potential use of EST—SSRs as markers for the Coffea genus," Molecular Genetics and Genomics, 276(5), 436-449. XP002675359.
Lin C et al: (2005), "Coffee and tomato share common gene repertoires as revealed by deep sequencing of seed and cherry transcripts," TAG Theoretical and Applied Genetics, 112(1), 114-130. XP002675360.
Romero G et al: (2010), "Partial resistance to leaf rust (*Hemileia vastatrix*) in coffee (*Coffea arabica* L.): genetic analysis and molecular characterization of putative candidate genes," Molecular Breeding, 25(4), 685-697. XP002675361.
Hanselle T et al: (2001), "Biochemical and molecular biological studies on infection (*Ascochyta rabiei*)-induced thaumatin-like proteins from chickpea plants (*Cicer arietinum* L.)," Zeitschrift Fur Naturforschung C, 56 (11/12), 1095-1107. XP002675362.
Santén K: (2007), "Pathogenesis-related proteins in barley," vol. 2007, No. 86. XP055026244.
Lin et al., "Coffee and tomato share common gene repertoires as revealed by deep sequencing of seed and cherry transcripts," Theoretical and Applied Genetics; International Journal of Plant Breeding Research, vol. 112, No. 1, pp. 114-130, Dec. 1, 2005—XP019322122.
Mueller, et al., Seed of Late Development Stage *Coffea canephora* cDNA clone cccs46w20f16 5' mRNA sequence, Nov. 17, 2005—Abstract, 2 pages—XP002502102.
Banzai et al., "Molecular cloning and characterization of genes encoding BURP domain-containing protein in the mangrove, *Bruguiera gymnorrhiza*," Trees, vol. 16, Jan. 1, 2002, pp. 87-93—XP002259318.
Luo et al., "Functional characterization of a cotton late embryogenesis-abundant D113 gene promoter in transgenic tobacco," Plant Cell Reports, vol. 27, No. 4, Apr. 2008, pp. 707-717—XP019587762.
De Nardi et al., "Differential responses of *Ceffea arabica* L. leaves and roots to chemically induced systemic acquired resistance," Geneome, vol. 49, (2006), pp. 1594-1605—XP002512496.
Mueller, et al., Seed of Late Development Stage *Coffea canephora* cDNA clone cccs46w20f16 5' mRNA sequence, Nov. 17, 2005—Abstract, 2 pages—XP002512497.
Romero et al., "Partial resistance to *Hemileia vastatrix* leaf rust in coffee: genetic analysis and molecular characterization of putative candidate genes," Nov. 1, 2007—Abstract, 2 pages—XP002512498.
De Nardi, et al., "Differential responses of *Coffea arabica* L. leaves and roots to chemical induced systemic acquired resistance," Genome, vol. 49, No. 12, pp. 1594-1605 (2006)—Abstract, 1 page—XP002512499.
Yu, et al., "Isolation and characterization of a BURP domain-containing gene BnBDC1 from *Brassica napus* involved in abiotic and biotic stress," Physiologia Plantarum, vol. 122, pp. 210-218 (2004)—XP002502099.
International Search Report, PCT/EP2009/057756 dated Sep. 9, 2009, 8 pages.

* cited by examiner

DIP1

DIP2

PR-5A

A

*GTTTCATTTTTCACATCTATCATAAAATTTCACTTCTGTTTACACTTCCCTTGGCGGCCAGTCTCTTACAAA*ATGGAGTT
TCGACCCGTACATCTCTTCATCTTTGTTGCTCTAGCTTGTGTGTCAAGCCACGCAGCACAACCTGCTGAGACATATTGGA
AATCTGTGCTCCCTAACAGTCCTATGCCGAAAGCTATCGAGGATCTTATACAATCTGAAACGGTGGATGATAAAAGTACT
TCAGTCGGAGTAAGTGGTGGTGGAGTAGATGTTAATACTCAGGGTGGAAATCCAGGAGGCACCAACGTGAATGCTGGGCA
CGGTGGCGTAGATGTAAATACACCAGGAGGCACCAATGTAAACGTCGGGCCTGGTGGAGTAGGTGTTAATACACCAGGAG
GCACCAACGTGAATGTTGGACCGGGGGATCCAGGAGGTTCCGAGACACAGGGCAGAAATCCTGAAGGCACCAATGTGAAT
GTCGGGCATGGTGGAGGTGTAACCGCATCCTCAGGCCACCACAGGGGGAAACCAGTATATGTGGGAGGAAGGCCAGGGAC
ATCACCATTCTTGTATAACTACGCAGCAACCAGGGATCAGCTCCATGACAACCCAAATGTAGCTCTTTTCTTCTTGGAAA
ATAACATGACTCGAGGATCAAAGATGAACTTGCATTTCTTCAAGACTTCACATGGAGCCACTTTCTTACCTCGCCAGGTT
GCTGAATCAATTCCTTTCTCATCAAACAAAATGACTGAAATCTTGAACAAATTCTCAGTGAAGCCCAACTCACAGGAAGC
TGAAGTTATGAAAAATACAATAAAAGAGTGCGAGAAGCCAGGCATCCAGGGAGAGGAGAAGTTCTGTGCAACATCATTGG
AAGCAATGGTAGATTTCACCACCTCCAAACTGGGGAAGAACGTTCAGGCGATATCAACAAATTCAGAGAAAGATACTCCA
CTGCAGAAATATACCATTGCAGGAGTGAAAAACATGACAAATGACAAAGCTGTAGTGTGCCACCAGCAAAATTATGCATA
TGCTGTATTTTACTGCCACAAAACACAAGCTACTAGAGCATATACACTTTCCTTGGTGGGTGCAGATGGAACAAAAGTTA
AAGCAGTGGCAGTATGCCATGAAGATACAACAAAATGGAACCCAAAACACTTGGCTTTCAAAGTTCTGCAGATCAAGCCA
GGACAAGTTCCTGTTTGCCATTTCCTTCCCGAGGATCATGTTGTCTGGGTACCTAAATAAATATGTGCAGGAAACTCCAA
*ATGCTTGCCCATTTGGTTCTATTGTAAAACAATAATACACTGGTTGTAGTTCCACTAATAAACATATCCCTCTTAGTTAA
AAAAAAAAAAAAAAAAA*

B   Fwd 124952    CCCAAAACACTTGGCTTTCAA
    Rev 124952    GAAATGGCAAACAGGAACTTGTC
    Probe         TCTGCAGATCAAGCCA C   GW1 124952    TCGATAGCTTTCGGCATAGGACTGTTAGGG
    GW2 124952    TTCCAATATGTCTCAGCAGGTTGTGCTG

*CTGATTACCCTCACTAAAGGGAACAAAAGCTGGAGCTCCACCGCGGTGGCGGCCGCTCTAGAACTAGTGGATCCCCCGGG*
*CTGCAGGAATTCGGCACGAGGTTGCATACTAGCAGCCTACCGT*GGCTCGTGCGCATAAACTATTATGGAATTTCTGAAGC
TTCTCTACTTTCTCTCTTTTCTTTTTCTAGGAGTTGGGGCAAACCATGCAGATCTTGAAGCCTACTGGAAATCCGAGCTT
CCAAACACTCCTATGCCCAAAGCTGTTAGAGACCTGCTAAAAGATGGGAAGTGGCCGGAAAGGGGCAATTTCAGGTTGAA
AACATATGATGACAGCTGTAGTTTCAAACATTATTGTGGAAATCCTACTGAAGATGAGCTCCATATTGACCCAAAAGTGA
AAGTCTTTTTCTTGAAAATGGACCTCAATCGCGGCTCAAGCATGAATATGAAGTTTGTTGAATCAGTGAAAAGTCCTACG
GCTTTCCTGCCCCGCCAGGTTGCTAATTCGATTCCCTTCTCATCAAaTCTGTTCCTGaAATTTTGAACAAATACTCACT
GAATCCACAATCACAAGATGCTAGAATTATTAAGGAAACGATAGCAGAATGCGAGGTGCCCGCAATGAAAGGAGAAGACA
AGTATTGTGCGACTTCTCTCGAATCAATGGTTGATTTCACTACTTCAAAGCTGGGCAAAGATGTTCTAGCAATTTCTAAC
GAAGCACAGAAAACAGATCCAGAAGTCCAGAAATATGGTATTGTGTCTGTTTCCAAGTTGAACAACAACGATAAAGAAAT
AGTTTCTTGCCACAGGCAAAACTATTTCTACGCAGTTTTCTACTGCCACACCACACAGAATACAGATGCATATATGGTTA
ATTTAGTTGGTGCCGATGGAGCAAAAGTCAAAGCTGTAGCTGTTTGTCACCGGGATACGTCAGCATGGAACCCAAGGCAT
TTGGCTTTTCAGCTGCTGAAGGTGAAGCCAGGAACTGTTCCAATCTGCCATTTCCTTCCTGAGGATCACATTGTCTGGGT
TCCGAAGCACTAA*ATATAGTACAGAAACATGTTAACGCTTCCCAAGTGATCTATGTTCGTTGCTCTGATGGTTTTACGT*
*ATGTCTTCTGCAGCTTGGGAGTTCTATCCATTATGTTGCCATAATTAAATAAATCCATGTTTAGTTTGTTCTCTACTTTG*
*ATATCAAATTATATATGTCAATCTACTATTACAAAGATGTAACGTACCTGGTTTCATTTTAAAAAAAAAAAAAAAAAAAA*
*AAAAAAAAAAAAAAAAAAAAAAAAAAAAAA*

B    cccp21sg1-F1    GGCTCGTGCGCATAAACT
      cccp21sg1-R     TGGGCATAGGAGTGTTTGGAA
      cccp21sg1-MGB1  TTATGGAATTTCTGAAGCTT

CGACTTTCTCCATTCCTTAACCATGAAAACCTTCAATTCTTTCAGCATCTCCACTCTTCTCATCATTGCTTTCCTCTCAA
CCTCCGCCCATGCTGCCACTTTCGACATCCGAAACAATTGTCCCTACACAGTCTGGGCTGCAGCGGTACCTGGCGGTGGT
CGAAGGCTAGACCGAGGCCAAACATGGACCATCAACGTGGCAGCCGGCACAGCCGGAGCTCGTATCTGGGCTAGAACAAA
TTGTAACTTCGATGGAAACGGCCGTGGCAGCTGTCAGACCGGTGACTGCGGTGGAGTTCTTCAATGCACTGCCTACGGTA
GACCACCTAATACTCTAGCAGAATACGCACTGAACCAGTTCAATAACCTGGACTTCTTCGACATTTCCCTTGTTGATGGC
TTCAATGTGCCGATGGATTTCAGCCCTACATCCAATGGCTGCACCCGGGGCATCAGGTGCACCGCCGACATAAATGGGCA
GTGCCCAAGTGTGCTTAAAGCTCCAGGAGGTTGCAACAATCCATGCACTGTTTTCAAGACTGATCAGTATTGCTGCAACT
CAGGCAGCTGCAGTGCGACTGACTATTCCAGGTTCTTCAAGACTAGGTGCCCGGATGCATACAGCTATCCGAAAGATGAC
CAGACTAGCACATTCACTTGCCGAGGAGGAACCAACTATAGGGTTGTCTTTTGCCCATGAAAAGATCCTTAAAACAAAGA
CTTGCTTGAGACTAGTTAAATAGTTATACATGCATGGCACAATAATTTGCTGGACACAACACATAACGTCATCTGCAAAT
GCAATATTCAGTTCAAATAAAAACTATGAACTGATAATAAAGTTAATAGCTACTGGATGTTCGCGTTAAAAAAAAAAAAA
AAAAAAAA

B    Fwd 119511     GGTGCACCGCCGACATA
     Rev 119511     CAACCTCCTGGAGCTTTAAGCA
     Probe          TGGGCAGTGCCCAAG C    GW1 119511     CGAAGGCTAGACCGAGGCCAAACAT
     GW2 119511     TTTCGGATGTCGAAAGTGGCAGCATGG

FIG.6

DIP1 pAS22
5'    primer Dip1A F5

AAAGAACAATTTTCTATTTGCTGTTAGAAAAAATAATACCGGATTCATTCCTTACTTATTATCTACTAAAACGATGAGT
AATAAAAAGCGAAAACGTAAATGTTCATGACAAATACGGTTATATAATTGGATCTATCTTGAATTTATGCTAAAATAA
AAAAGTTATACCATAACAAGAAAACCGGGATTGGATATGCACCATAATTTCACAACGCCAAACAGTTTCCTTTCAAAC
TTGCAAGCAAGAAAAGTATGAAAATAGTTAATGGCTTTCTGTGTATAAAAATAGTAGTTAATAGGTATGCATAATACG
TTTATGTGATTTTTTTGACATTCTTCTGTGACTGAAAGATGATCATCCAAATCCTGTAGCTAAGCTTAGTAAAACTAGC
AAATCACTTTGGATATACTTCAAGTTT*gtcagccacatiaagagcagg*ATTGATGCCATACGTCAAAAACTTGAAAAAAAAAACTACTA
ACTAATCGATAAAGATGACACCAGATTGCCATAAGCGTAAGGCTTAAAACTTAAGCTCTCAACTTCCAGCTGAAACCCTTTGTCT
GATAGCATTGATCAAGTAAGGATTGACCATTATCAGATCAGACCAGACAGGATTCCCGTTTGCGTATGCAATTATGAAACAGGC
ATCTGTATCTCACACAGAAACGCGCAGAACTTCACACATGTAACTCACTGATACATTTGGCTCAATTGGCATTAATGCGTTTAAG
CCACAGTTGGAAGTGATTAGAGCACAAGTCATCAGTAGAGATGATCTGTTGCTTGTCTGCTGACATTTTACCCTGAACCCACAT
TCGGC*TATAAATA*GCACTATAGTTGTTGCCTTTTATCTTCAAGAAAGTTGTGGTTTCATTTTTCACATCTATCATAAAATTTCA
CTTCTGTTTACACTTCCCTTGGCAGCCAGTCTCTTACAAAATGGAGTTTCGACCCCTACATCTCTTCATCTTTGTTGCTgt
gagtacaacattgcatcaattatttacgctttgccaataaaatgtattctcttttacgcttttccaataaaatgttcacttgttcgtctgtgtgtttcagCTAGCTTGCGTGTCAAGCCAC
GCAGCACAACCTGCTGAGACATATTGGAAATCTGTGCTCCCTAACA*GTCCTATGCCGAAAGCTA*TCGAGGATCTTATA
CAATCTGgtcagactcaaacctaaaagctgttctttcactgttgttattcaaaaacaaaatgcttttttgtctcaatgcatttcatgttctacatgccagtaatgttctcgagaaaccacaaaattaggc
ttaggcaataaacagtgatacaaaggttaaaagggaacgagtcagcaaactctagaataaatactactacagagcataagacattaaattacctttttttagcaaaaaattggcaaatccggtacatga
aaaggaaagtagatttttaacagttcttacacaaggaaaactaatcctatctaaggaaagaaagaataagacattaaattacctataaggtggtaagaatagtatattcatccgtgtgttcatgctaactg
gttgttatggcagAAACGGTGGATGATAAAAGTACTTCAGTCGGAGTAAGTGGTGGTGGAGTAGATGTTAATGCTCAGGGTGG
AAATCCAGGAGGCACCAACGTGAATGCTGGGCACGGTGGCGTAGATGTAAATACACCAGGAGGCACCAATGTAAACG
TCGGGCCTGGTGGAGTAGGTGTTAATACACCAGGAGGCACCAACGTGAATGTTGGACCGGGGGATCCAGGAGGTTCC
GAGACACAGGGCAGAAATCCTGAAGGCACCGATGTGAATGTCGGGCATGGTGGAGGTGTAACCGTATCCTCAGGCCA
CCACAGGGGgAAACCAGTATATGTGGGAGTAAGGCCAGGGACATCACCATTCTTGTATAACTACGCAGCAACCAAGG
ATCAGCTCCATGACAACCCAAATGTAGCTCTTTTCTTCTTGGAAAATAACATGACTCGAGGATCAAAGATGAACTTGC
ATTTCTTCAAGACTTCACTTGGAGCCACTTTCTTACCTCGCCAGGTTGCTGAATCAATTCCTTTCTCATCAAACAAAAT
GACTGAAATCTTGAACAAATTCTCGGTGAAGCCCAACTCACAGGAAGCTGAAGTTATGAAAAATACAATAAAAGAGT
GCGAGAAGCCAGGCATCCAGGGAGAGGAGAAGTTCTGTGCAACATCATTGGAAGCAATGGTAGATTTCACCACCTCC
AAACTGGGGAAGAACGTTCAGGCGATATCAACAAATTCAGAGAAAGATACTCCACTGCAGAAATATACCATTGCAGG
AGTGAAAAACATGACAAATGACAAAGCTGTAGTGTGCCACCAGCAAAATTATGCATATGCTGTATTTTACTGCCACAA
AACACAAGCTACTAGAGCATATACACTTTCCTTGGTGGGTGCAGATGGAACAAAAGTTAAAGCAGTGGCAGTATGCC
ATGAAGATACAACAAAATGGAACCCAAAACACTTGGCTTTCAAAGTTCTGCAGATCAAGCCAGGACAAGTTCCTGTTT
GCCATTTCCTTCCTGAGGATCATGTTGTCTGGGTACCTAAATAA*ATATGTGCAG*gaaactccaaatgcttgccc*ATTTGGTTCTATTG*
TAAAACAATAATACACTGGTTGTAGTTCCACTAATAAACATATCCCTCTTAGTAAAAAAAAAAAAAAAAAAAA 3'

FIG. 10 pAS22

AAAGAACAATTTCTATTTGCTGTTAGAAAAAATAATACCGGATTCATTCCTTACTTATTATCTACTAAAACGATGAGTA
ATAAAAAGCGAAAACGTAAATGTTCATGACAAATACGGTTATATAATTGGATCTATCTTGAATTTATGCTAAAATAAAA
AAGTTATACCA TAACAAG AAAACCGGGATTGGATATGCACCATAATTTCACAACGCCAAACAGTTTCCTTTCAAACTTG
CAAGCAAGAAAAGTATGAAAATAGTTAATGGCTTTCTGTGTATAAAAATAGTAGTTAATAGGTATGCATAATACGTTTAT
GTGATTTTTTTGACATTCTTCTGTGACTGAAAGATGATCATCCAAATCCTGTAGCTAAGCTTAGTAAAACTAGCAAATCA
CTTTGGATATACTTCAAGTTTGTCAGCCACATTAAGAGCAGGATTGAAGCCATACGTCAAAAACTTGAAAAAAAAACTAC
TAACTAATCGATAAAGATGACGCCAGATTGCCATAAGCGCAAGGCTTAAAACTTGAGCTCTCAACTTCCAGCTGAAACC
CTTTGTCTGATAGCATTGATCAAGTAAGGATTGACCATTATCAGATCAGACCAGACAGGATTATCGTTTGCGTATGCAAT
TAGGAAACAGGCATCTGTATCTCACACACAAACGCGCAGAACTTCACACATGTAACTCACTGATACATTTGGCTCAAT
TGGCATTAATGCGTTTAAGCCACAGTTGGAAGTGATTAGAGCACAAGTCATCAGTAGAGATGATCTGTTGCTTATCTGC
TGACATTTTACCCTGAACCCACATTCGGCTATAAATAGCACTATAGTTGTTGCCTTTTATCTTCAAGAAAGTTGTG*GTTT*
*CATTTTTCACATCTATCATAAAATTTCACTTCTGTTTACACTTCCCTTGGCGGCCAGTCTCTTACAAA*ATGGAGTTTCGA
CCCCTACATCTCTTCATCTTTGTTGCTtgtgagtacaacattgcatcaattatttacgcttttgccaataaaatgtattct
cttttacgcttttccaataaaatgttcacttgttcgtctgtgtgtttcagCTAGCTTGCGTGTCAAGCCACGCAGCACA
ACCTgctgagacatattggaaatcTGTGCTCCCTAACAGTCCTATGCCGAAAGCTA

FIG. 11

PR-5-A
pAC17-A
5'    primer AP2 GW

```
ACTATAGGGCACGCGTGGTCGACGGCCCGGGCTGGTCTGGAGAGTTATAACATGGTGAAACAAATAAGAGAAT
ACATTTTACTGAAATATGATGTCTAGTTATAAAAGCACAACGCCAGAGAAGAAAAAATTCACTTATAAG
ATACTTCATATCCATTTCCTTTAGAATAATAATAATATTACTAATAATTATTACAAGAATAATACCGCTTT
TTATGTTGAGCTAAGCCCATTAGTTATGTAATTCATCATTTTCTCTATTCGTAGAATAAAATTTTGTGATAA
AACAAAATCTTTGCATCTATAATGCACGGCAAAATCAGCCCTTCAAAAAGAAACAACAAAACTGTGTGA
GTAGAAAGTGTCCCCTAATAAAACGTTTGGATTACCATCTTATCAGAAGATGAAAGCTCTCAAGCTAATA
TTCTATTCGTGTCATAATCAAAATTTTTTTTGTTCTAGTTTTGATCTGCTTCATTTTATACCATTAGTTTGAA
CGACGCACAGACTACAAAAGAAGAAAAAAAGGAAAAAAAAAAAAAAACATTGCGATATTTTTCCCTAATC
CTTATAAATAAGAGGGACGGAAACAGTCCAGTCCAGTCATCCATAGCAGCCCAAAGTAGGGACAGATAT
AATTCTTCATTCGTCATCTTCATCATTTCATTCATTTGACTGTTCCAACAATCCTTATTCCACGGGTGACCG
GCAATTGCAAGGTTCAACCATTACGACTCCGCCTTGTCCTATTATGGATATACATCTACTGCGCCAGAATT
AGAGTACTACTTTTCGTCTGTTCATACCTCGGGGGCACTTCCAGTTCCAGGTTGGAATTTTCCATCCTCGTT
ATTTATGTCTATTTCCTCACGTAGCTAGAGAGGTCCACCAGATCAAGCAGAAGTTTTGAATCTTTAATATA
TAGTAGCTAGAAAGATTAGTTTTATTATTTGAATCTTTAACGGTAAATCCCAATCAAGAAAGGAAAGATT
TAGAGAAAGAGTAGTAGTAATGCAATCTAAAGTTATTTTTTAAACAAAATTGCAGATAAGCACAAGCATC
TTAGTAACCGTTTGCTGCGACTGCCAGAGTTAATGAGGGTCCACCTTGATTATTTGGACTACTTTTAGTC
AATCTATCCGGCTGTTCAATACAAAATTTCGGATTTACCAGTGACATTACACACTTTGGCCCTCCATGCCA
TAGTCGCCCGCTACCCTATAAATACCCACCCATTTTCTTAAGCCTTGCTCATTCATACAAGC ACGACTTTCT
CCATTCCTTAACCATGAAAACCTTCAATTCTTTCAGCATCTCCACTCTCCTCATCATTGCTTCCCTCTCAGC
CTCCGCCCATGCTGCCACTTTCGACATCCGAAACAATTGTCCCTACACAGTCTGGGCTGCAGCGGTACCTG
GCGGTGGTCGAAGGCTAGACCGAGGCCAAACATGGACCATCAACGTGGCAGCCGGCACAGCCGGAGCTC
GTATCTGGGCTAGAACAAATTGTAACTTCGGTGGAAACGGCCGTGGCAGCTGTCAGACCGGTGACTGCGG
TGGAGTTCTTCAATGCACTGCCTACGGTAGACCACCTAATACTCTAGCAGAATACGCACTGAACCAGTTC
AATAACCTGGACTTCTTCGACATTTCCCTTGTTGATGGCTTCAATGTGCCGATGGATTTCAGCCCTACATC
CAATGGCTGCACCCGGGGCATCAGGTGCACCGCCGACATAAATGGGCAGTGCCCGAATCAGCTTCGAGC
TCCAGGAGGTTGCAACAATCCATGCACTGTTTTCAAGACTGATCAGTACTGCTGCAACTCAGGCAGCTGC
GGGCCGACCGACTATTCCAGGTTCTTCAAGACTAGGTGCCCGGATGCATACAGCTATCCGTAAGATGACA
AGACTAGCACATTCACTTGCCGAGGAGGAACCAACTATAGGGTTGTCTTTTGCCCATGAAAAGATCCTTA
AAACAAAGACTTGCTTAAGACTAGTTAAATATTTATACATGCATGGCACAATAATTGCTGGACAAAACA
TATAAGTTCATCTCAAATGCAATATTCAGTTCAAATAAAAACTATGAACTGATAATAAAGTTAATAGCTACTGGA
TGTTCGCGTTAAAAAAAAAAAAAAAAAAAA
```

FIG. 12F pAC7

ACTATAGGGCACGCGTGGTCGACGGCCCGGGCTGGTCTGGAGAGTTATAACATGGTGAAACAAAGAAGAGAATACATGGG
ACGGAAATATGAAGTCTAGTTATAAAAGCACAACGCCAGAGAAGAAAAAATTCACTTATAAGATACTTCATATCCATTTC
CTTTAGAATAATAATAATATTACTAATAATTATTACAAGAATAATACCACTTTTTATGTTGAGCTAAGCCCATTAGTTAT
GTAATTCGTCATTTTCTCTATTCGTAGAATAAAATTTTGTGATAAAACAAAATCTTTGCATCTATAATGCACGGCAAAAT
CAGCCCTTCAAAAAGAAACAACAAAACTGAGTGAGTAGAAAGTGTCCCCTAATAAAACGTTTGGATTACCATCTTATCAG
AAGATGAAAGCTCTCAAGCTAACATTCTATTCGTGTCATAATCAAAATTTTTTTGTTCTAGTTTTGATCTGCTTCATCT
TATACCATTAGTTTGAATGACGCACAGACTACAAAAGAAGAAAAAAGGAAAAAAAAAGAAACACATTGCGATATTTTC
CCTAATCCTTATAAATAAGAGGGACGGAAACAGTCCAGTCCAGTCACCCATAGCAGCCCAAAGTAGGGACAGATATAATT
CTTCATTCGTCATCTTCATCATTTCATTCATTTGACTGTTCCAACAATCCTTATTCCACGGGTGACCGGCAATTGCAAG
GTTCAACCATTGCGACTCCGCCTTGTCCTATTATGGATATACATCTACTGCGCCAGAATTAGAGTACTACTTTTCGTCTG
TTCATACCTCGGGGGCACTTCCAGTTCCAGGTTGGAATTTTCCATCCTCGTTATTTATGTCTATTTCCTCACGTAGCTAG
TGAGGTCCACCAGATCAAGCAGAAGTTTTGAATCTTTAATATATAGTAGCTAGAAAGATTAGTTTTATTATTTGAATCTT
TAACGGTAAATCCCAATCAAGAAAGGAAAGATTTAGAGAAAGAGTAGTAGTAATGCAATCTAAAGTTATTTTTTGAACA
AAATTGCAGATAAGCACAAGCATCTTAGAAACAGTTTGCTGCGACTGCCAGAGTTAATGAGGGTCCACCTTGATTATCTT
GGACTGCTTTTAGTCAATCTATCCGGCTGTTCAATACAAAATTTCGGATTTACCAGTGACATTACACACTTTGGCCCTCC
ATGCCATAGTCGCCCGCTACCCTATAAATACCCACCCATTTTCTTAAGCCTTGCTCATTCATACAAGC*ACGACTTTCTCC*
*ATTCCTTAACC*ATGAAAACCTTCAATTCTTTCAGCATCTCCACTCTTCTCATCATTGCTTTCCTCTCAACCTCCGCCAT
GCTGCCACTTTCGACATCCGAAA

FIG. 13

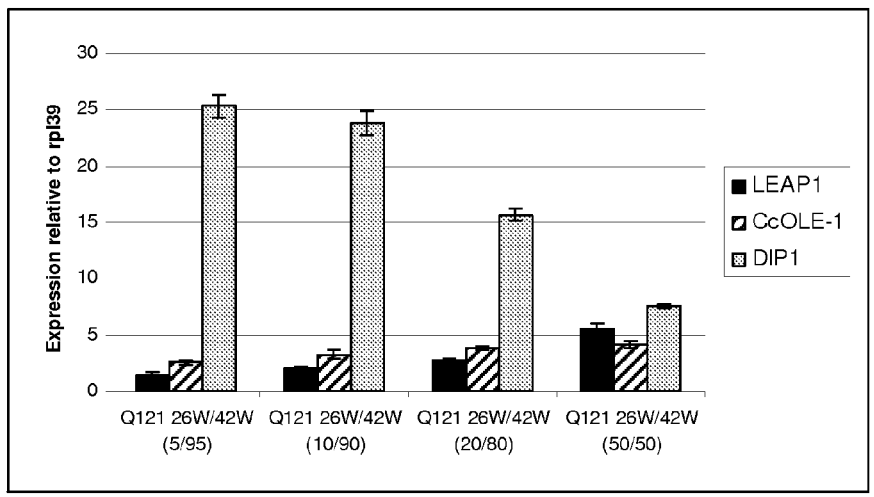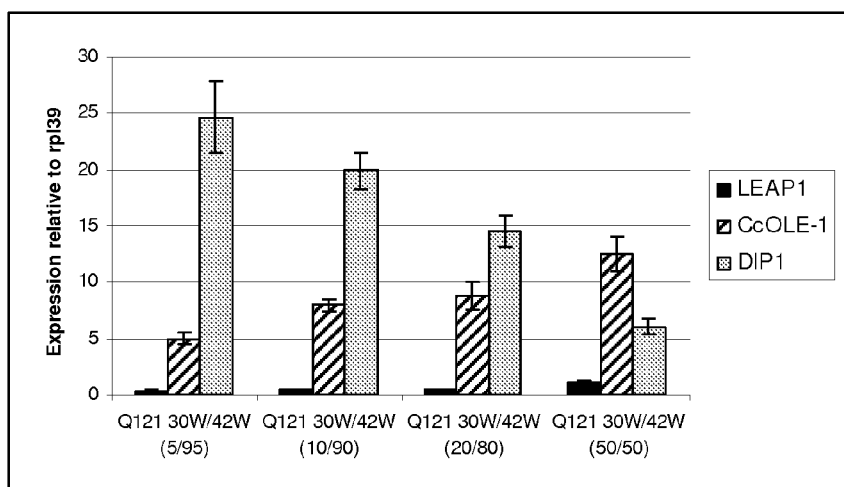
FIG. 20

| | CcOLE-1 | | DIP1 | |
|---|---|---|---|---|
| Sample | RQ moyen | Ecart-type | RQ moyen | Ecart-type |
| BP358 42w | 13,58 | 1,01 | 0,11 | 0,01 |
| BP358 46w | 4,34 | 0,26 | 3,67 | 0,37 |
| FRT09 | 0,79 | 0,11 | 1,67 | 0,16 |
| FRT49 | 1,12 | 0,60 | 1,23 | 0,09 |
| FRT53 | 1,12 | 0,19 | 0,98 | 0,12 |

Primers and probe positions for QRT-PCR for CcDIP1 cDNA

Primers and probe positions for QRT-PCR for CcRPL39 cDNA

FIG. 26

Primers and probe positions for QRT-PCR for CcOle1 cDNA

FIG. 27

Primers and probe positions for QRT-PCR for CcLEA-1 cDNA

FIG. 28

SEQUENCE LISTING

<160> NUMBER OF SEQ ID NOS: 51

<210> SEQ ID NO 1
<211> LENGTH: 1377
<212> TYPE: DNA
<213> ORGANISM: Coffea canephora

<400> SEQUENCE: 1

```
gtttcatttt tcacatctat cataaaattt cacttctgtt tacacttccc ttggcggcca      60
gtctcttaca aaatggagtt tcgacccgta catctcttca tctttgttgc tctagcttgt     120
gtgtcaagcc acgcagcaca acctgctgag acatattgga aatctgtgct ccctaacagt     180
cctatgccga aagctatcga ggatcttata caatctgaaa cggtggatga taaaagtact     240
tcagtcggag taagtggtgg tggagtagat gttaatactc agggtggaaa tccaggaggc     300
accaacgtga atgctgggca cggtggcgta gatgtaaata caccaggagg caccaatgta     360
aacgtcgggc ctggtggagt aggtgttaat acaccaggag gcaccaacgt gaatgttgga     420
```

| | | | | |
|---|---|---|---|---|
| ccgggggatc | caggaggttc | cgagacacag | ggcagaaatc | ctgaaggcac caatgtgaat | 480 |
| gtcgggcatg | gtggaggtgt | aaccgcatcc | tcaggccacc | acaggggaa accagtatat | 540 |
| gtgggaggaa | ggccagggac | atcaccattc | ttgtataact | acgcagcaac cagggatcag | 600 |
| ctccatgaca | acccaaatgt | agctcttttc | ttccttggaaa | ataacatgac tcgaggatca | 660 |
| aagatgaact | tgcatttctt | caagacttca | catggagcca | ctttcttacc tcgccaggtt | 720 |
| gctgaatcaa | ttcctttctc | atcaaacaaa | atgactgaaa | tcttgaacaa attctcagtg | 780 |
| aagcccaact | cacaggaagc | tgaagttatg | aaaaatacaa | taaagagtg cgagaagcca | 840 |
| ggcatccagg | gagaggagaa | gttctgtgca | acatcattgg | aagcaatggt agatttcacc | 900 |
| acctccaaac | tggggaagaa | cgttcaggcg | atatcaacaa | attcagagaa agatactcca | 960 |
| ctgcagaaat | ataccattgc | aggagtgaaa | aacatgacaa | atgacaaagc tgtagtgtgc | 1020 |
| caccagcaaa | attatgcata | tgctgtattt | tactgccaca | aaacacaagc tactagagca | 1080 |
| tatacacttt | ccttggtggg | tgcagatgga | acaaaagtta | aagcagtggc agtatgccat | 1140 |
| gaagatacaa | caaaatggaa | cccaaaacac | ttggctttca | aagttctgca gatcaagcca | 1200 |
| ggacaagttc | ctgtttgcca | tttccttccc | gaggatcatg | ttgtctgggt acctaaataa | 1260 |
| atatgtgcag | gaaactccaa | atgcttgccc | atttggttct | attgtaaaac aataatacac | 1320 |
| tggttgtagt | tccactaata | aacatatccc | tcttagttaa | aaaaaaaaa aaaaaaa | 1377 |

<210> SEQ ID NO 2
<211> LENGTH: 1136
<212> TYPE: DNA
<213> ORGANISM: Coffea canephora

<400> SEQUENCE: 2

| | | | | |
|---|---|---|---|---|
| aaagaacaat | tttctatttg | gtgttagaaa | aaataatacc | ggattcattc cttacttatt | 60 |
| atctactaaa | acgatgagta | ataaaaagcg | aaaacgtaaa | tgttcatgac aaatacggtt | 120 |
| atataattgg | atctatcttg | aatttatgct | aaaataaaaa | agttatacca taacaagaaa | 180 |
| accgggattg | gatatgcacc | ataatttcac | aacgccaaac | agtttccttt caaacttgca | 240 |
| agcaagaaaa | gtatgaaaat | agttaatggc | tttctgtgta | taaaaatagt agttaatagg | 300 |
| tatgcataat | acgtttatgt | gattttttg | acattcttct | gtgactgaaa gatgatcatc | 360 |
| caaatcctgt | agctaagctt | agtaaaacta | gcaaatcact | ttggatatac ttcaagtttg | 420 |
| tcagccacat | taagagcagg | attgaagcca | tacgtcaaaa | acttgaaaaa aaaactacta | 480 |
| actaatcgat | aaagatgacg | ccagattgcc | ataagcgcaa | ggcttaaaac ttgagctctc | 540 |
| aacttccagc | tgaaacccct | tgtctgatag | cattgatcaa | gtaaggattg accattatca | 600 |
| gatcagacca | gacaggatta | tcgtttgcgt | atgcaattag | gaaacaggca tctgtatctc | 660 |
| acacacaaac | gcgcagaact | tcacacatgt | aactcactga | tacatttggc tcaattggca | 720 |
| ttaatgcgtt | taagccacag | ttggaagtga | ttagagcaca | agtcatcagt agagatgatc | 780 |
| tgttgcttat | ctgctgacat | tttaccctga | acccacattc | ggctataaat agcactatag | 840 |
| ttgttgcctt | ttatcttcaa | gaaagttgtg | gtttcatttt | tcacatctat cataaaattt | 900 |
| cacttctgtt | tacacttccc | ttggcggcca | gtctcttaca | aaatggagtt tcgacccta | 960 |
| catctcttca | tctttgttgc | tgtgagtaca | acattgtatc | aattatttac gcttttgcca | 1020 |
| ataaaatgta | ttctcttta | cgccttttcc | aataaaatgt | tcacttgttc gtctgtgtgt | 1080 |
| ttcagctagc | ttgtgtgtca | agccacgcag | cacaacctgc | tgagacatat tggaaa | 1136 |

<210> SEQ ID NO 3

<211> LENGTH: 2242
<212> TYPE: DNA
<213> ORGANISM: Coffea arabica

<400> SEQUENCE: 3

```
gtcagccaca ttaagagcag gattgatgcc atacgtcaaa aacttgaaaa aaaaaactac      60
taactaatcg ataaagatga caccagattg ccataagcgt aaggcttaaa acttaagctc     120
tcaacttcca gctgaaaccc tttgtctgat agcattgatc aagtaaggat tgaccattat     180
cagatcagac cagacaggat tcccgtttgc gtatgcaatt atgaaacagg catctgtatc     240
tcacacagaa acgcgcagaa cttcacacat gtaactcact gatacatttg gctcaattgg     300
cattaatgcg tttaagccac agttggaagt gattagagca caagtcatca gtagagatga     360
tctgttgctt gtctgctgac attttaccct gaacccacat tcggctataa atagcactat     420
agttgttgcc ttttatcttc aagaaagttg tggtttcatt tttcacatct atcataaaat     480
ttcacttctg tttacacttc ccttggcagc cagtctctta caaatggag tttcgacccc      540 tacatctctt catctttgtt gctgtgagta caacattgca tcaattattt acgcttttgc     600
caataaaatg tattctcttt tacgcttttt ccaataaaat gttcacttgt tcgtctgtgt     660
gtttcagcta gcttgcgtgt caagccacgc agcacaacct gctgagacat attggaaatc     720
tgtgctccct aacagtccta tgccgaaagc tatcgaggat cttatacaat ctggtcagac     780
tcaaacctaa aagctgttct ttcactgttg ttattcaaaa acaaaatgct tttttgtctc     840
aatgcatttc atgtttctac atgccagtaa tgttctcgag aaaccacaaa ttaggcttag     900
gcaataaaca gtgatacaaa ggttaaaagg gaacgagtca gcaaactcta gaataaatac     960
tactacagag cataagacat taaattacct ttttttagca aaaaattggc aaatccggta    1020
catgaaaagg aaagtagatt tttaacagtt cttacacaag gaaaactaat cctatctaag    1080
gaaagaaaga ataagacatt aaattaccta taaggtggta agaatagtat attcatccgt    1140
gtgttcatgc taactggttg ttatggcaga acggtggat gataaaagta cttcagtcgg     1200
agtaagtggt ggtggagtag atgttaatgc tcagggtgga aatccaggag gcaccaacgt    1260
gaatgctggg cacggtggcg tagatgtaaa tacaccagga ggcaccaatg taaacgtcgg    1320
gcctggtgga gtaggtgtta ataccaccagg aggcaccaac gtgaatgttg gaccggggga    1380
tccaggaggt tccgagacac agggcagaaa tcctgaaggc accgatgtga atgtcgggca    1440
tggtggaggt gtaaccgtat cctcaggcca ccacaggggg aaaccagtat atgtgggagt    1500
aaggccaggg acatcaccat tcttgtataa ctacgcagca accaaggatc agctccatga    1560
caacccaaat gtagctcttt tcttcttgga aaataacatg actcgaggat caaagatgaa    1620
cttgcatttc ttcaagactt cacttggagc cactttctta cctcgccagg ttgctgaatc    1680
aattcctttc tcatcaaaca aaatgactga atcttgaac aaaattctcgg tgaagcccaa     1740 ctcacaggaa gctgaagtta tgaaaaatac aataaaagag tgcgagaagc caggcatcca    1800
gggagaggag aagttctgtg caacatcatt ggaagcaatg gtagatttca ccacctccaa    1860
actggggaag aacgttcagg cgatatcaac aaattcagag aaagatactc cactgcagaa    1920 ataccatt gcaggagtga aaaacatgac aaatgacaaa gctgtagtgt gccaccagca    1980
aaattatgca tatgctgtat tttactgcca caaaacacaa gctactagag catatacact    2040
ttccttggtg ggtgcagatg gaacaaaagt taaagcagtg gcagtatgcc atgaagatac    2100
aacaaaatgg aacccaaaac acttggcttt caaagttctg cagatcaagc caggacaagt    2160
tcctgtttgc catttccttc ctgaggatca tgttgtctgg gtacctaaat aaatatgtgc    2220
```
aggaaactcc aaatgcttgc cc        2242

<210> SEQ ID NO 4
<211> LENGTH: 1220
<212> TYPE: DNA
<213> ORGANISM: Coffea canephora

<400> SEQUENCE: 4

| | | | | | |
|---|---|---|---|---|---|
| ttcactccgt | cttgcatact | agcagcctac | cgtggctcgt | gcgcataaac | tattatggaa | 60 |
| tttctgaagc | ttctctactt | tctctctttt | cttttctag | gagttggggc | aaaccatgca | 120 |
| gatcttgaag | cctactggaa | atccgagctt | ccaaacactc | ctatgcccaa | agctgttaga | 180 |
| gacctgctaa | aagatgggaa | gtggccggaa | aggggcaatt | tcaggttgaa | aacatatgat | 240 |
| gacagctgta | gtttcaaaca | ttattgtgga | aatcctactg | aagatgagct | ccatattgac | 300 |
| ccaaaagtga | aagtcttttt | cttgaaaatg | gacctcaatc | gcggctcaag | catgaatatg | 360 |
| aagtttgttg | aatcagtgaa | aagtcctacg | gctttcctgc | cccgccaggt | tgctaattcg | 420 |
| attcccttct | catcaaaatc | tgttcctgaa | attttgaaca | atactcact | gaatccacaa | 480 |
| tcacaagatg | ctagaattat | taaggaaacg | atagcagaat | gcgaggtgcc | cgcaatgaaa | 540 |
| ggagaagaca | agtattgtgc | gacttctctc | gaatcaatgg | ttgatttcac | tacttcaaag | 600 |
| ctgggcaaag | atgttctagc | aatttctaac | gaagcacaga | aaacagatcc | agaagtccag | 660 |
| aaatatggta | ttgtgtctgt | ttccaagttg | aacaacaacg | ataaagaaat | agtttcttgc | 720 |
| cacaggcaaa | actatttcta | cgcagttttc | tactgccaca | ccacacagaa | tacagatgca | 780 |
| tatatggtta | atttagttgg | tgccgatgga | gcaaaagtca | aagctgtagc | tgtttgtcac | 840 |
| cgggatacgt | cagcatggaa | cccaaggcat | ttggcttttc | agctgctgaa | ggtgaagcca | 900 |
| ggaactgttc | caatctgcca | tttccttcct | gaggatcaca | ttgtctgggt | tccgaagcac | 960 |
| taaatatagt | acagaaacat | gttaacgctt | cccaagtgat | ctatgttcgt | tgctctgatg | 1020 |
| gttttacgt | atgtcttctg | cagcttggga | gttctatcca | ttatgttgcc | ataattaaat | 1080 |
| aaatccatgt | ttagtttgtt | ctctactttg | atatcaaatt | atatatgtca | atctactatt | 1140 |
| acaaagatgt | aaggtacctg | gtttcatttt | taaaaaaaaa | aaaaaaaaa | aaaaaaaaaa | 1200 |
| aaaaaaaaaa | aaaaaaaaaa | | | | | 1220 |

<210> SEQ ID NO 5
<211> LENGTH: 889
<212> TYPE: DNA
<213> ORGANISM: Coffea canephora

<400> SEQUENCE: 5

| | | | | | |
|---|---|---|---|---|---|
| acgactttct | ccattcctta | accatgaaaa | ccttcaattc | tttcagcatc | tccactcttc | 60 |
| tcatcattgc | tttcctctca | acctccgccc | atgctgccac | tttcgacatc | cgaaacaatt | 120 |
| gtccctacac | agtctgggct | gcagcggtac | ctggcgtgg | tcgaaggcta | gaccgaggcc | 180 |
| aaacatggac | catcaacgtg | gcagccggca | cagccggagc | tcgtatctgg | gctagaacaa | 240 |
| attgtaactt | cgatggaaac | ggccgtggca | gctgtcagac | cggtgactgc | ggtggagttc | 300 |
| ttcaatgcac | tgcctacggt | agaccaccta | atactctagc | agaatacgca | ctgaaccagt | 360 |
| tcaataacct | ggacttcttc | gacatttccc | ttgttgatgg | cttcaatgtg | ccgatggatt | 420 |
| tcagccctac | atccaatggc | tgcacccggg | gcatcaggtg | caccgccgac | ataaatgggc | 480 |
| agtgcccaag | tgtgcttaaa | gctccaggag | gttgcaacaa | tccatgcact | gttttcaaga | 540 |
| ctgatcagta | ttgctgcaac | tcaggcagct | gcagtgcgac | tgactattcc | aggttcttca | 600 |

```
agactaggtg cccggatgca tacagctatc cgaaagatga ccagactagc acattcactt    660
gccgaggagg aaccaactat agggttgtct tttgcccatg aaaagatcct aaaacaaag    720 acttgcttga gactagttaa atagttatac atgcatggca caataatttg ctggacacaa    780
cacataacgt catctgcaaa tgcaatattc agttcaaata aaaactatga actgataata    840
aagttaatag ctactggatg ttcgcgttaa aaaaaaaaa aaaaaaaa                  889
```

<210> SEQ ID NO 6
<211> LENGTH: 1380
<212> TYPE: DNA
<213> ORGANISM: Coffea arabica

<400> SEQUENCE: 6

```
actatagggc acgcgtggtc gacggcccgg gctggtctgg agagttataa catggtgaaa     60
caaagaagag aatacatggg acggaaatat gaagtctagt tataaaagca caacgccaga   120
gaagaaaaaa ttcacttata agatacttca tatccatttc ctttagaata taataaatat   180
tactaataat tattacaaga ataataccac ttttatgtt gagctaagcc cattagttat    240
gtaattcgtc atttctcta ttcgtagaat aaaattttgt gataaaacaa atctttgca    300 tctataatgc acggcaaaat cagcccttca aaagaaaca acaaaactga gtgagtagaa   360
agtgtcccct aataaaacgt ttggattacc atcttatcag aagatgaaag ctctcaagct   420
aacattctat tcgtgtcata atcaaaattt ttttttgttct agttttgatc tgcttcatct   480
tataccatta gtttgaatga cgcacagact acaaaagaag aaaaaaggaa aaaaaagaa   540 acacattgcg atattttttcc ctaatcctta taaataagag ggacggaaac agtccagtcc   600
agtcacccat agcagcccaa gtagggaca gatataattc ttcattcgtc atcttcatca   660
tttcattcat ttgactgttc caacaatcct tattccacgg gtgaccggca attgcaaggt   720
tcaaccattg cgactccgcc ttgtcctatt atggatatac atctactgcg ccagaattag   780
agtactactt ttcgtctgtt catacctcgg gggcacttcc agttccaggt tggaattttc   840
catcctcgtt atttatgtct atttcctcac gtagctagtg aggtccacca gatcaagcag   900
aagttttgaa tctttaatat atagtagcta gaaagattag ttttattatt tgaatcttta   960
acggtaaatc ccaatcaaga aaggaaagat ttagagaaag agtagtagta atgcaatcta  1020
aagttatttt ttgaacaaaa ttgcagataa gcacaagcat cttagaaaca gtttgctgcg  1080
actgccagag ttaatgaggg tccaccttga ttatcttgga ctgcttttag tcaatctatc  1140
cggctgttca atacaaaatt tcggatttac cagtgacatt acacactttg ccctccatg   1200 ccatagtcgc ccgctaccct ataaatacc acccattttc ttaagccttg ctcattcata  1260
caagcacgac tttctccatt ccttaaccat gaaaaccttc aattctttca gcatctccac  1320
tcttctcatc attgctttcc tctcagcctc cgcccatgct gccactttcg acatccgaaa  1380
```

<210> SEQ ID NO 7
<211> LENGTH: 1998
<212> TYPE: DNA
<213> ORGANISM: Coffea arabica

<400> SEQUENCE: 7

```
gaagagaata catgggacgg aaatatgatg tctagttata aaagcacaac gccagagaag     60
aaaaaattca cttataagat acttcatatc catttccttt agaataataa taatattact   120
aataattatt acaagaataa taccgctttt tatgttgagc taagcccatt agttatgtaa   180
ttcatcattt tctctattcg tagaataaaa ttttgtgata aacaaaatc tttgcatcta    240
```

-continued

```
taatgcacgg caaaatcagc ccttcaaaaa gaaacaacaa aactgtgtga gtagaaagtg    300
tcccctaata aaacgtttgg attaccatct tatcagaaga tgaaagctct caagctaata    360
ttctattcgt gtcataatca aaattttttt tgttctagtt ttgatctgct tcattttata    420
ccattagttt gaacgacgca cagactacaa agaagaaaaa aaaggaaaaa aaaaaaaaac    480
attgcgatat ttttccctaa tccttataaa taagagggac ggaaacagtc cagtccagtc    540
atccatagca gcccaaagta gggacagata taattcttca ttcgtcatct tcatcatttc    600
attcatttga ctgttccaac aatccttatt ccacgggtga ccggcaattg caaggttcaa    660
ccattacgac tccgccttgt cctattatgg atatacatct actgcgccag aattagagta    720
ctacttttcg tctgttcata cctcgggggc acttccagtt ccaggttgga attttccatc    780
ctcgttattt atgtctattt cctcacgtag ctagagaggt ccaccagatc aagcagaagt    840
tttgaatctt taatatatag tagctagaaa gattagtttt attatttgaa tctttaacgg    900
taaatcccaa tcaagaaagg aaagatttag agaaagagta gtagtaatgc aatctaaagt    960
tatttttta acaaaattgc agataagcac aagcatctta gtaaccgttt gctgcgactg   1020
ccagagttaa tgagggtcca ccttgattat tttggactac ttttagtcaa tctatccggc   1080
tgttcaatac aaaatttcgg atttaccagt gacattacac actttggccc tccatgccat   1140
agtcgcccgc tacctataa atacccaccc attttcttaa gccttgctca ttcatacaag   1200
cacgactttc tccattcctt aaccatgaaa accttcaatt ctttcagcat ctccactctc   1260
ctcatcattg cttccctctc agcctccgcc catgctgcca ctttcgacat ccgaaacaat   1320
tgtccctaca cagtctgggc tgcagcggta cctggcggtg gtcgaaggct agaccgaggc   1380
caaacatgga ccatcaacgt ggcagccggc acagccggag ctcgtatctg ggctagaaca   1440
aattgtaact tcggtggaaa cggccgtggc agctgtcaga ccggtgactg cggtggagtt   1500
cttcaatgca ctgcctacgg tagaccacct aatactctag cagaatacgc actgaaccag   1560
ttcaataacc tggacttctt cgacatttcc cttgttgatg gcttcaatgt gccgatggat   1620
ttcagcccta catccaatgg ctgcacccgg ggcatcaggt gcaccgccga cataaatggg   1680
cagtgcccga atcagcttcg agctccagga ggttgcaaca atccatgcac tgttttcaag   1740
actgatcagt actgctgcaa ctcaggcagc tgcgggccga ccgactattc caggttcttc   1800
aagactaggt gcccggatgc atacagctat ccgtaagatg acaagactag cacattcact   1860
tgccgaggag gaaccaacta tagggttgtc ttttgcccat gaaaagatcc ttaaaacaaa   1920
gacttgctta agactagtta aatatttata catgcatggc acaataattt gctggacaca   1980
acacataacg tcatctgc                                                 1998
```

<210> SEQ ID NO 8
<211> LENGTH: 395
<212> TYPE: PRT
<213> ORGANISM: Coffea canephora

<400> SEQUENCE: 8

```
Met Glu Phe Arg Pro Val His Leu Phe Ile Phe Val Ala Leu Ala Cys
1               5                   10                  15

Val Ser Ser His Ala Ala Gln Pro Ala Glu Thr Tyr Trp Lys Ser Val
            20                  25                  30

Leu Pro Asn Ser Pro Met Pro Lys Ala Ile Glu Asp Leu Ile Gln Ser
        35                  40                  45

Glu Thr Val Asp Asp Lys Ser Thr Ser Val Gly Val Ser Gly Gly Gly
    50                  55                  60
```

```
Val Asp Val Asn Thr Gln Gly Gly Asn Pro Gly Gly Thr Asn Val Asn
 65                  70                  75                  80

Ala Gly His Gly Gly Val Asp Val Asn Thr Pro Gly Gly Thr Asn Val
             85                  90                  95

Asn Val Gly Pro Gly Gly Val Val Asn Thr Pro Gly Gly Thr Asn
        100                 105                 110

Val Asn Val Gly Pro Gly Asp Pro Gly Gly Ser Glu Thr Gln Gly Arg
        115                 120                 125

Asn Pro Glu Gly Thr Asn Val Asn Val Gly His Gly Gly Val Thr
        130                 135                 140

Ala Ser Ser Gly His His Arg Gly Lys Pro Val Tyr Val Gly Gly Arg
145                 150                 155                 160

Pro Gly Thr Ser Pro Phe Leu Tyr Asn Tyr Ala Ala Thr Arg Asp Gln
                165                 170                 175

Leu His Asp Asn Pro Asn Val Ala Leu Phe Phe Leu Glu Asn Asn Met
                180                 185                 190

Thr Arg Gly Ser Lys Met Asn Leu His Phe Phe Lys Thr Ser His Gly
                195                 200                 205

Ala Thr Phe Leu Pro Arg Gln Val Ala Glu Ser Ile Pro Phe Ser Ser
210                 215                 220

Asn Lys Met Thr Glu Ile Leu Asn Lys Phe Ser Val Lys Pro Asn Ser
225                 230                 235                 240

Gln Glu Ala Glu Val Met Lys Asn Thr Ile Lys Glu Cys Glu Lys Pro
                245                 250                 255

Gly Ile Gln Gly Glu Lys Phe Cys Ala Thr Ser Leu Glu Ala Met
            260                 265                 270

Val Asp Phe Thr Thr Ser Lys Leu Gly Lys Asn Val Gln Ala Ile Ser
            275                 280                 285

Thr Asn Ser Glu Lys Asp Thr Pro Leu Gln Lys Tyr Thr Ile Ala Gly
290                 295                 300

Val Lys Asn Met Thr Asn Asp Lys Ala Val Val Cys His Gln Gln Asn
305                 310                 315                 320

Tyr Ala Tyr Ala Val Phe Tyr Cys His Lys Thr Gln Ala Thr Arg Ala
                325                 330                 335

Tyr Thr Leu Ser Leu Val Gly Ala Asp Gly Thr Lys Val Lys Ala Val
            340                 345                 350

Ala Val Cys His Glu Asp Thr Thr Lys Trp Asn Pro Lys His Leu Ala
            355                 360                 365

Phe Lys Val Leu Gln Ile Lys Pro Gly Gln Val Pro Val Cys His Phe
370                 375                 380

Leu Pro Glu Asp His Val Val Trp Val Pro Lys
385                 390                 395

<210> SEQ ID NO 9
<211> LENGTH: 302
<212> TYPE: PRT
<213> ORGANISM: Coffea canephora

<400> SEQUENCE: 9

Met Glu Phe Leu Lys Leu Leu Tyr Phe Leu Ser Phe Leu Phe Leu Gly
 1               5                  10                  15

Val Gly Ala Asn His Ala Asp Leu Glu Ala Tyr Trp Lys Ser Glu Leu
            20                  25                  30

Pro Asn Thr Pro Met Pro Lys Ala Val Arg Asp Leu Leu Lys Asp Gly
            35                  40                  45
```

-continued

Lys Trp Pro Glu Arg Gly Asn Phe Arg Leu Lys Thr Tyr Asp Asp Ser
    50                  55                  60

Cys Ser Phe Lys His Tyr Cys Gly Asn Pro Thr Glu Asp Glu Leu His
65                  70                  75                  80

Ile Asp Pro Lys Val Lys Val Phe Phe Leu Lys Met Asp Leu Asn Arg
                85                  90                  95

Gly Ser Ser Met Asn Met Lys Phe Val Glu Ser Val Lys Ser Pro Thr
            100                 105                 110

Ala Phe Leu Pro Arg Gln Val Ala Asn Ser Ile Pro Phe Ser Ser Lys
        115                 120                 125

Ser Val Pro Glu Ile Leu Asn Lys Tyr Ser Leu Asn Pro Gln Ser Gln
    130                 135                 140

Asp Ala Arg Ile Ile Lys Glu Thr Ile Ala Glu Cys Glu Val Pro Ala
145                 150                 155                 160

Met Lys Gly Glu Asp Lys Tyr Cys Ala Thr Ser Leu Glu Ser Met Val
                165                 170                 175

Asp Phe Thr Thr Ser Lys Leu Gly Lys Asp Val Leu Ala Ile Ser Asn
            180                 185                 190

Glu Ala Gln Lys Thr Asp Pro Glu Val Gln Lys Tyr Gly Ile Val Ser
        195                 200                 205

Val Ser Lys Leu Asn Asn Asn Asp Lys Glu Ile Val Ser Cys His Arg
    210                 215                 220

Gln Asn Tyr Phe Tyr Ala Val Phe Tyr Cys His Thr Thr Gln Asn Thr
225                 230                 235                 240

Asp Ala Tyr Met Val Asn Leu Val Gly Ala Asp Gly Ala Lys Val Lys
                245                 250                 255

Ala Val Ala Val Cys His Arg Asp Thr Ser Ala Trp Asn Pro Arg His
            260                 265                 270

Leu Ala Phe Gln Leu Leu Lys Val Lys Pro Gly Thr Val Pro Ile Cys
        275                 280                 285

His Phe Leu Pro Glu Asp His Ile Val Trp Val Pro Lys His
    290                 295                 300

<210> SEQ ID NO 10
<211> LENGTH: 225
<212> TYPE: PRT
<213> ORGANISM: Coffea canephora

<400> SEQUENCE: 10

Met Lys Thr Phe Asn Ser Phe Ser Ile Ser Thr Leu Leu Ile Ile Ala
1               5                   10                  15

Phe Leu Ser Thr Ser Ala His Ala Ala Thr Phe Asp Ile Arg Asn Asn
            20                  25                  30

Cys Pro Tyr Thr Val Trp Ala Ala Ala Val Pro Gly Gly Gly Arg Arg
        35                  40                  45

Leu Asp Arg Gly Gln Thr Trp Thr Ile Asn Val Ala Ala Gly Thr Ala
    50                  55                  60

Gly Ala Arg Ile Trp Ala Arg Thr Asn Cys Asn Phe Asp Gly Asn Gly
65                  70                  75                  80

Arg Gly Ser Cys Gln Thr Gly Asp Cys Gly Gly Val Leu Gln Cys Thr
                85                  90                  95

Ala Tyr Gly Arg Pro Pro Asn Thr Leu Ala Glu Tyr Ala Leu Asn Gln
            100                 105                 110

Phe Asn Asn Leu Asp Phe Phe Asp Ile Ser Leu Val Asp Gly Phe Asn
        115                 120                 125

```
Val Pro Met Asp Phe Ser Pro Thr Ser Asn Gly Cys Thr Arg Gly Ile
        130                 135                 140

Arg Cys Thr Ala Asp Ile Asn Gly Gln Cys Pro Ser Val Leu Lys Ala
145                 150                 155                 160

Pro Gly Gly Cys Asn Asn Pro Cys Thr Val Phe Lys Thr Asp Gln Tyr
                165                 170                 175

Cys Cys Asn Ser Gly Ser Cys Ser Ala Thr Asp Tyr Ser Arg Phe Phe
                180                 185                 190

Lys Thr Arg Cys Pro Asp Ala Tyr Ser Tyr Pro Lys Asp Asp Gln Thr
            195                 200                 205

Ser Thr Phe Thr Cys Arg Gly Gly Thr Asn Tyr Arg Val Val Phe Cys
    210                 215                 220

Pro
225

<210> SEQ ID NO 11
<211> LENGTH: 268
<212> TYPE: PRT
<213> ORGANISM: Coffea arabica

<400> SEQUENCE: 11

Met Arg Val His Leu Asp Tyr Phe Gly Leu Leu Val Asn Leu Ser
1               5                   10                  15

Gly Cys Ser Ile Gln Asn Phe Gly Phe Thr Ser Asp Ile Thr His Phe
                20                  25                  30

Gly Pro Pro Cys His Ser Arg Pro Leu Pro Tyr Lys Tyr Pro Pro Ile
            35                  40                  45

Phe Leu Ser Leu Ala His Ser Tyr Lys His Asp Phe Leu His Ser Leu
    50                  55                  60

Thr Met Lys Thr Phe Asn Ser Phe Ser Ile Ser Thr Leu Leu Ile Ile
65                  70                  75                  80

Ala Ser Leu Ser Ala Ser Ala His Ala Ala Thr Phe Asp Ile Arg Asn
                85                  90                  95

Asn Cys Pro Tyr Thr Val Trp Ala Ala Ala Val Pro Gly Gly Gly Arg
                100                 105                 110

Arg Leu Asp Arg Gly Gln Thr Trp Thr Ile Asn Val Ala Ala Gly Thr
            115                 120                 125

Ala Gly Ala Arg Ile Trp Ala Arg Thr Asn Cys Asn Phe Gly Gly Asn
        130                 135                 140

Gly Arg Gly Ser Cys Gln Thr Gly Asp Cys Gly Gly Val Leu Gln Cys
145                 150                 155                 160

Thr Ala Tyr Gly Arg Pro Pro Asn Thr Leu Ala Glu Tyr Ala Leu Asn
                165                 170                 175

Gln Phe Asn Asn Leu Asp Phe Phe Asp Ile Ser Leu Val Asp Gly Phe
            180                 185                 190

Asn Val Pro Met Asp Phe Ser Pro Thr Ser Asn Gly Cys Thr Arg Gly
            195                 200                 205

Ile Arg Cys Thr Ala Asp Ile Asn Gly Gln Cys Pro Asn Gln Leu Arg
    210                 215                 220

Ala Pro Gly Gly Cys Asn Asn Pro Cys Thr Val Phe Lys Thr Asp Gln
225                 230                 235                 240

Tyr Cys Cys Asn Ser Gly Ser Cys Gly Pro Thr Asp Tyr Ser Arg Phe
                245                 250                 255

Phe Lys Thr Arg Cys Pro Asp Ala Tyr Ser Tyr Pro
            260                 265
```

```
<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
gaacaggccc atcccttatt g                                              21

<210> SEQ ID NO 13
<211> LENGTH: 17
<212> TYPE: DNA
<213> ORGANISM: Artificial
<220> FEATURE:
<223> OTHER INFORMATION: primer

<400> SEQUENCE: 13
cggcgcttgg cattgta                                                   17

<210> SEQ ID NO 14
<211> LENGTH: 16
<212> TYPE: DNA
<213> ORGANISM: Artificial
<220> FEATURE:
<223> OTHER INFORMATION: probe

<400> SEQUENCE: 14
atgcgcactg acaaca                                                    16

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
cccaaaacac ttggctttca a                                              21

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
gaaatggcaa acaggaactt gtc                                            23

<210> SEQ ID NO 17
<211> LENGTH: 16
<212> TYPE: DNA
<213> ORGANISM: Artificial
<220> FEATURE:
<223> OTHER INFORMATION: probe

<400> SEQUENCE: 17
tctgcagatc aagcca                                                    16

<210> SEQ ID NO 18
<211> LENGTH: 19
<212> TYPE: DNA
<213> ORGANISM: Artificial
<220> FEATURE:
<223> OTHER INFORMATION: primer
```

-continued

```
<400> SEQUENCE: 18
tggctcgtgc gcataaact                                              19

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
tgggcatagg agtgtttgga a                                           21

<210> SEQ ID NO 20
<211> LENGTH: 20
<212> TYPE: DNA
<213> ORGANISM: Artificial
<220> FEATURE:
<223> OTHER INFORMATION: probe

<400> SEQUENCE: 20
ttatggaatt tctgaagctt                                             20

<210> SEQ ID NO 21
<211> LENGTH: 17
<212> TYPE: DNA
<213> ORGANISM: Artificial
<220> FEATURE:
<223> OTHER INFORMATION: primer

<400> SEQUENCE: 21
ggtgcaccgc cgacata                                                17

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
caacctcctg gagctttaag ca                                          22

<210> SEQ ID NO 23
<211> LENGTH: 15
<212> TYPE: DNA
<213> ORGANISM: Artificial
<220> FEATURE:
<223> OTHER INFORMATION: probe

<400> SEQUENCE: 23
tgggcagtgc ccaag                                                  15

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
ccgactcatg aaggcgtctt                                             20

<210> SEQ ID NO 25
<211> LENGTH: 18
<212> TYPE: DNA
```

<213> ORGANISM: Artificial
<220> FEATURE:
<223> OTHER INFORMATION: primer

<400> SEQUENCE: 25
gtcctgcagc gccacttt                                          18

<210> SEQ ID NO 26
<211> LENGTH: 14
<212> TYPE: DNA
<213> ORGANISM: Artificial
<220> FEATURE:
<223> OTHER INFORMATION: probe

<400> SEQUENCE: 26
ccaggagcaa atgg                                              14

<210> SEQ ID NO 27
<211> LENGTH: 22
<212> TYPE: DNA
<213> ORGANISM: Artificial
<220> FEATURE:
<223> OTHER INFORMATION: primer

<400> SEQUENCE: 27
tctgcttcaa tatccccttc gt                                     22

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
gtgacacagt ccactaaaca gttggta                                27

<210> SEQ ID NO 29
<211> LENGTH: 16
<212> TYPE: DNA
<213> ORGANISM: Artificial
<220> FEATURE:
<223> OTHER INFORMATION: probe

<400> SEQUENCE: 29
tgccccttag actgtc                                            16

<210> SEQ ID NO 30
<211> LENGTH: 30
<212> TYPE: DNA
<213> ORGANISM: Artificial
<220> FEATURE:
<223> OTHER INFORMATION: primer

<400> SEQUENCE: 30
tcgatagctt tcggcatagg actgttaggg                             30

<210> SEQ ID NO 31
<211> LENGTH: 28
<212> TYPE: DNA
<213> ORGANISM: Artificial
<220> FEATURE:
<223> OTHER INFORMATION: primer

<400> SEQUENCE: 31
ttccaatatg tctcagcagg ttgtgctg                               28

```
<210> SEQ ID NO 32
<211> LENGTH: 25
<212> TYPE: DNA
<213> ORGANISM: Artificial
<220> FEATURE:
<223> OTHER INFORMATION: primer

<400> SEQUENCE: 32
atgtttggcc tcggtctagc cttcg                                         25

<210> SEQ ID NO 33
<211> LENGTH: 27
<212> TYPE: DNA
<213> ORGANISM: Artificial
<220> FEATURE:
<223> OTHER INFORMATION: primer

<400> SEQUENCE: 33
tttcggatgt cgaaagtggc agcatgg                                       27

<210> SEQ ID NO 34
<211> LENGTH: 22
<212> TYPE: DNA
<213> ORGANISM: Artificial
<220> FEATURE:
<223> OTHER INFORMATION: primer

<400> SEQUENCE: 34
gtaatacgac tcactatagg gc                                            22

<210> SEQ ID NO 35
<211> LENGTH: 19
<212> TYPE: DNA
<213> ORGANISM: Artificial
<220> FEATURE:
<223> OTHER INFORMATION: primer

<400> SEQUENCE: 35
actatagggc acgcgtggt                                                19

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
gaacaatttt ctatttggtg                                               20

<210> SEQ ID NO 37
<211> LENGTH: 18
<212> TYPE: DNA
<213> ORGANISM: Artificial
<220> FEATURE:
<223> OTHER INFORMATION: primer

<400> SEQUENCE: 37
tagctttcgg cataggac                                                 18

<210> SEQ ID NO 38
<211> LENGTH: 21
<212> TYPE: DNA
<213> ORGANISM: Artificial
<220> FEATURE:
<223> OTHER INFORMATION: primer
```

-continued

```
<400> SEQUENCE: 38
gtcagccaca ttaagagcag g                                              21

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
gggcaagcat ttggagtttc                                                20

<210> SEQ ID NO 40
<211> LENGTH: 19
<212> TYPE: DNA
<213> ORGANISM: Artificial
<220> FEATURE:
<223> OTHER INFORMATION: primer

<400> SEQUENCE: 40
actatagggc acgcgtggt                                                 19

<210> SEQ ID NO 41
<211> LENGTH: 26
<212> TYPE: DNA
<213> ORGANISM: Artificial
<220> FEATURE:
<223> OTHER INFORMATION: primer

<400> SEQUENCE: 41
tttcggatgt cgaaagtggc agcatg                                         26

<210> SEQ ID NO 42
<211> LENGTH: 19
<212> TYPE: DNA
<213> ORGANISM: Artificial
<220> FEATURE:
<223> OTHER INFORMATION: primer

<400> SEQUENCE: 42
gaagagaata catgggacg                                                 19

<210> SEQ ID NO 43
<211> LENGTH: 19
<212> TYPE: DNA
<213> ORGANISM: Artificial
<220> FEATURE:
<223> OTHER INFORMATION: primer

<400> SEQUENCE: 43
gcagatgacg ttatgtgtt                                                 19

<210> SEQ ID NO 44
<211> LENGTH: 364
<212> TYPE: PRT
<213> ORGANISM: Vitis vinifera

<400> SEQUENCE: 44

Met Glu Phe His Leu Leu Pro Ile Leu Ala Leu Ile Ser Leu Val Val
1               5                   10                  15

Ala Ala Gly His Ala Ala Leu Pro Thr Lys Val Tyr Trp Asn Ser Val
            20                  25                  30

Leu Pro Asn Thr Pro Met Pro Lys Ala Ile Arg Asp Ile Leu Arg Pro
        35                  40                  45
```

```
Asp Leu Met Glu Glu Lys Gly Thr Ser Val Ser Val Gly Lys Gly Gly
    50                  55                  60

Val Asn Val His Ala Gly Lys Gly Lys Ser Gly Gly Thr Thr Val
65                  70                  75                  80

Gly Val Gly Lys Gly Thr Gly Val Asn Val His Ala Gly Lys Gly Lys
                85                  90                  95

Pro Gly Gly Gly Thr Thr Val Gly Val Gly Lys Gly Gly Val Ser Val
            100                 105                 110

Asn Ala Gly His Lys Gly Lys His Val Tyr Val Gly Val Gly Lys Gly
            115                 120                 125

Lys Ser Lys Ser Pro Phe Asp Tyr Lys Tyr Ala Ala Thr Glu Asp Gln
            130                 135                 140

Leu His Asp Pro Asn Val Ala Leu Phe Phe Phe Glu Lys Asn Met
145                 150                 155                 160

Gln Pro Gly Thr Lys Met Glu Leu His Phe Ile Arg Asp Ala Asn Leu
                165                 170                 175

Ala Thr Phe Leu Pro Arg Gln Val Ala Asn Ser Ile Pro Phe Ser Ser
            180                 185                 190

Lys Lys Phe Pro Glu Ile Leu Asn Glu Phe Ser Ile Lys Pro Glu Ser
            195                 200                 205

Glu Glu Ala Glu Thr Ile Lys Asn Thr Ile Arg Glu Cys Glu Glu Pro
210                 215                 220

Gly Ile Lys Gly Glu Glu Lys Tyr Cys Ala Thr Ser Leu Glu Ser Met
225                 230                 235                 240

Val Asp Phe Ser Thr Ser Lys Leu Gly Lys Gly Val Gln Met Ile Ser
                245                 250                 255

Thr Glu Val Glu Lys Glu Thr Pro Glu Gln Gln Tyr Thr Ile Thr Thr
            260                 265                 270

Gly Val Lys Lys Leu Ala Gly Asp Lys Ala Val Val Cys His Lys Gln
            275                 280                 285

Ser Tyr Pro Tyr Ala Val Phe Tyr Cys His Lys Thr Gln Thr Thr Arg
            290                 295                 300

Ala Tyr Met Val Pro Leu Val Gly Ala Asp Gly Ser Lys Val Lys Ala
305                 310                 315                 320

Val Ala Val Cys His Thr Asp Thr Ser Ala Trp Asn Pro Lys His Leu
                325                 330                 335

Ala Phe Gln Val Leu Lys Val Lys Pro Gly Thr Val Pro Ile Cys His
            340                 345                 350

Phe Leu Pro Glu Asp His Val Val Trp Val Pro Lys
            355                 360

<210> SEQ ID NO 45
<211> LENGTH: 376
<212> TYPE: PRT
<213> ORGANISM: Gossypium arboreum

<400> SEQUENCE: 45

Met Lys Val Leu Ser Pro Ile Leu Ala Cys Leu Ala Leu Ala Val Val
1               5                   10                  15

Ala Ser His Ala Ala Leu Ser Pro Glu Gln Tyr Trp Ser Tyr Lys Leu
                20                  25                  30

Pro Asn Thr Pro Met Pro Lys Ala Val Lys Glu Ile Leu His Pro Glu
            35                  40                  45

Leu Met Glu Glu Lys Ser Thr Ser Val Asn Val Gly Gly Gly Gly Val
        50                  55                  60
```

```
Asn Val Asn Thr Gly Lys Gly Lys Pro Ala Gly Gly Thr His Val Asn
 65                  70                  75                  80

Val Gly Arg Lys Gly Val Gly Val Asn Thr Gly Lys Pro Gly Gly Gly
                 85                  90                  95

Thr His Val Asn Val Gly Gly Lys Gly Val Gly Val Asn Thr Gly Lys
            100                 105                 110

Pro Gly Gly Gly Thr His Val Asn Val Gly Gly Lys Gly Gly Gly Val
            115                 120                 125

Ser Val His Thr Gly His Lys Gly Lys Pro Val Asn Val Asn Val Ser
            130                 135                 140

Pro Phe Leu Tyr Gln Tyr Ala Ala Ser Glu Thr Gln Ile His Asp Asp
145                 150                 155                 160

Pro Asn Val Ala Leu Phe Phe Leu Glu Lys Asp Leu His Pro Gly Ala
                165                 170                 175

Thr Met Ser Leu His Phe Thr Glu Asn Thr Glu Lys Ser Ala Phe Leu
            180                 185                 190

Pro Tyr Gln Thr Ala Gln Lys Ile Pro Phe Ser Ser Asn Glu Leu Pro
                195                 200                 205

Glu Ile Phe Asn Lys Phe Ser Val Lys Pro Gly Ser Val Lys Ala Glu
210                 215                 220

Met Met Lys Asn Thr Ile Lys Glu Cys Glu Gln Pro Ala Ile Glu Gly
225                 230                 235                 240

Glu Glu Lys Tyr Cys Ala Thr Ser Leu Glu Ser Met Ile Asp Tyr Ser
                245                 250                 255

Ile Ser Lys Leu Gly Lys Val Asp Gln Ala Val Ser Thr Glu Val Glu
                260                 265                 270

Lys Gln Thr Pro Thr His Lys Tyr Thr Ile Thr Ala Gly Val Gln Lys
            275                 280                 285

Met Thr Asn Asp Lys Ala Val Val Cys His Lys Gln Asn Tyr Ala Tyr
290                 295                 300

Ala Val Phe Tyr Cys His Lys Ser Glu Thr Thr Arg Ala Tyr Met Val
305                 310                 315                 320

Pro Leu Glu Gly Ala Asp Gly Thr Lys Ala Lys Ala Val Ala Val Cys
                325                 330                 335

His Thr Asp Thr Ser Ala Trp Asn Pro Lys His Leu Ala Phe Gln Val
            340                 345                 350

Leu Lys Val Glu Pro Gly Thr Ile Pro Val Cys His Phe Leu Pro Arg
            355                 360                 365

Asp His Ile Val Trp Val Pro Lys
370                 375

<210> SEQ ID NO 46
<211> LENGTH: 335
<212> TYPE: PRT
<213> ORGANISM: Gossypium hirsutum

<400> SEQUENCE: 46

Met Lys Val Leu Ser Pro Ile Leu Ala Cys Leu Ala Leu Ala Val Val
 1               5                  10                  15

Val Ser His Ala Ala Leu Ser Pro Glu Gln Tyr Trp Ser Tyr Lys Leu
                20                  25                  30

Pro Asn Thr Pro Met Pro Lys Ala Val Lys Glu Ile Leu His Pro Glu
            35                  40                  45

Leu Met Glu Glu Lys Ser Thr Ser Val Asn Val Gly Gly Gly Gly Val
 50                  55                  60
```

Asn Val Asn Thr Gly Lys Gly Lys Pro Gly Gly Asp Thr His Val Asn
65              70              75              80

Val Gly Gly Lys Gly Val Gly Val Asn Thr Gly Lys Pro Gly Gly Gly
            85              90              95

Thr His Val Asn Val Gly Asp Pro Phe Asn Tyr Leu Tyr Ala Ala Ser
            100             105             110

Glu Thr Gln Ile His Glu Asp Pro Asn Val Ala Leu Phe Phe Leu Glu
            115             120             125

Lys Asp Met His Pro Gly Ala Thr Met Ser Leu His Phe Thr Glu Asn
130             135             140

Thr Glu Lys Ser Ala Phe Leu Pro Tyr Gln Thr Ala Gln Lys Ile Pro
145             150             155             160

Phe Ser Ser Asp Lys Leu Pro Glu Ile Phe Asn Lys Phe Ser Val Lys
            165             170             175

Pro Gly Ser Leu Lys Ala Glu Met Met Lys Asn Thr Ile Lys Glu Cys
            180             185             190

Glu Gln Pro Ala Ile Glu Gly Glu Lys Tyr Cys Ala Thr Ser Leu
            195             200             205

Glu Ser Met Ile Asp Tyr Ser Ile Ser Lys Leu Gly Lys Val Asp Gln
210             215             220

Ala Val Ser Thr Glu Val Glu Lys Gln Thr Pro Met Gln Lys Tyr Thr
225             230             235             240

Ile Ala Ala Gly Val Gln Lys Met Thr Asp Asp Lys Ala Val Val Cys
            245             250             255

His Lys Gln Asn Tyr Ala Tyr Ala Val Phe Tyr Cys His Lys Ser Glu
            260             265             270

Thr Thr Arg Ala Tyr Met Val Pro Leu Glu Gly Ala Asp Gly Thr Lys
            275             280             285

Ala Lys Ala Val Ala Val Cys His Thr Asp Thr Ser Ala Trp Asn Pro
290             295             300

Lys His Leu Ala Phe Gln Val Leu Lys Val Glu Pro Gly Thr Ile Pro
305             310             315             320

Val Cys His Phe Leu Pro Arg Asp His Ile Val Trp Val Pro Lys
            325             330             335

<210> SEQ ID NO 47
<211> LENGTH: 392
<212> TYPE: PRT
<213> ORGANISM: Arabidopsis thaliana

<400> SEQUENCE: 47

Met Ala Ile Arg Leu Pro Leu Ile Cys Leu Leu Gly Ser Phe Met Val
1               5               10              15

Val Ala Ile Ala Ala Asp Leu Thr Pro Glu Arg Tyr Trp Ser Thr Ala
            20              25              30

Leu Pro Asn Thr Pro Ile Pro Asn Ser Leu His Asn Leu Leu Thr Phe
            35              40              45

Asp Phe Thr Asp Glu Lys Ser Thr Asn Val Gln Val Gly Lys Gly Gly
        50              55              60

Val Asn Val Asn Thr His Lys Gly Lys Thr Gly Ser Gly Thr Ala Val
65              70              75              80

Asn Val Gly Lys Gly Gly Val Arg Val Asp Thr Gly Lys Gly Lys Pro
            85              90              95

Gly Gly Gly Thr His Val Ser Val Gly Ser Gly Lys Gly His Gly Gly
            100             105             110

Gly Val Ala Val His Thr Gly Lys Pro Gly Lys Arg Thr Asp Val Gly
            115                 120                 125

Val Gly Lys Gly Gly Val Thr Val His Thr Arg His Lys Gly Arg Pro
        130                 135                 140

Ile Tyr Val Gly Val Lys Pro Gly Ala Asn Pro Phe Val Tyr Asn Tyr
145                 150                 155                 160

Ala Ala Lys Glu Thr Gln Leu His Asp Asp Pro Asn Ala Ala Leu Phe
                165                 170                 175

Phe Leu Glu Lys Asp Leu Val Arg Gly Lys Glu Met Asn Val Arg Phe
            180                 185                 190

Asn Ala Glu Asp Gly Tyr Gly Lys Thr Ala Phe Leu Pro Arg Gly
            195                 200                 205

Glu Ala Glu Thr Val Pro Phe Gly Ser Glu Lys Phe Ser Glu Thr Leu
        210                 215                 220

Lys Arg Phe Ser Val Glu Ala Gly Ser Glu Glu Ala Glu Met Met Lys
225                 230                 235                 240

Lys Thr Ile Glu Glu Cys Glu Ala Arg Lys Val Ser Gly Glu Glu Lys
                245                 250                 255

Tyr Cys Ala Thr Ser Leu Glu Ser Met Val Asp Phe Ser Val Ser Lys
            260                 265                 270

Leu Gly Lys Tyr His Val Arg Ala Val Ser Thr Glu Val Ala Lys Lys
        275                 280                 285

Asn Ala Pro Met Gln Lys Tyr Lys Ile Ala Ala Gly Val Lys Lys
290                 295                 300

Leu Ser Asp Asp Lys Ser Val Val Cys His Lys Gln Lys Tyr Pro Phe
305                 310                 315                 320

Ala Val Phe Tyr Cys His Lys Ala Met Met Thr Thr Val Tyr Ala Val
                325                 330                 335

Pro Leu Glu Gly Glu Asn Gly Met Arg Ala Lys Ala Val Ala Val Cys
            340                 345                 350

His Lys Asn Thr Ser Ala Trp Asn Pro Asn His Leu Ala Phe Lys Val
        355                 360                 365

Leu Lys Val Lys Pro Gly Thr Val Pro Val Cys His Phe Leu Pro Glu
        370                 375                 380

Thr His Val Val Trp Phe Ser Tyr
385                 390

<210> SEQ ID NO 48
<211> LENGTH: 225
<212> TYPE: PRT
<213> ORGANISM: Actinidia deliciosa

<400> SEQUENCE: 48

Met Ser Thr Phe Lys Ser Leu Ser Leu Ser Ala Leu Leu Phe Ile Ala
1               5                   10                  15

Phe Leu Phe Thr Cys Ala Arg Gly Ala Thr Phe Asn Ile Ile Asn Asn
            20                  25                  30

Cys Pro Phe Thr Val Trp Ala Ala Ala Val Pro Gly Gly Gly Lys Arg
        35                  40                  45

Leu Asp Arg Gly Gln Asn Trp Ile Ile Asn Pro Gly Ala Gly Thr Lys
    50                  55                  60

Gly Ala Arg Val Trp Pro Arg Thr Gly Cys Asn Phe Asp Gly Ala Gly
65                  70                  75                  80

Arg Gly Lys Cys Gln Thr Gly Asp Cys Asn Gly Leu Leu Gln Cys Gln
                85                  90                  95

```
Ala Phe Gly Gln Pro Pro Asn Thr Leu Ala Glu Tyr Ala Leu Asn Gln
            100                 105                 110

Phe Asn Asn Leu Asp Phe Phe Asp Ile Ser Leu Val Asp Gly Phe Asn
        115                 120                 125

Val Ala Met Glu Phe Ser Pro Thr Ser Gly Gly Cys Thr Arg Gly Ile
130                 135                 140

Lys Cys Thr Ala Asp Ile Asn Gly Gln Cys Pro Asn Glu Leu Arg Ala
145                 150                 155                 160

Pro Gly Gly Cys Asn Asn Pro Cys Thr Val Phe Lys Thr Asp Gln Tyr
                165                 170                 175

Cys Cys Asn Ser Gly Asn Cys Gly Leu Thr Asn Phe Ser Lys Phe Phe
            180                 185                 190

Lys Asp Arg Cys Pro Asp Ala Tyr Ser Tyr Pro Lys Asp Gln Thr
        195                 200                 205

Ser Thr Phe Thr Cys Pro Ala Gly Thr Asn Tyr Lys Val Val Phe Cys
        210                 215                 220

Pro
225

<210> SEQ ID NO 49
<211> LENGTH: 222
<212> TYPE: PRT
<213> ORGANISM: Helianthus annuus

<400> SEQUENCE: 49

Met Thr Thr Ser Thr Leu Pro Thr Phe Leu Leu Leu Ala Ile Leu Phe
1               5                   10                  15

His Tyr Thr Asn Ala Ala Val Phe Thr Ile Arg Asn Asn Cys Pro Tyr
            20                  25                  30

Thr Val Trp Ala Gly Ala Val Pro Gly Gly Gly Arg Gln Leu Asn Ser
        35                  40                  45

Gly Gln Thr Trp Ser Leu Thr Val Ala Ala Gly Thr Ala Gly Ala Arg
    50                  55                  60

Ile Trp Pro Arg Thr Asn Cys Asn Phe Asp Gly Ser Gly Arg Gly Arg
65                  70                  75                  80

Cys Gln Thr Gly Asp Cys Asn Gly Leu Leu Gln Cys Gln Asn Tyr Gly
                85                  90                  95

Thr Pro Pro Asn Thr Leu Ala Glu Tyr Ala Leu Asn Gln Phe Asn Asn
            100                 105                 110

Leu Asp Phe Phe Asp Ile Ser Leu Val Asp Gly Phe Asn Val Pro Met
        115                 120                 125

Val Phe Arg Pro Asn Ser Asn Gly Cys Thr Arg Gly Ile Ser Cys Thr
130                 135                 140

Ala Asp Ile Asn Gly Gln Cys Pro Gly Glu Leu Arg Ala Pro Gly Gly
145                 150                 155                 160

Cys Asn Asn Pro Cys Thr Val Tyr Lys Thr Asp Gln Tyr Cys Cys Asn
                165                 170                 175

Ser Gly Asn Cys Gly Pro Thr Asp Leu Ser Arg Phe Phe Lys Thr Arg
            180                 185                 190

Cys Pro Asp Ala Tyr Ser Tyr Pro Lys Asp Asp Pro Thr Ser Thr Phe
        195                 200                 205

Thr Cys Pro Gly Gly Thr Asn Tyr Asp Val Ile Phe Cys Pro
210                 215                 220

<210> SEQ ID NO 50
```

```
<211> LENGTH: 226
<212> TYPE: PRT
<213> ORGANISM: Fragaria x ananassa

<400> SEQUENCE: 50

Met Ser Leu Leu Lys Asn Leu Pro Thr Val Leu Ser Ile Leu Tyr Phe
1               5                   10                  15

Ala Ala Ser Thr Val Asn Ala Ala Thr Phe Asn Lys Lys Asn Asn Cys
            20                  25                  30

Pro Phe Thr Val Trp Ala Gly Ala Val Pro Gly Gly Gly Lys Gln Leu
        35                  40                  45

Gly Thr Gly Gln Thr Trp Thr Ile Asn Val Ala Ala Gly Thr Lys Gly
    50                  55                  60

Ala Arg Ile Trp Pro Arg Thr Asn Cys Asn Phe Asp Gly Ala Gly Arg
65                  70                  75                  80

Gly Arg Cys Gln Thr Gly Asp Cys Gly Gly Leu Leu Gln Cys Gln Gly
                85                  90                  95

Tyr Gly Gln Pro Pro Asn Thr Leu Ala Glu Tyr Ala Leu Asn Gln Tyr
            100                 105                 110

Met Asn Arg Asp Phe Tyr Asp Ile Ser Leu Ile Asp Gly Phe Asn Val
        115                 120                 125

Pro Met Asp Phe Ser Pro Val Ser Asn Gly Cys Thr Arg Gly Ile Arg
    130                 135                 140

Cys Thr Ala Asp Ile Asn Gly Gln Cys Pro Ala Gln Leu Arg Ala Pro
145                 150                 155                 160

Gly Gly Cys Asn Asn Ala Cys Thr Val Ser Lys Thr Asp Gln Tyr Cys
                165                 170                 175

Cys Asn Ser Gly His Cys Gly Pro Thr Asp Tyr Ser Arg Phe Phe Lys
            180                 185                 190

Ser Arg Cys Pro Asp Ala Tyr Ser Tyr Pro Lys Asp Asp Ala Thr Ser
        195                 200                 205

Thr Val Leu Phe Thr Cys Pro Gly Gly Thr Asn Tyr Arg Val Val Phe
    210                 215                 220

Cys Pro
225

<210> SEQ ID NO 51
<211> LENGTH: 25
<212> TYPE: DNA
<213> ORGANISM: Artificial
<220> FEATURE:
<223> OTHER INFORMATION: primer

<400> SEQUENCE: 51
cgaaggctag accgaggcca aacat                                    25
```

GENES FOR MODULATING COFFEE MATURATION AND METHODS FOR THEIR USE

SEQUENCE LISTING

A sequence listing comprising SEQ ID NOs:1-51 is attached hereto. Each sequence provided in the sequence listing is incorporated by reference in its entirety herein for all purposes.

BACKGROUND OF THE INVENTION

1. Field of the Invention

The invention relates generally to agricultural biotechnology. In particular, the invention relates to polynucleotides isolated from coffee plants that are expressed predominantly during the late stages of grain development and maturation. It also relates to promoters that regulate expression of these polynucleotides in plants and methods for their use.

2. Description of the Related Art

The development and maturation of seeds, including those of coffee (grain/bean), follows a specific, tightly-regulated developmental pathway that is driven by temporally-distinct changes in gene and protein expression (Girke, T. et al., 2000; Fait, A. et al., 2006; Hajduch, M. et al., 2005; De Castro, R. D. and Marraccini, P., 2006)). Any genetic modification of a seed requires that the added "modified" transgene(s) be controlled by a promoter sequence capable of "driving" expression in the seed. To limit the "interference" of the introduced transgene on other parts of the plant, it is often desirable that the promoter used to drive the transgene's expression functions only at a specific times, e.g., under particular conditions or during a particular stage of seed development.

There are currently several coffee DNA promoter sequences available. Some are capable of driving strong expression of transgenes in green tissue like leaves, and potentially very weak expression in immature grain such as the rbcS promoter (Marraccini, P. and Rogers J., 2006). Leaf-specific gene promoters from coffee are capable of directing strong expression primarily in the coffee seed during endosperm formation and expansion, see for example U.S. Pat. No. 7,153,953; also 11S promoter (Marraccini, P. and Rogers J., 2003), coffee storage protein promoter (U.S. Pat. No. 6,617,433); oleosin promoter (WO 2007/005928, Simkin, A. J. et al., 2006b), an dehydrin promoter (WO 2007/005980, Tanksley, S. et al., 2007) and (Hinniger, C. et al., 2006).

However, there are currently no coffee promoters available that control strong expression of recombinant genes, exclusively, or nearly exclusively, during late coffee grain maturation. That stage is the maturation stage, involving partial seed dehydration. There are very few well-characterized late grain-specific promoters described in the literature for any seeds. It is considered important to have such genetic elements, to better understand seed maturation, including of coffee grain. Such promoters would have many uses, including improving the quality of coffee in the consumer's cup. These promoters would also allow experimental work, such as testing the effect of expressing recombinant genes at late stages of seed development.

For example, in attempts to improve the quality or extractability of coffee, it is possible that expressing candidate genes during endosperm development/expansion could cause defects in the grain. Expressing the same candidate genes later in development, however, may have no effect on the grain structure/function. Because it is important to test the effects of expressing candidate "coffee quality" gene sequences during the late stages of development there is a need for late grain development promoters.

In the field, coffee maturity is generally considered to be represented by red cherries, and/or softening of the coffee cherry fruit (pericarp). However, there is little detailed experimental evidence indicating that the grain of all fully red cherries have reached complete maturity in all the different commercial varieties. In fact, it is conceivable that the "red" color development of the cherries can, at least in a few varieties, occur faster than the final development of the internal coffee grain. Furthermore, although ideally all coffee is harvested at the red cherry stage, there is a significant level of harvesting, including mechanical harvesting of C. arabica, which includes less ripe yellow and sometimes even green/yellow cherries. Therefore, lots or batches of harvested coffee can contain certain levels of immature grain. In addition, unscrupulous traders have been known to mix batches of immature and mature cherries to prepare coffee lots that are "acceptable" to buyers because "immaturity-related" defects are less evident.

The presence of such immature beans can result in a major defect of green coffee ((Farah, A. and Donangelo, C. M., 2006) and references therein). The lower flavour quality associated with immature beans is likely to be due to multiple factors, including differences in the grain structure before and after full maturation. Certain components present in the immature grain may be potentially detrimental to the flavour quality when immature beans are present in lots of harvested coffee. For example, lower levels of sucrose (Geromel, C. et al., 2006; Privat, I. et al., 2006), nucleic acids and proteins associated with sucrose accumulation in coffee (WO 2007/022318 A2) and higher levels of chlorogenic acids (Farah, A. and Donangelo, C. M., 2006) may all adversely impact coffee flavour and quality.

As indicated above, the presence of immature grain, whether through lack of quality assurance, lack of adequate harvesting practices, or lack of ethics (e.g., intentional deception), results in suboptimal or inferior coffee and is problematic for buyers of quality or premium coffees. There are currently no tests available to measure the maturity level of stored grains, such as coffee grains, particularly where the harvesting practices, mixing, or storage conditions are either not known, or not under the direct control of the buyer. There is a need for methods and techniques capable of detecting the presence of immature grain in lots of coffee in agricultural or industrial settings. Such methods would be useful, for example, within the coffee trade, where the results could reflect the maturity of the lot, and thus determine the quality, grading, acceptability, or value of the lot. Such methods would also be useful for determining the properties of other valuable grains or seeds including corn, soya, etc.).

There remains a need, therefore, for genes and promoters from plants that are expressed predominantly during the late stages of grain development and maturation. In particular, there is a need for such polynucleotides from coffee, as well as methods for the use of these polypeptides in assessing the quality of grains used as agricultural commodities.

SUMMARY OF THE INVENTION

Presented are the identification and isolation of genes that are predominantly, or even exclusively, expressed in the grain at the late stage of development, and that show significant amounts expression during that period. Candidate genes were first selected from the Coffee EST Database at Cornell's SOL Genomics Network. The SGN coffee EST Database was generated based on sequences from approximately 47,000 cDNA clones derived from five different stages/tissues, with a special focus on developing seeds. According to its description "[w]hen computationally assembled, these sequences correspond to 13,175 unigenes, which were analyzed with respect to functional annotation, expression profile and evolution." (see Lin et al., Theor. Appl. Genet. (2005) November 5; 1-17).

Two of the selected candidate genes, later named DIP1 and PR-5A, were then selected for further detailed study. The promoters were isolated, and DNA sequences were confirmed. Analysis showed that DIP1 was grain specific, and its promoter was deemed a very good candidate promoter for use in the expression of recombinant proteins particularly at the last stage of coffee grain development.

In a first of several aspects, the invention provides nucleic acid molecules isolated from coffee (*Coffea* spp.). The nucleic acid molecules have a coding sequence that encodes a protein comprising one or more of a BURP domain, 16 conserved cysteines residues of a pathogenesis-related protein, or a thaumatin domain. Preferred nucleic acid molecules are provided in the appended sequence listing as SEQ ID NOs:1, 3, 4, 5, and 7. Preferably, these molecules encodes the proteins whose sequences are provided as SEQ ID NOs:8-11. Also provided are genes comprising the nucleic acid molecules, mRNA molecules produced by transcription of those genes, cDNA molecule produced by reverse transcription of the mRNA molecules, and vectors comprising the nucleic acid molecules provided herein. Host cells comprising the nucleic acids and vectors are also provided, as well as fertile transgenic plants encompassing the nucleic acids provided herein.

As the skilled artisan will appreciate, because of the base-pairing properties of nucleic acid molecules, and because the informational content of two complementary nucleic acid molecules can be identical, the complement of the nucleic acid molecules described herein is also provided. Similarly cDNAs that comprise any of the nucleic acid molecules described herein, or their complements, are also provided.

In another aspect, provided are promoters isolated from a coffee plant gene that encodes a DIP or PR-5A protein. Preferably, the gene from which the promoter is isolated encodes a DIP protein comprising about 300-400 amino acid residues, or a PR-5A protein comprising about 200-250 amino acids. Various promoters as provided herein comprise one or more regulatory sequences such as a TATA box, an E-box motif (CANNTG), an abscisic acid (ABA)-responsive element (ABRE), a gibberellin-responsive element (GARE), an MYB binding site motif, a GA-1 motif, or an ACGT core-containing motif Preferably, the promoter has a sequence that is highly related to any of SEQ ID NO:2, 3, 6, or 7. Also provided are chimeric genes comprising the promoters, operably-linked to one or more coding sequences. Vectors comprising the nucleic acids, promoters, or chimeric genes are also provided. Also provided herein are cells, especially plant cells, transformed with the vectors, nucleic acids or promoters described. Transformed plant cells of *Coffea* spp., as well as fertile transgenic plants made therefrom are also provided herein.

In yet another aspect, methods of improving one or more quality attributes of a coffee bean are provided. The methods comprise modulating the production of one or more proteins produced in a coffee seed predominantly or exclusively in the late stage of seed maturation. In preferred methods the one or more proteins comprise a DIP or PR-5A protein, and the quality attribute is an aspect of flavor, or aroma, which is improved by using one or more of the nucleic acids, vectors, host cells, or promoters provided herein.

In another of its aspects, the invention provides method of assessing at least one quality attribute of a plant-derived agricultural product, or a batch thereof The methods generally comprise the steps of:

providing a plant-derived agricultural product or batch thereof;

selecting at least two analytes, said analytes including a first analyte, the presence of which is positively-associated with the quality trait, and a second analyte, the presence of which is negatively-associated with the quality the trait;

obtaining sample of the plant-derived agricultural product, or a representative sample of the batch thereof;

determining, directly or indirectly, the relative amounts said first and second analytes in the sample; and assessing the quality trait based on the relative amounts of each of the first and second analytes, or a ratio therebetween.

The methods are generally employed wherein at least one of the analytes is an RNA or a protein. Preferably, at least the first and second analytes are independently RNA or protein, such as DIP or PR-5A protein, and another protein made at a different developmental stage of the plant. Also preferably the plant-derived agricultural product is a seed or seed-derived product. The quality attribute preferably relates to the maturity of the plant, or a plant part from which the agricultural product is derived.

Other and further aspects, features, or advantages of the present invention will be readily apparent to those skilled in the art.

using a primer PRP-F2 GAAGAGAATACATGGACG (SEQ ID NO: 42), designed from the 5' end of pAC7 sequence, and the primer PRP-R2a GCAGATGACGTTAT-GTGTT (SEQ ID NO: 43), designed from the 3' non-coding region of the cDNA. The fragment obtained was 1987 bp and was cloned into pCR4-TOPO. A difference is noted on pAC17-A on CDS 3' region with a new Stop codon TAA generated 68 bases before the stop codon of the clone cccs46w16n19.

Figure 3A:
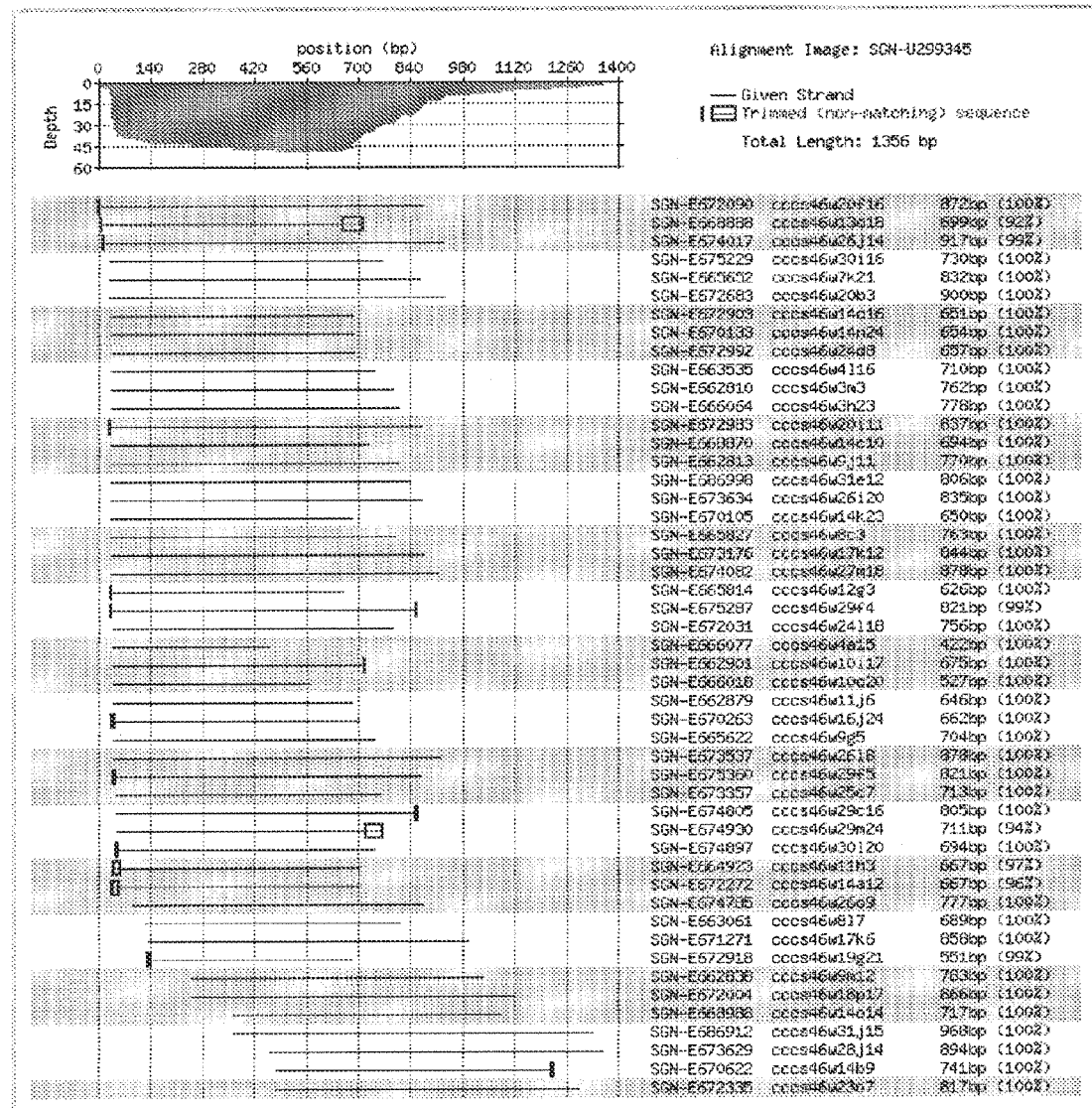

FIG. 3A: EST set for Unigene 124952 (SGN-U299345) for DIP1 gene. The EST set used to generate the in-silico sequence of Unigene 124952 (DIP1) is presented. The cDNA clone cccs46w20f16 was selected for further study.

Figure 3B:
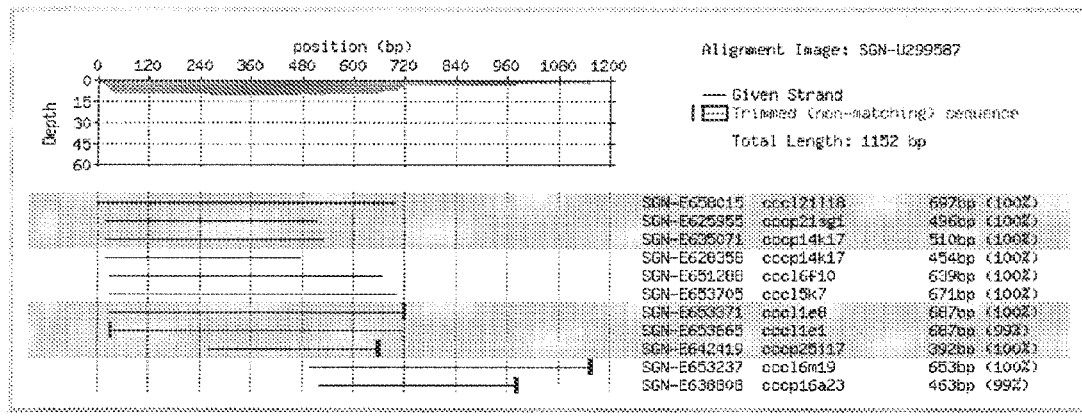

FIG. 3B: EST set for Unigene 121882 (SGN-U299587) for Dip2 gene. The EST set used to generate the in-silico sequence of Unigene 121882 (Dip2) is presented. The cDNA clone cccp21sg1 was selected for further study.

Figure 3C:
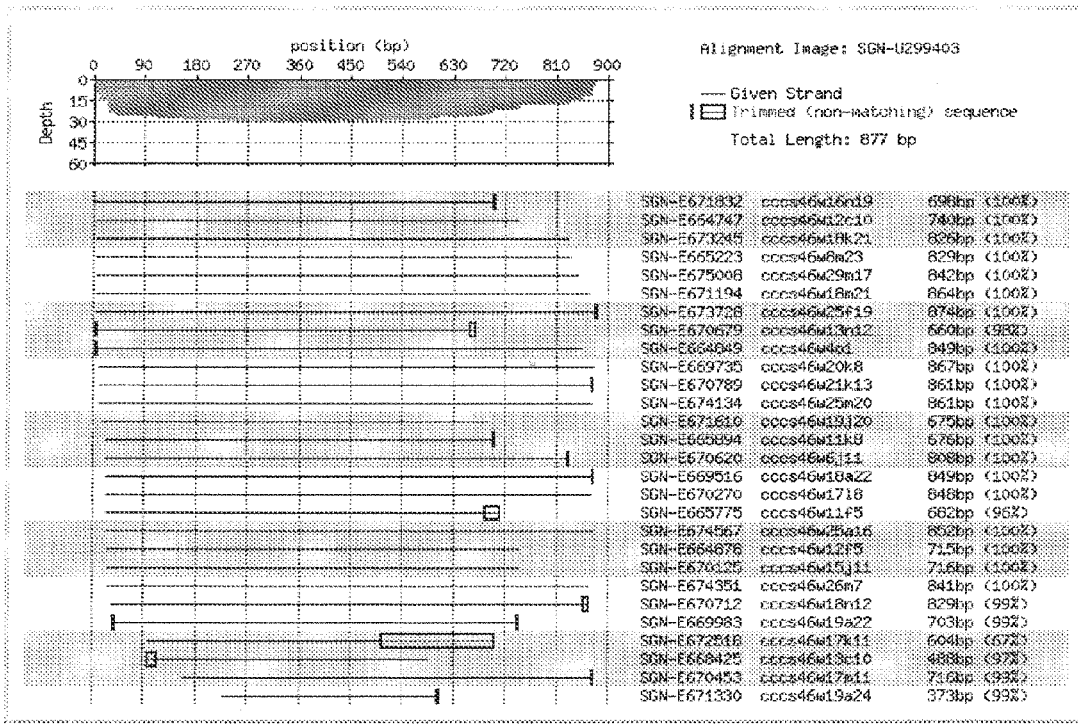

FIG. 3C: EST set for Unigene 119511 (SGN-U299403) for CcPR-5A gene. The EST set used to generate the in-silico sequence of Unigene 119511 (PR-5-A) is presented. The cDNA clone cccs46w16n19 was selected for further study.

FIG. 4: Sequence of the cDNA clone pcccs46w20f16 (Dehydration Induced-Protein 1; DIP1). A) The full length sequence of cDNA clone, pcccs46w20f16 (SEQ ID NO: 8). The ORF is in normal font, with the start and stop codons underlined. The UTR (5' and 3') are shown in italics. Sequences corresponding to the primers and/or probes are boxed in black or grey; B) Sequences of the Taqman probe and primers used for the QRT-PCR experiments; SEQ ID NOs: 15, 16, and 17; C) the primers use to isolate the DIP 1 promoter using "GenomeWalking," SEQ ID NOs: 30 and 31.

FIG. 5: Sequence of the cDNA clone pcccp21sg1 (Dehydration Induced-Protein 2; DIP2). A) The full length sequence of cDNA clone, pcccp21sg1 (SEQ ID NO: 9). The ORF is in normal font, with the start and stop codons underlined. The UTR (5' and 3') are shown in italics. Sequences corresponding to the primers and/or probes are boxed in grey; B) Sequences of the Taqman probe and primers used for the QRT-PCR experiments; SEQ ID NOs: 18, 19, and 20.

FIG. 6: Sequence of the cDNA clone pcccs46w16n19 (Pathogenesis Related protein group 5; PR-5A. A) The full length sequence of cDNA clone, pcccs46W16n19, (SEQ ID NO: 10). The ORF is in normal font, with the start and stop codons underlined. The UTR (5' and 3') are shown in italics. Sequences corresponding to the primers and/or probes are boxed in black or grey; B) Sequences of the Taqman probe and primers used for the QRT-PCR experiments; SEQ ID NOs: 21, 22, and 23; C) the primers use to isolate the PR-S-A promoter using "GenomeWalking," SEQ ID NOs: 51 and 33.

Figure 7:
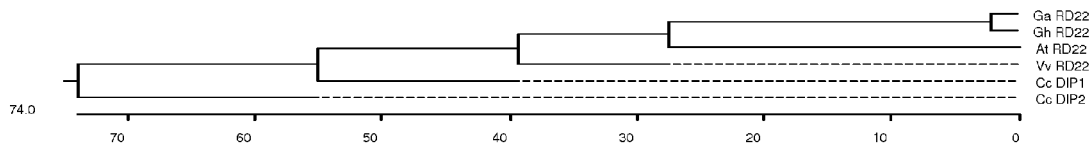

FIG. 7: The alignment of CcDIP1 (clone cccs46w20f16) and CcDIP2 (clone cccp21sg1; unigene CGNU121882) with the closest protein sequences in the NCBI protein database.

FIG. 7A: The sequences were aligned using the Clustal W program in the DNASTAR package, and the alignment was then further optimized manually. The most conserved amino acids are shaded in grey. The BURP-domain is demarcated by black lines, beginning with two FF residues (dotted box). The four CH motifs are boxed with solid double black lines, and the conserved amino acids P, T and W are boxed with single black lines. The tandemly-repeated motifs TXV and VXT are marked by single broken-line boxes, with the motifs specific to DIP1 marked by the double broken-line boxes. The accession numbers of the dehydration-induced protein RD22-like homologues are: *Vitis vinifera* RD22, AY634282 (SEQ ID NO: 44); *Gossypium arboreum* RD22 (RDL2), AY641991 (SEQ ID NO: 45); *Gossypium hirsutum* RD22, AY072821 (SEQ ID NO: 46); and *Arabidopsis thaliana* RD22, AY060560 (SEQ ID NO: 47).

FIG. 7B: A rooted phylogenetic tree was produced from the optimized alignment using the Megalign program of DNAS-TAR (see the Megalign program for details).

Figure 8:
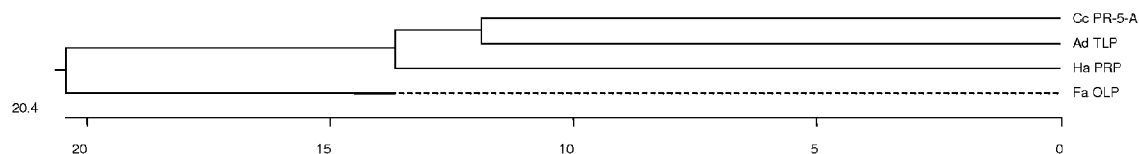

FIG. 8: The alignment of CcPR-5A (clone cccs46w16n19; unigene CGN-U119511) with the closest protein sequences in the NCBI protein database.

FIG. 8A: The sequences were aligned using the Clustal W program in the DNASTAR package, and then this alignment was further optimized manually. The most conserved amino acids are shaded in grey. Each of the 16 conserved cysteines are boxed in black and the motif found in thaumatin-related proteins is demarcated by the broken-line box.

FIG. 8B: A rooted phylogenetic tree was produced from the optimized alignment using the Megalign program of DNAS-TAR (see the Megalign program for details). The accession numbers of the PR-5A-like homologues are: AdTLP, thaumatin-like protein from *Actinidia deliciosa* (AJ871175) (SEQ ID NO: 48); HaPRP, pathogenesis-related protein from *Helianthus annuus* (AF364864) (SEQ ID NO: 49); and FaOLP, osmotin-like protein from *Fragaria×ananassa* (AF199508) (SEQ ID NO: 50).

Figure 9:
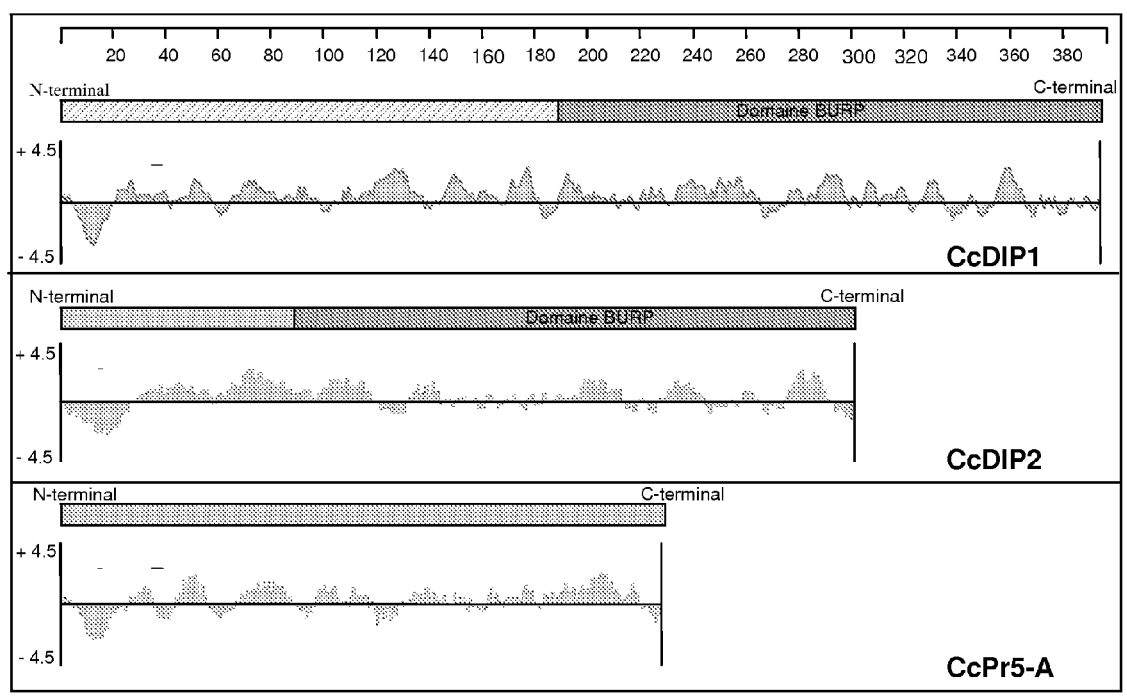

FIG. 9: Hydrophobicity profiles of CcDIP1, CcDIP2 et CcPR-5-A. The profiles were obtained using the method of Kyte-Doolittle program in the LASERGENE software package (DNASTAR). Negative values correspond to hydrophobicity. The N-terminal sequences of the three proteins are very hydrophobic and probably correspond to signal peptides. The remaining polypeptide sequences are primarily hydrophilic.

FIG. 10: In silico sequence of DIP1 promoter and coding sequences from *Coffea arabica* L. cv Caturra (T2308), deduced from the sequences of pAS22, pAC1, and pcccs46w20f16. The 5'region of Dip1 promoter in the plasmid pAS22 is boxed in Black CAPS, the 3' region of Dip1 promoter, which comes from the plasmid pAC1, is indicated in ITALIC CAPS, the 5' and 3' non-coding regions of pAC1 are in surrounded by the broken-line box, and the Dip1 protein coding sequence and introns of pAC1 are in CAPS (protein sequences in CAPS, intron sequences in lower case letters, and putative splice signals are underscored). The end of the 3' non-coding region sequence comes from pcccs46w20f16 and is indicated in ITALIC CAPS. The nucleotide differences between the sequences of AS22 and pAC1 are noted in the pAC1 sequence are in BOLD CAPS. The sequence of the pAC1 plasmid was amplified from genomic DNA of *Coffea arabica* T2308 with forward primer DipAC1 F gtcagccacattaagagcagg (SEQ ID NO: 38) and reverse primer gggcaagcatttggagtttc (SEQ ID NO: 39) (in lower case italics, shaded in grey box). The start codon and the stop codon of the protein sequence are marked with an asterisk. Note: The primers forward Dip1A F5 GAACAATTTTC-TATTTGGTG (SEQ ID NO: 36) and reverse Dip1A R5 TAGCTTTCGGCATAGGAC (SEQ ID NO: 37) (in shaded grey boxes in CAPS) were also useful for this sequence.

FIG. 11: The promoter sequence of CcDIP 1. The DIP 1 promoter sequence was amplified with primers Dip1A F5 and Dip1A R5 from *Coffea arabica* (T2308) genomic DNA and then cloned into pCR4-TOPO to give pAS22. This sequence was analysed using the PLACE Web Signal Scan program (http://www.dna.affrc.go.jp/PLACE/signalscan.html). The sequence in ITALIC CAPS corresponds to the UTR cDNA sequence from pcccs46w20f16 (starting with underlined ATG), the sequence in bold corresponds to the 5' sequence of the CcDip1 gene (intron in lowercase). The sequence in CAPS upstream of the ITALIC CAPS is upstream promoter sequence. The putative "TATA-box" is in underlined, and various transcription factor motifs found are shown (e.g. E-boxes (double-line boxes), MYB (bold-line boxes), ABRE (broken line boxes), GARE (zigzag box), and GA-1 (black single line box)).

Figure 12B:
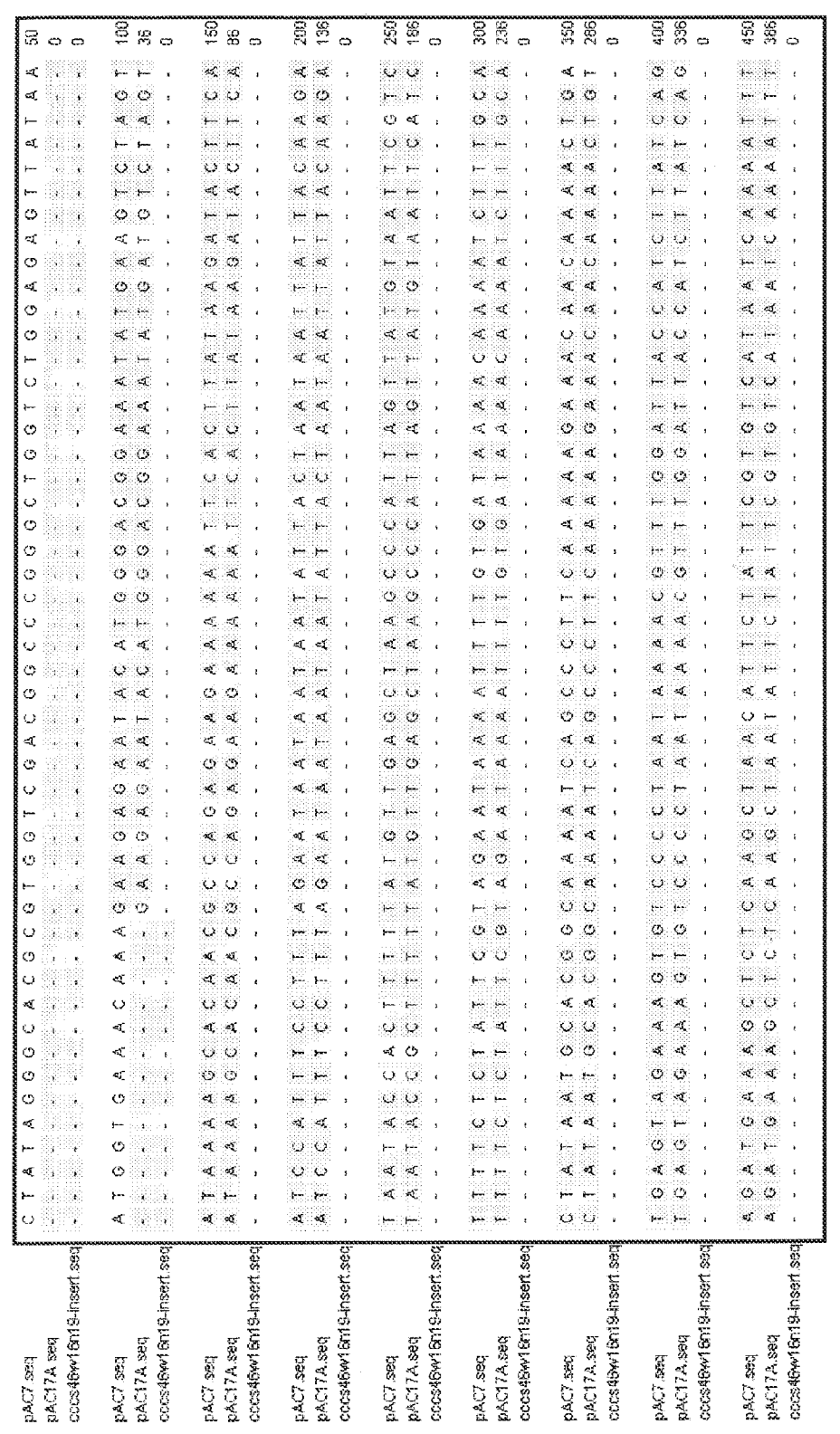
Figure 12C:
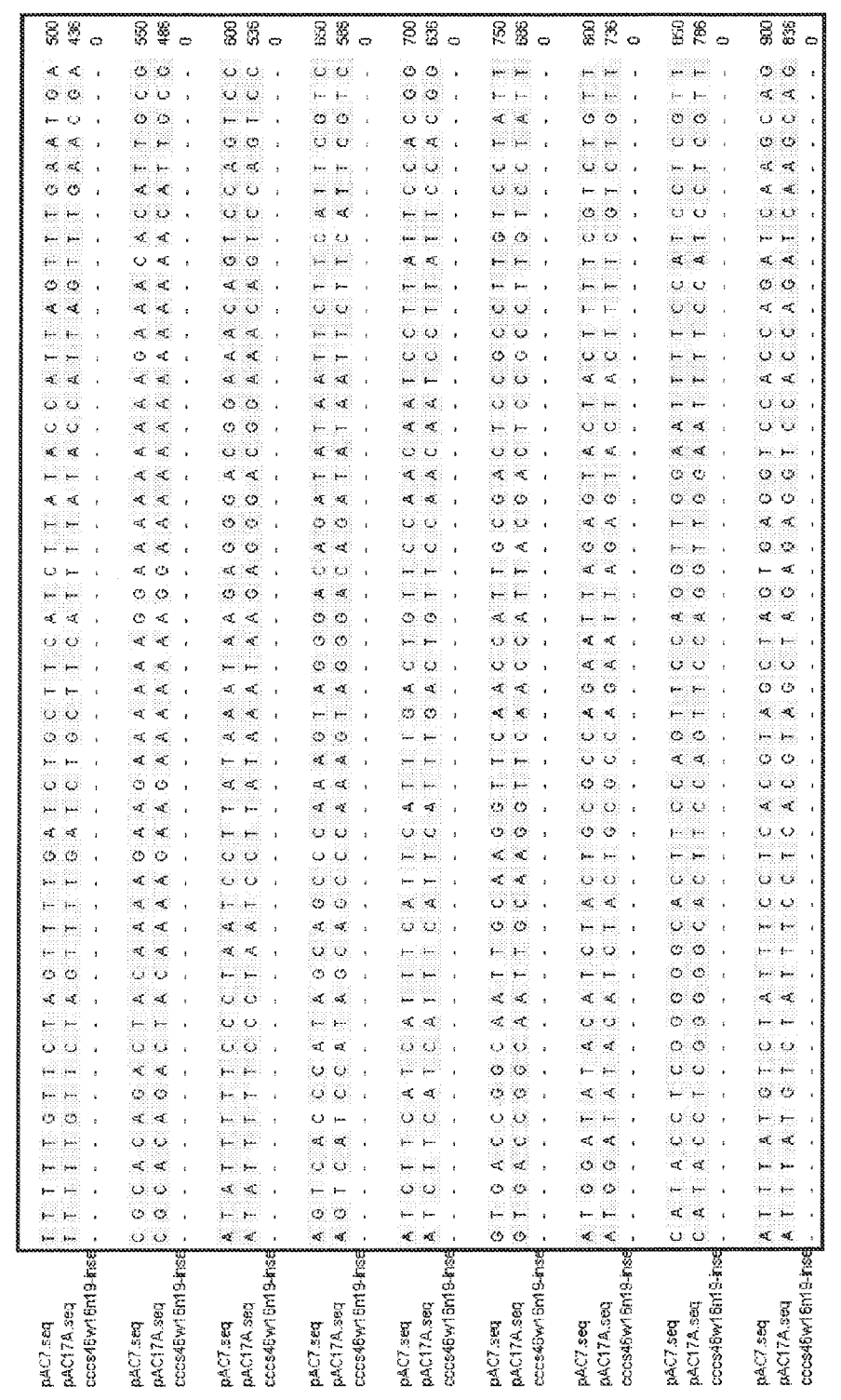
Figure 12D:
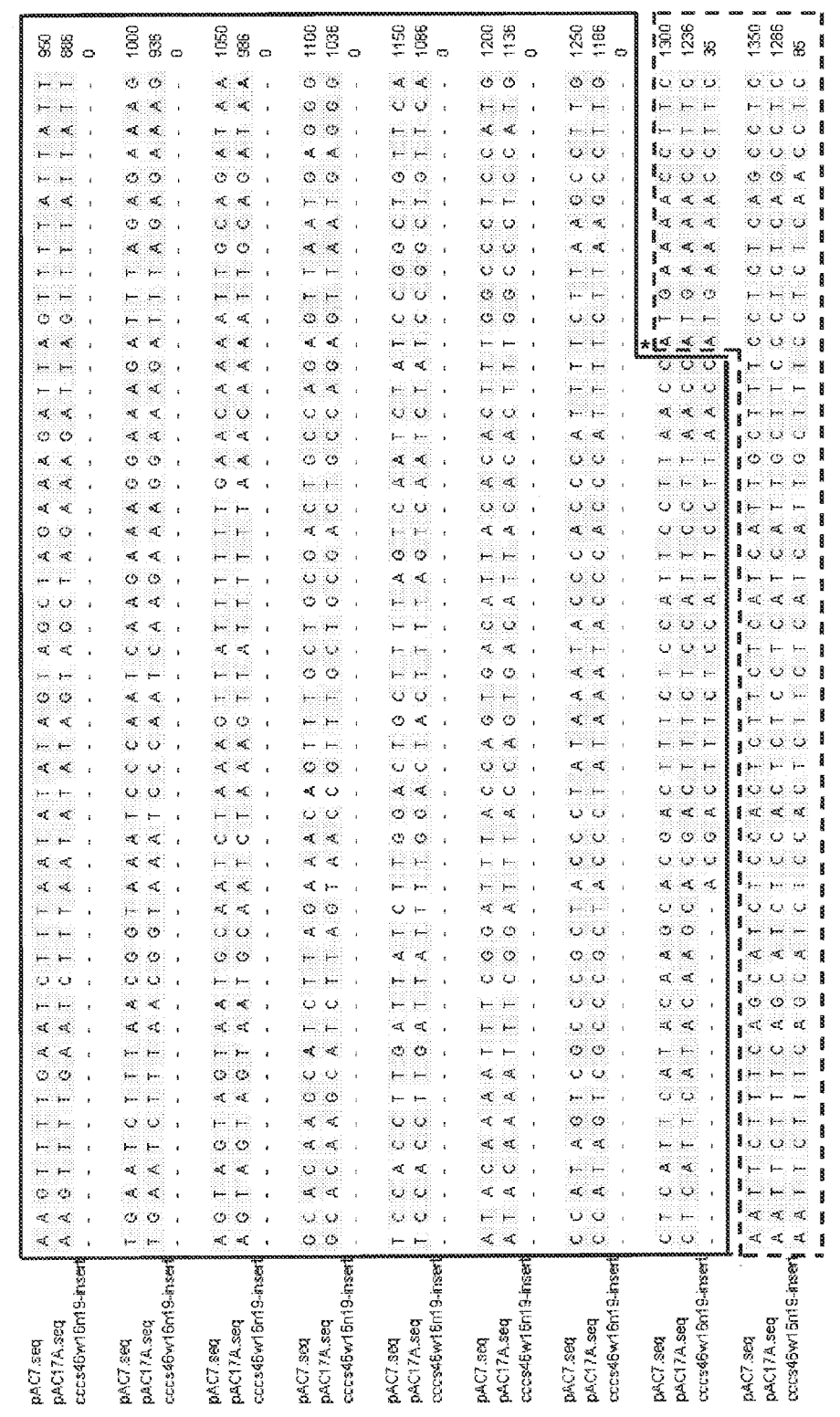
Figure 12E:
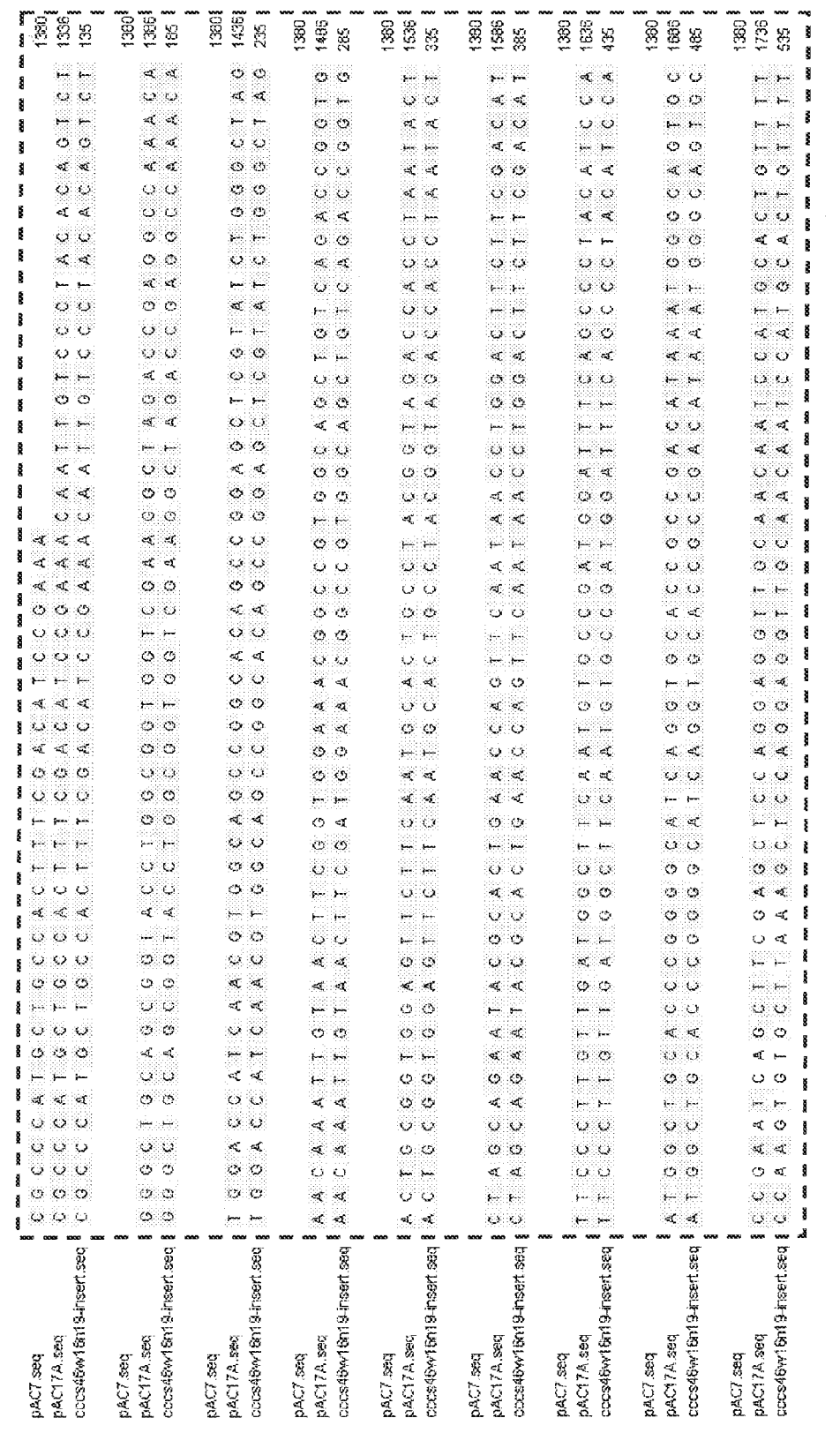
Figure 12F:
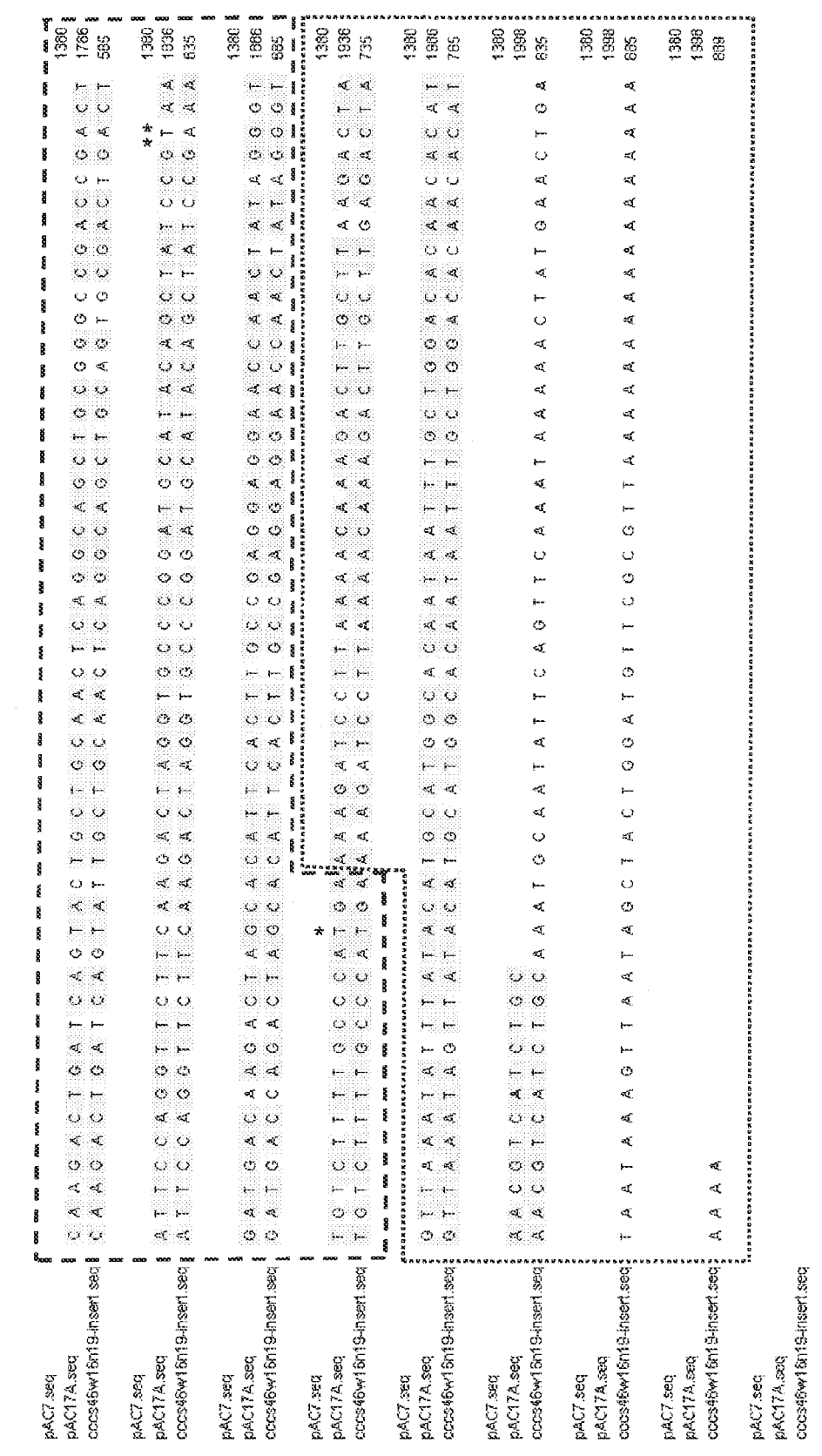

FIG. 12A: Sequence of pPR-5A promoter and coding sequence from *Coffea arabica* L.cv Caturra (T2308) cloned in pAC17-A. The remaining promoter sequence and the coding sequence of pPR-5-A is from the plasmid pAC17-A, with the promoter region shown in regular CAPS in the black box, and the coding sequence shown downstream of the start codon (*ATG marked with an asterisk). The insert of pAC17-A was amplified from genomic DNA from *Coffea arabica* T2308 with the forward primer PRP-F2 GAAGAGAATACATGG-GACG (SEQ ID NO: 42) and reverse primer PRP-R2a GCA-GATGACGTTATGTGTT (SEQ ID NO: 43) (shaded in black (inverse)). The start and stop codons are marked with asterisks. The sequence of pAC17-A showed a difference from the sequence of the pcccs46W16n19 clone on the CDS 3' region, with a new Stop codon (TAA) generated 66 bases before the TGA stop codon of the clone pcccs46w16n19.

FIGS. 12B, 12C, 12D, 12E and 12F: Alignment of the sequence of pAC7, pAC17-A and pcccs46w16n19. The sequences were aligned using the Clustal V program in the DNASTAR package. The promoter region is shown in the solid-line box, the coding sequence is boxed with a broken-line, and the 3' non-coding region is boxed with a dotted line. The start and stop codons are each marked with an asterisk. The sequence of pAC17-A showed a difference from the sequence of the pcccs46w16n19 clone on the CDS 3' region, with a new Stop codon (*TAA) generated 66 bases before the stop codon (*TGA) of the clone pcccs46w16n19.

FIG. 13: The promoter sequence of CcPR-5-A. The pPR-5-A promoter sequence in pAC7 plasmid was analysed using the PLACE Web Signal Scan program (http://www.dna.af-frc.go.jp/PLACE/signalscan.html). The sequence in normal CAPS corresponds to the 5' UTR of the cDNA sequence in pcccs46w16n19 (starting ATG underlined), the sequence in BOLD CAPS correspond to the CcPR-5-A gene. The sequence in black is the upstream promoter sequence. The putative "TATA-box" is boxed with a bold black line, and various transcription factor motifs found are noted as in previous figures. The sequences shaded in gray correspond to the primers used, 5' AP2 GW, and Primer GSP2 119511.

Figure 14:
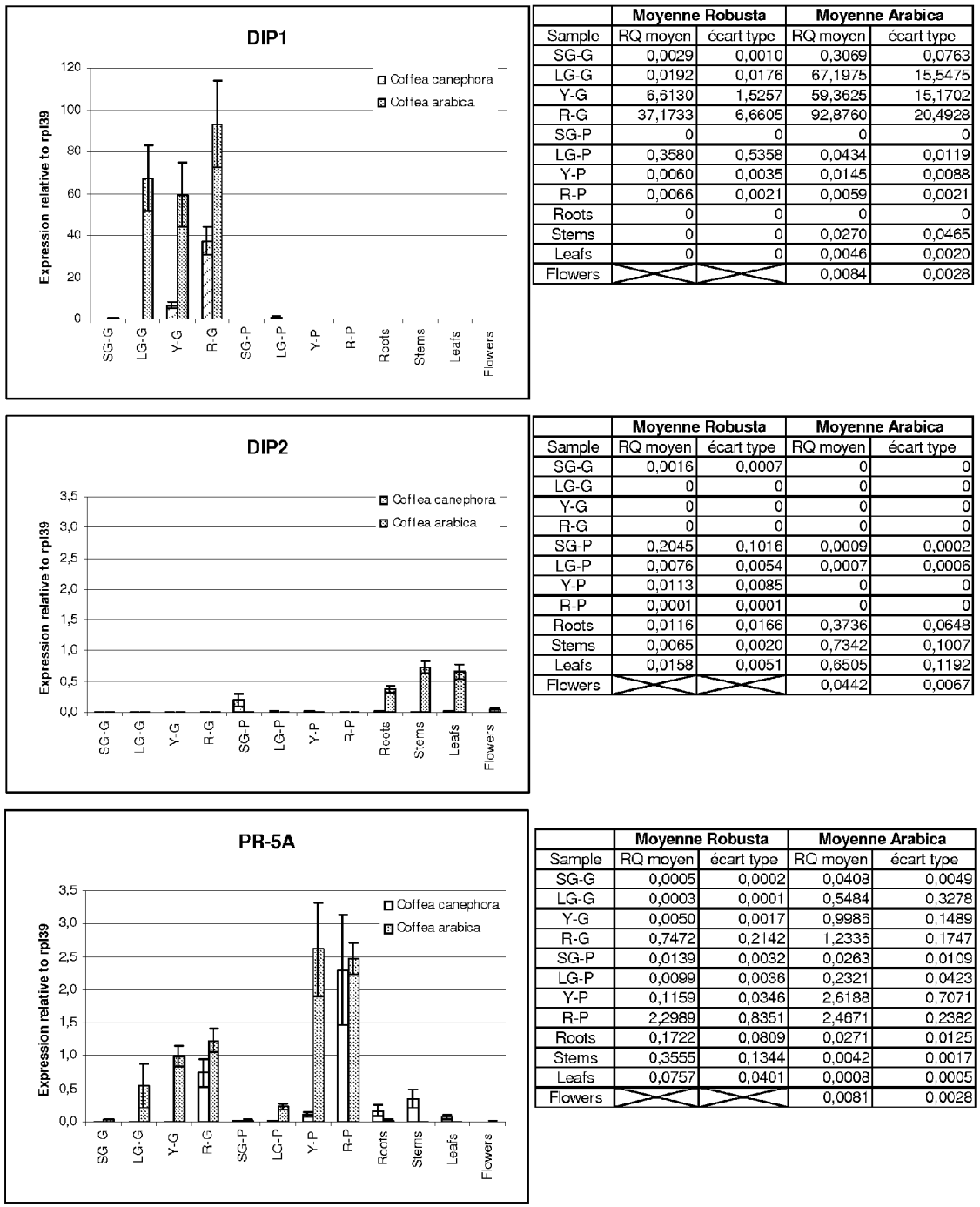

FIG. 14: Relative expression levels for CcDIP1, CcDIP2 and CcPR-5-A in different tissues of *Coffea canephora* and *Coffea arabica*. Quantitative RT-PCR was carried out as described in the methods to determine the relative expression (RQ) for each gene in relation to the expression of a constitutively expressed gene (ribosomal protein CcRPL39). The tissues tested included: SG-G, small green grain; LG-G, large green grain; Y-G, yellow grain; R-G red grain; SG-P, small green pericarp; LG-P, large green pericarp; Y-P, yellow pericarp; R-P, red pericarp; roots, stems, leaves, and flowers from *Coffea arabica* T2308 and *Coffea canephora* BP409. The values given for each sample are an average of two or three independent experiments using the same cDNA sample, with three replicates for each sample. The expression was not tested for *C. canephora* flowers. FIG. 14A, DIP1; FIG. 14B, DIP2; FIG. 14C, PR-5A.

Figure 15:
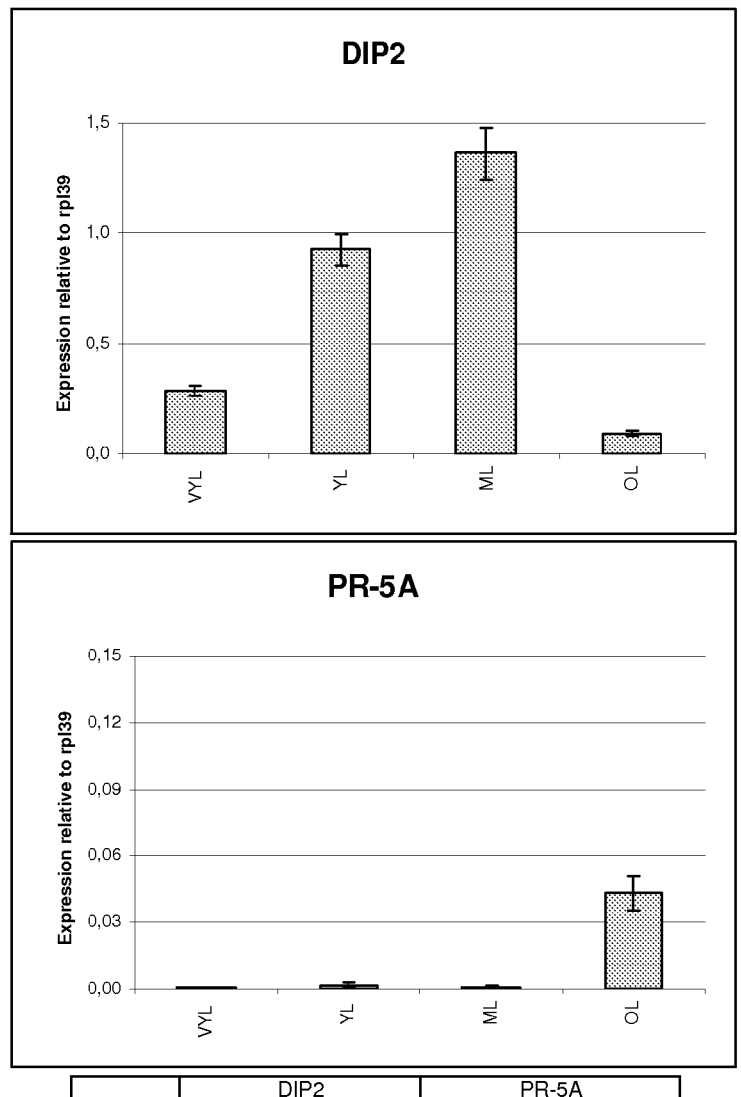

FIG. 15: Relative expression levels for CcDIP2 and CcPR-5-A during different stages of leaf development for *Coffea arabica* (T-2308). Quantitative RT-PCR was carried out to determine the relative expression (RQ) level of each gene versus the ribosomal protein CcRPL39. VYL, very young leaves; YL, young leaves; ML, mature leaves; OL, old leaves. FIG. 15A, DIP2; FIG. 15B, PR-5A.

Figure 16:
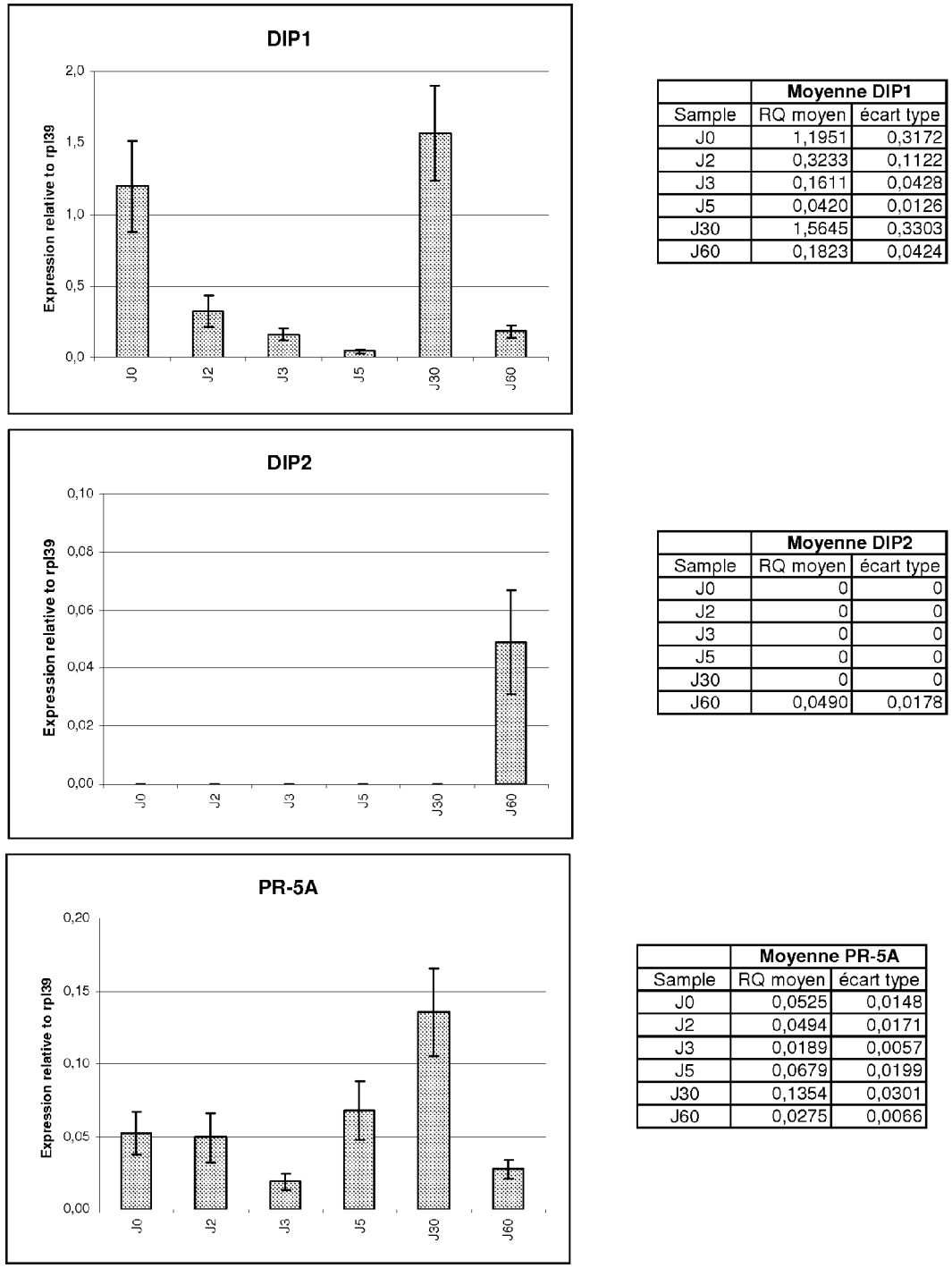

FIG. 16: Relative expression levels for CcDIP1, CcDIP2 and CcPR-5-A during germination for *Coffea arabica* (T-2308). Quantitative RT-PCR was carried out to determine the expression level of each gene relative to the expression level of a constitutively expressed gene CcRPL39. The germination samples were prepared, and RNA purified as described in the methods. J0 (was taken after rinsing grain with water); Samples J2, J3, J5, J30, and J60, represent 2, 3, 5, 30 and 60 days of germination. FIG. 16A, DIP1; FIG. 16B, DIP2; FIG. 16C, PR-5A.

Figure 17:
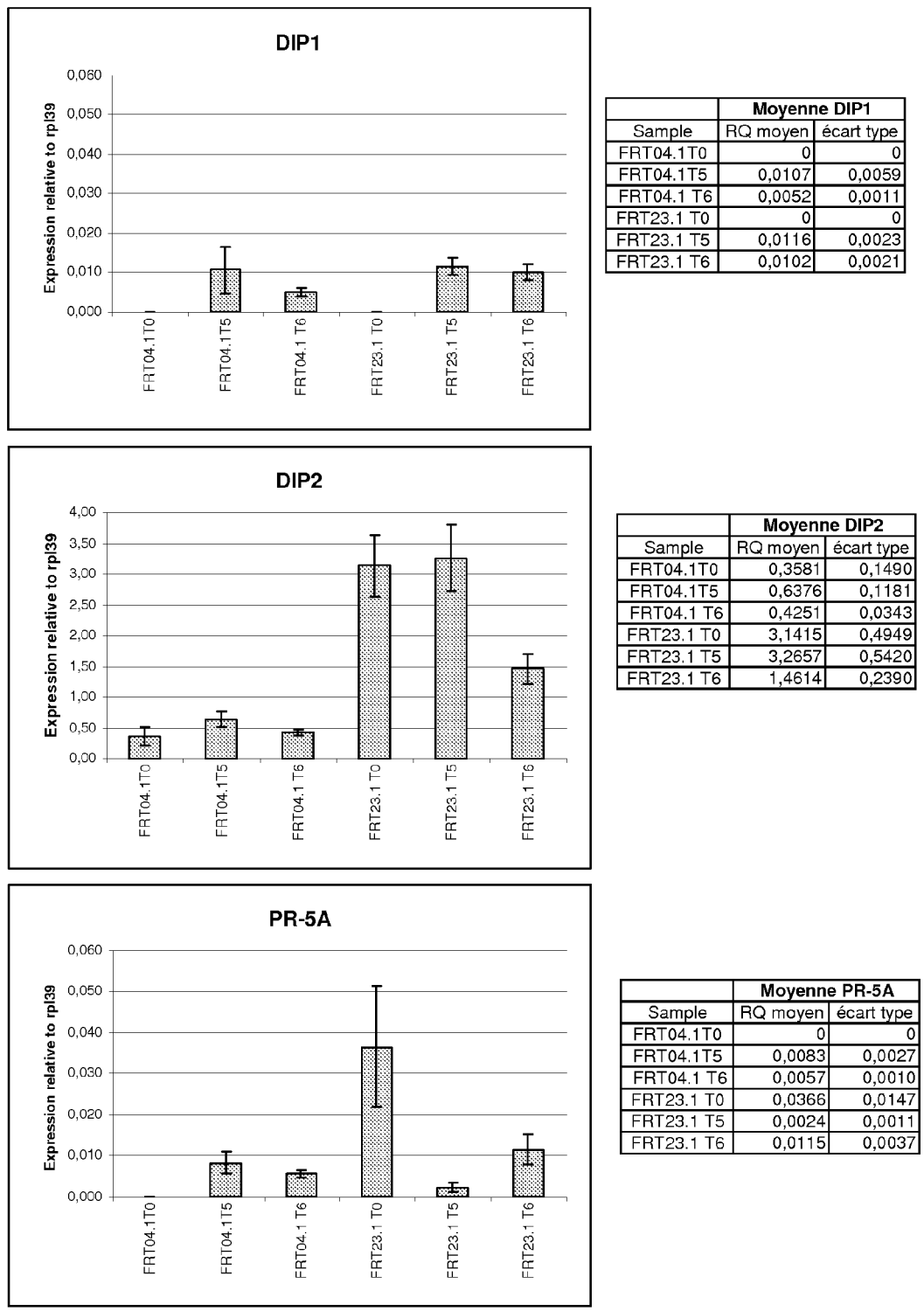

FIG. 17: Relative expression levels for CcDIP1, CcDIP2 and CcPR-5-A in leaves of two small trees of *Coffea canephora* genotypes FRT04 and FRT23 subjected to water stress. Quantitative RT-PCR was carried out to determine the relative expression level of each gene during different levels of water stress versus the expression level of gene CcRPL39). T0 represents a sample taken before watering was stopped; T5 and T6 represent samples taken 5 and 6 weeks after watering was stopped. FIG. 17A, DIP1; FIG. 17B, DIP2; FIG. 17C, PR-5A.

Figure 18:
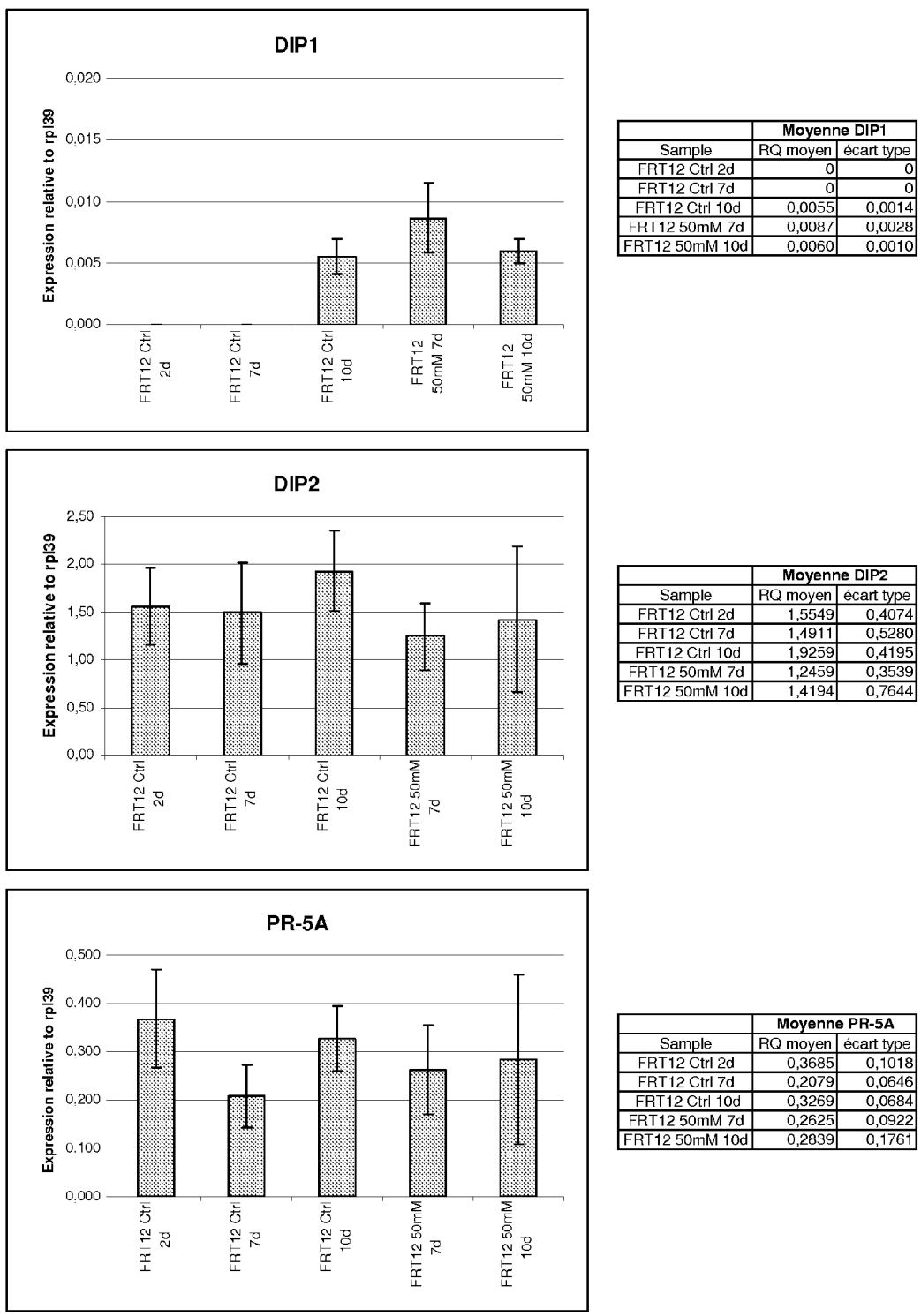

FIG. 18: Relative expression levels for CcDIP1, CcDIP2 and CcPR-5-A in microcuttings of *Coffea canephora* genotype FRT12 under salt stress. Quantitative RTPCR was carried out to determine the relative expression (RQ) of each gene in microcuttings placed on B0,3 medium and an additional 50 mM NaCl. RQ (relative expression) was determined versus CcRPL39 expression. The samples were taken at 2, 7, and 10 days after treatment. The control microcuttings were grown at the same time but transferred to BQ3 medium (without NaCl). FIG. 18A, DIP1; FIG. 18B, DIP2; FIG. 18C, PR-5A.

Figure 19:
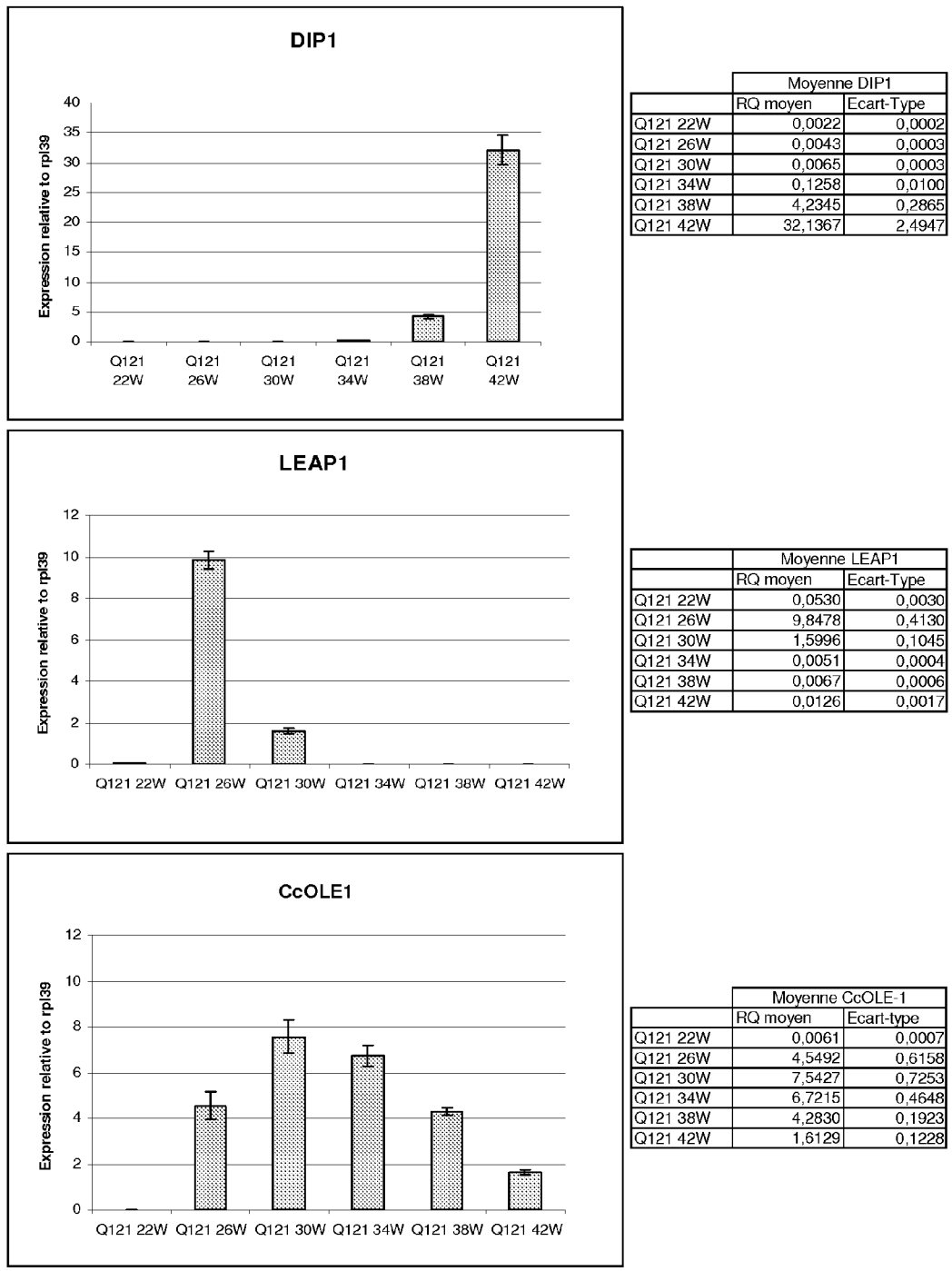

FIG. 19: Relative expression levels of DIP1, LEAP1, and OLE1 in the developing grain of *C. canephora* genotype Q121. The relative expression (RQ) of each gene was measured for grain at different stages of development using quantitative RT-PCR. The RQ was determined versus CcRPL39 expression. RNA was extracted from the grain of cherries harvested at 22, 26, 30, 34, 36, and 42 weeks after flowering. FIG. 19A, DIP1; FIG. 19B, DIP2; FIG. 19C, PR-5A.

FIG. 20: Evaluation of DIP1, LEAP1, and OLE1 transcript representation in samples of premixed cDNA using quantitative PCR. Different percentages of the RNA from immature grain (e.g., 26-week or 30-week) and mature grain (e.g., 42-week), as used in FIG. 18, were mixed. The relative expression of DIP1, LEAP1 and OLE1 were measured in the mixed samples using quantitative RT-PCR. RQ was determined versus CcRPL39 expression. The Q121 immature/mature mixes were 5/95, 10/90, 20/80, and 50/50 percent, respectively. FIG. 20A, immature=26-week; FIG. 20B, immature=30-week.

Figure 21:
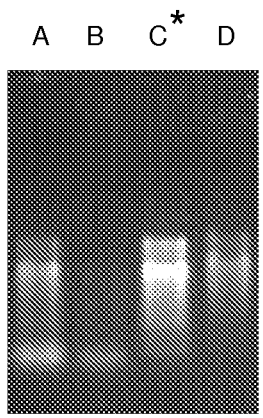

FIG. 21: Agarose gel electrophoresis of total RNA extracted from stored green coffee grain of mature *C. canephora* FRT09 fruit. RNA extractions were made from four separate samples of one lot of stored *C. canephora* FRT09 green grain and then run on an RNA gel. The lanes contained the following samples: Lane A, 11-RNA-FRT09-H1, Lane B, 13-RNA-FRT09-H2, Lane C, 12-RNA-FRT09-H3, and Lane D, 13-RNA-FRT09-2005. The sample from Lane C, marked with an *, was chosen for cDNA production and QPCR experiments.

Figure 22:
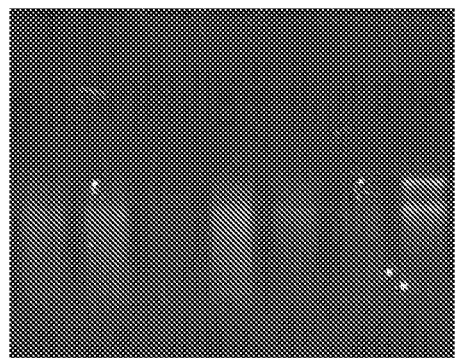

FIG. 22: Total RNA from dry green grain of six different *C. canephora* varieties stored at ambient temperature for over one year. Mature red fruit were harvested at a coffee farm in Ecuador. The fruit was dry processed, transported, and stored as described for the samples in FIG. 11. RNA samples in water (5 μl) were added to 10 μl of RNA sample-loading buffer (Sigma, R1386) and heated at 65° C. for 15 min. The lanes contained the following samples: Lane E, *C. canephora* FRT 07 (RNA-Maturity 1-FRT07-A); Lane F, *C. canephora* FRT 17 (RNA-Maturity 1-FRT17-A); Lane G, *C. canephora* FRT 28 (RNA-Maturity 1-FRT28-A); Lane H, *C. canephora* FRT 49 (RNA-Maturity 1-FRT49-A); Lane I, *C. canephora* FRT 53 (RNA-Maturity 1-FRT53-A); Lane J, *C. canephora* FRT 72 (RNA-Maturity 1-FRT72-A); Lane K, control RNA (RNA-Maturity 1-BP 358 42W) sample from *C. canephora* BP 358 cherries harvested at 42 weeks after fertilization and stored at −80° C. (from ICCRI farm). The samples from Lanes H, I, and K (each marked with *) were used in the QRT-PCR experiments.

Figure 23:
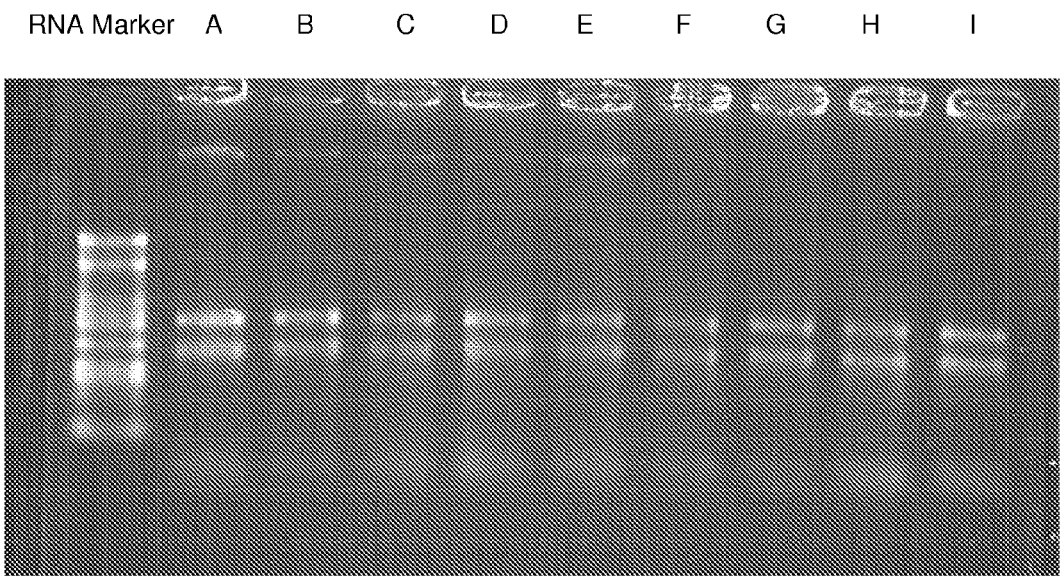

FIG. 23: Agarose gel electrophoresis of total RNA from mature coffee seeds of *C. arabica*, and *C. canephora*.

Lanes A, B, C, D and E: are control fresh mature red-skin seeds from *C. arabica* T2308 harvested in the green house and processed immediately. Lane A: T2308 frozen at harvest time, depulped frozen; Lane B: T2308 washed and frozen at harvest time; Lane C: T2308 washed and dry for 1 day at 45° C., then frozen; Lane D: T2308 washed and dry for 5 days at 45° C., then frozen; Lane E: T2308 washed and dry for 7 days at 45° C., then frozen.

Lanes F, G, H, and I: are grain harvested in Ecuador, processed, dried, and stored at room temperature at the laboratory for 1 year. Lane F: *C. arabica* CCA 12; Lane G: *C. arabica* CCA 21; Lane H: *C. canephora* FRT 09; Lane I: *C. canephora* FRT 63.

Figure 24:
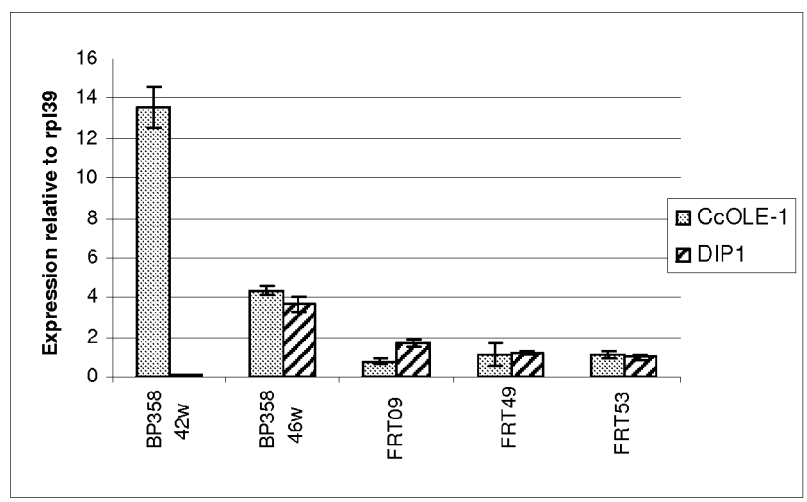

FIG. 24: Comparison of the transcript levels of DIP1 and OLE1 in various grain samples. Quantitative RT-PCR was used to determine the relative transcript levels for the OLE1 and DIP1 genes in RNA isolated from three different dry-stored *C. canephora* green grain samples. For comparative purposes, the transcript levels found in freshly-frozen grain samples of *C. canephora* BP358 at two different developmental stages were also determined (whole cherries stored frozen at −80° C.). Total RNA isolation and cDNA production are described in the materials and methods. Relative expression (RQ) was determined versus CcRPL39 expression. RNA samples corresponding to the fresh-frozen samples were from *C. canephora* BP358 cherries harvested at 42 and 46 weeks, respectively, after fertilization; RNA samples corresponding to the mature dry green grain samples stored at ambient temperature for 1 year were from *C. canephora* FRT 09, FRT 49, and FRT 53, respectively.

Figure 25:
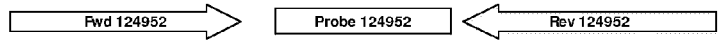

FIG. 25: Primers and probe positions for QRT-PCR for CcDIP1 cDNA. Arrows indicate the sequences corresponding to the forward and reverse primers, Fwd 124592, Sonde MGB952, Rev. 124952.

Figures 26, 27:
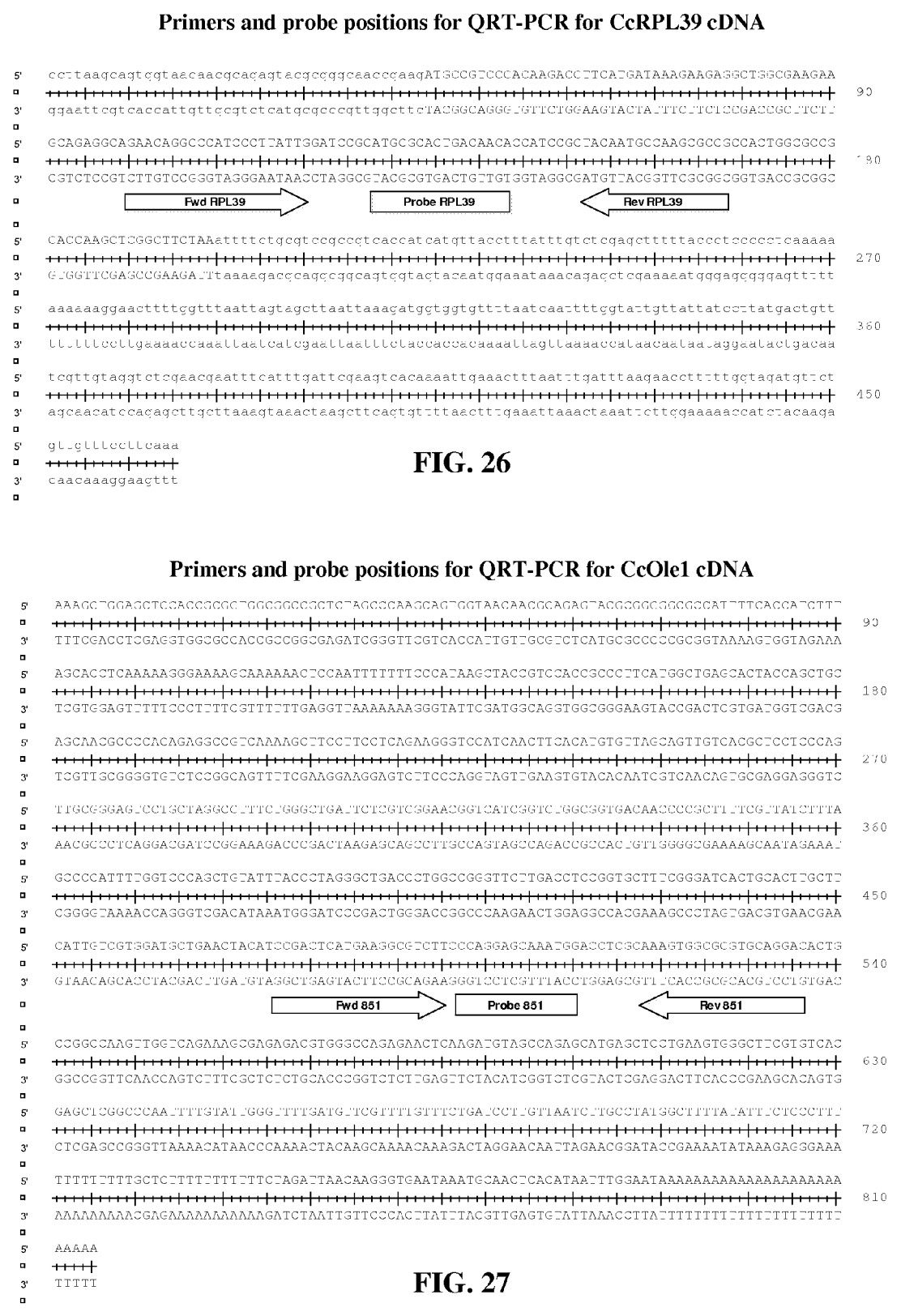

FIG. 26: Primers and probe positions for QRT-PCR for CcRPL39 cDNA. Arrows indicate the sequences corresponding to the forward and reverse primers, Rpl 39 F, Rpl 39 R, Sonde MGB Rpl39.

FIG. 27: Primers and probe positions for QRT-PCR for CcO1c1 cDNA. Arrows indicate the sequences corresponding to the forward and reverse primers, Fwd851, Sonde MGB851, Rev. 851.

Figure 28:
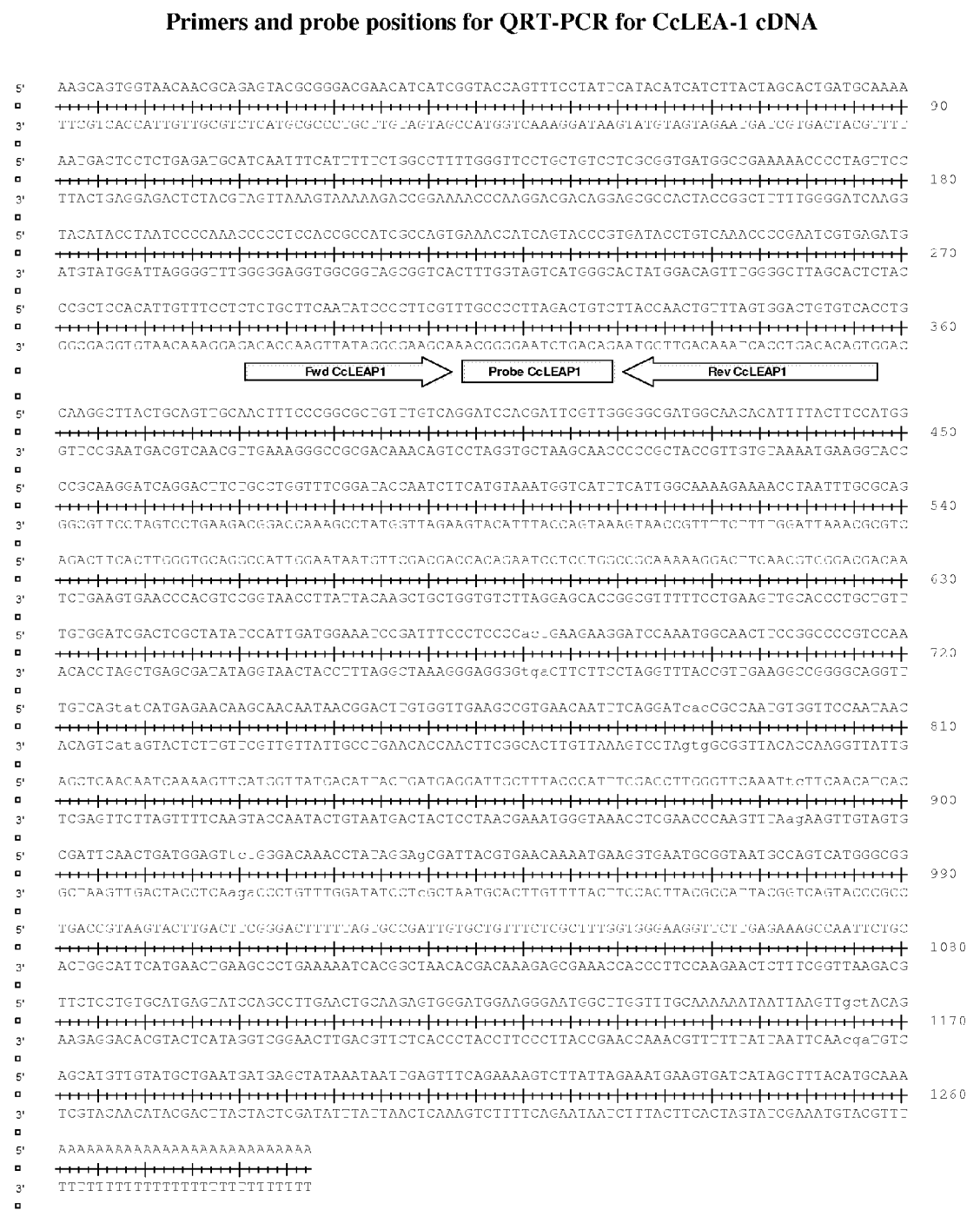

FIG. 28: Primers and probe positions for QRT-PCR for CcLEA-1 cDNA. Arrows indicate the sequences corresponding to the forward and reverse primers, CcLEAP1 F1, Sonde MGB, CcLEAP1 R1.

Figure 29:
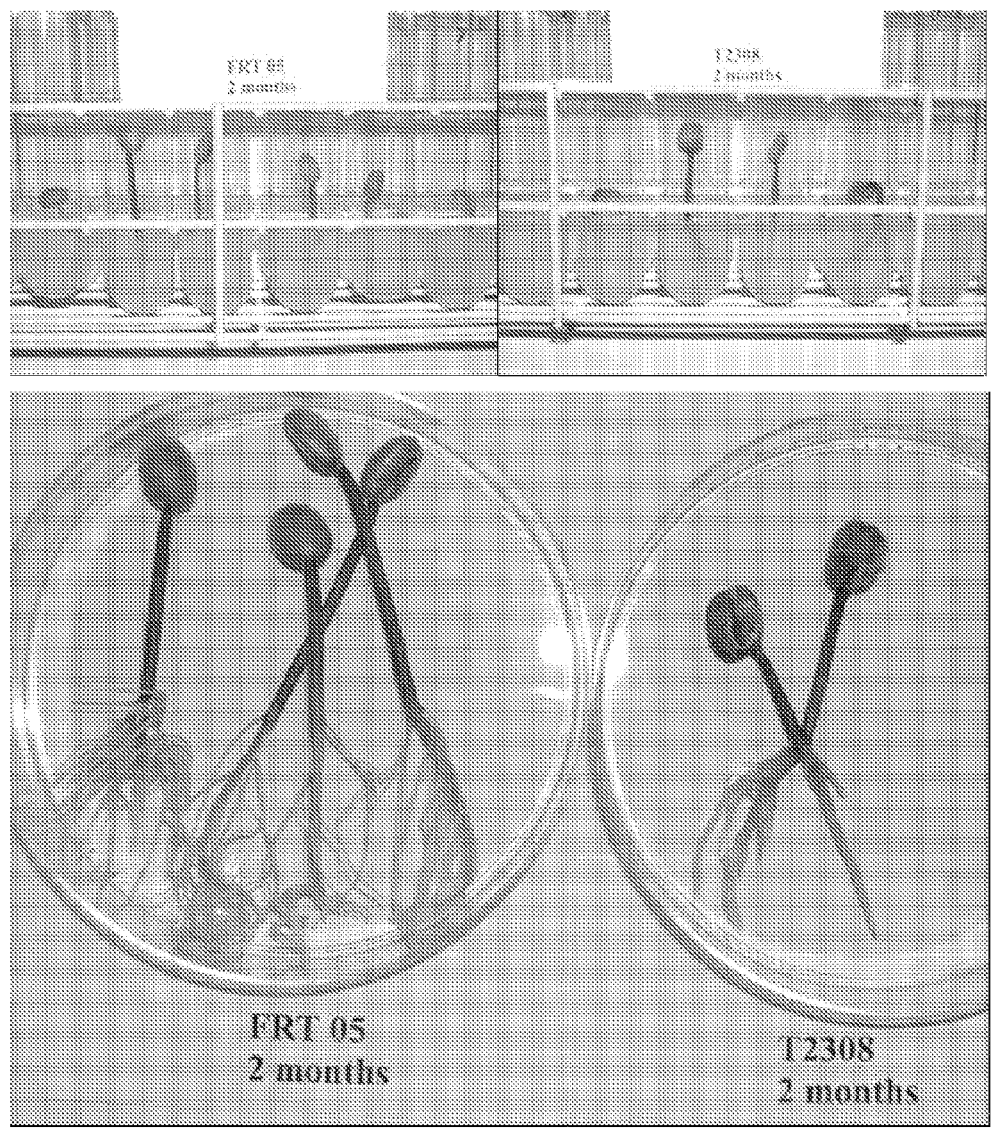

FIG. 29: Figure of germinating seeds of *Coffea arabica* cv. Caturra (T2308) and *Coffea canephora* cv Robusta (FRT05) two months after in vitro sowing. The heterogeneity of the seed development, as well as significant arabica versus robusta root development can be seen. For the expression experiment, only the most developed seedlings for each specific period were taken for RNA extraction.

DETAILED DESCRIPTION OF THE INVENTION

Definitions

Various terms relating to the biological molecules and other aspects of the present invention are used throughout the specification and claims.

"Dehydration-induced proteins" or "DIPs" are a group of proteins comprising one or more structural features in common with a group of other proteins, some of which have been associated with dehydration stress in plants. Such structural features may include, but are not limited to one or more BURP domains, particularly a C-terminal BURP domain; conserved FF motif, particularly within a BURP domain, one or more conserved CH motifs also preferably within a BURP domain; motifs TXV and/or VXT, preferably in one or more tandem repeats; a signal peptide, and a largely hydrophilic (mature) protein sequence. DIP proteins are preferably about 300-400 amino acid residues in length, and phylogenetically-related to dehydration-induced protein RD22-like homologues including *Vitis vinifera* RD22, *Gossypium arboreum* RD22 (RDL2), *Gossypium hirsutum* RD22, and *Arabidopsis thaliana* RD22 (GenBank Accession Numbers AY634282, AY641991, AY072821, and AY060560, respectively) (SEQ ID NOs: 44, 45, 46, 47, respectively). Notwithstanding the name "dehydration-induced protein," there is nothing inherent in a DIP protein that requires that it is necessarily induced under water stress, drought stress, osmotic stress, or by any other specific stressors or conditions.

"Pathogenesis-related proteins" or "PR" proteins are a group of proteins comprising one or more structural features in common with a group of other proteins, some of which have been associated with responses to pathogens, for example, fungal pathogens, or osmotic stress in plants. Such structural features may include, but are not limited to one or more thaumatin domains (or "thaumatin motifs") found in thaumatin-related proteins; one or more (up to 16 or more) conserved cysteine residues throughout the protein; a signal peptide, and a largely hydrophilic (mature) protein sequence. The PR proteins of the invention are preferably about 200-250 amino acid residues in length and phylogenetically-related to PR-5A-like homologues including AdTLP, thaumatin-like protein from *Actinidia deliciosa*, HaPRP, pathogenesis-related protein from *Helianthus annuus*, and FaOLP, osmotin-like protein from *Fragaria×ananassa* (GenBank Accession Numbers AJ871175, AF364864, and AF199508, respectively) (SEQ ID NOs: 48-50, respectively). Notwithstanding the name "pathogenesis-related protein," there is nothing inherent in a PR protein that requires that it is necessarily induced in response to a pathogen invasion or infection, by exposure to any pathogen, nor by water-, drought-, or osmotic-stress or any other specific conditions or stressors.

As used herein, the "late stage of maturation" refers a time period during which biological changes associated with the maturation of a seed or grain take place, and after which the seed or grain is considered "mature." After maturation, seeds typically have low moisture content, reduced metabolic activity including respiration, and have adapted to survive severe conditions through the accumulation of certain protective compounds. The seed maturation process frequently includes metabolic changes such as the final accumulation of storage products, the induction of dormancy and/or the suppression of precocious germination, and other changes (see, e.g., Bewley and Black, 1994). These metabolic changes are also reflected in many changes in gene expression within seeds during maturation. Thus, in some seeds, maturation is characterized by expression of certain known seed maturation genes, such as late-embryogenesis abundant or storage-compound genes. In some cases, seed becomes competent for reproduction only during or after the last stage. Although actually a complex physiological or biological process, the stages of seed maturation are conveniently frequently described to include a first stage, morphological development, which features the formation of the embryo, followed by a second, or cell expansion stage, during which food reserves are produced and accumulated. The last stage of maturation features seed dehydration and is characterized by a decrease in the water weight and fresh weight of the seed, and a steady increase in the dry weight of the seed. Seeds become quiescent at desiccation and can often be stored for a long time thereafter, in some cases without substantial loss of viability. Mature seeds that are adequately desiccated are frequently resistant to many pathogens.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide", also referred to as "nucleic acid" or "nucleic acid molecule", generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini.

It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for Protein Modifications and Nonprotein Cofactors", *Meth. Enzymol.* (1990) 182:626-646 and Rattan et al., "Protein Synthesis: Posttranslational Modifications and Aging", *Ann NY Acad. Sci.* (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e., the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, *J. Theor. Biol.* 119:205). When referring to nucleic acid molecules, "percent identical" refers to the percent of the nucleotides of the subject nucleic acid sequence that have been matched to identical nucleotides by a sequence analysis program.

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', F(ab')2 and Fv), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y. (1988), Chapter 6.

The term "substantially" means more than half and more preferably, more than two-thirds, or three-quarters, more preferably it means at least 80 or 90%, 95%, 99%, or greater.

"Substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g., chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, such as an amino acid or polypeptide, when the sequence is expressed. The coding sequence may comprise untranslated sequences (e.g., introns or 5' or 3' untranslated regions) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably-linked" or "operably-inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably-linked" is sometimes applied to the arrangement of other transcription control elements (e.g., enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene". Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," and "bean," refer to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

The term "osmotic stress" refers to any stress on the plant that disrupts the normal water, sugar, or electrolyte concentration in a plant cell or plant on the whole. Osmotic stress may be environmentally related, such as conditions of prolonged low water or drought, low temperatures, frost, freezing temperatures, high salt content in the soil, and the like. Osmotic stress may also occur naturally, as would be expected for seed development and maturation.

"Arabica" as used herein means the plant, or any portion, cutting, part, extract or tissue thereof, at any stage of development or growth, such as leaves, flowers, cherries or grain, from one or more *Coffea arabica* plants. Similarly, "robusta" means the plant, or any portion, cutting, part, extract or tissue thereof, at any stage of development or growth, including leaves, flowers, cherries or grain, from one or more *C. canephora* plants.

As used throughout, ranges are used herein in shorthand, so as to avoid having to set out at length and describe each and every value within the range. Any appropriate value within the range can be selected, where appropriate, as the upper value, lower value, or the terminus of the range.

Where used herein, the term "about" indicates that the given value, plus or minus 10%, is intended. "About" is thus used a shorthand to reflect the recognition that small variations from the literal value stated are still within the scope of the invention.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a promoter", "a method", or "a level" includes a plurality of such "promoters", "methods", or "levels". Reference herein, for example to "an antioxidant" includes a plurality of such antioxidants, whereas reference to "genes" includes a single gene. Similarly, the words "comprise", "comprises", and "comprising" are to be interpreted inclusively rather than exclusively. Likewise, the terms "include", "including" and "or" should all be construed to be inclusive, unless such a construction is clearly prohibited from the context. Where used herein "examples," or "for example," particularly when followed by a listing of terms, is merely exemplary and illustrative, and should not be deemed to be exclusive or comprehensive.

The methods and compositions and other advances disclosed here are not limited to particular methodology, protocols, and reagents described herein because they may be varied in ways that are apparent the skilled artisan. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, certain preferred compositions, methods, articles of manufacture, or other means or materials are described herein.

All patents, patent applications, publications, technical and/or scholarly articles, and other references cited or referred to herein are in their entirety incorporated herein by reference to the extent allowed by applicable law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not cited fully within the specification are set forth at the end of the specification.

Description

Several genes that are predominantly, or preferably, exclusively expressed, in seeds at the late stage of seed development/maturation have been isolated, identified, and characterized. Preferred genes showed significant amounts expression during the specified period. Candidate genes were selected from the Coffee EST Database at Cornell's SOL Genomics Network by comparing data for clones derived from five different stages/tissues, with a special focus on developing seeds. Two of genes provided herein, DIP1 and PR-5A, have now been well-characterized. Their corresponding promoters were isolated, sequenced, and characterized. DIP1 is predominantly or exclusively seed/grain-specific, and its promoter is useful for expressing recombinant proteins, for example during seed development, and particularly at the late stages of seed development/maturation, especially in *Coffea* spp.

Thus, in a first of its several aspects, the invention provides nucleic acid molecules isolated from coffee (*Coffea* spp.). These nucleic acids encode a protein comprising one or more of a BURP domain, 16 conserved cysteines residues of a pathogenesis-related protein, or a thaumatin domain.

The complement of nucleic acid molecules described herein are also provided. The skilled artisan will understand that because of the nature of nucleic acid molecules, for purposes herein, either a nucleic acid molecule (for example an encoding strand) or its complement (e.g. a noncoding strand) contain the equivalent information that the skilled artisan can apply in the practice of the various inventions described or claimed herein. Accordingly, the complements of the nucleic acid molecules provided herein are also included in this description.

In one embodiment, the encoded protein comprises a BURP domain, and further comprises one or more motifs comprising TXV or VXT repeated in tandem. Preferably, the BURP domain lies in the C-terminal portion of the protein. There are, in certain embodiments, several repeats of the TXV or VXT motifs, or tandems thereof Preferably, the protein so encoded is a dehydration induced protein ("DIP").

In a presently preferred embodiment, the encoded DIP protein comprises about 300 to 400 amino acid residues. In one embodiment, the DIP protein is DIP1 protein, such as that encoded by Unigene 124952 of the Coffee EST Database described above. In various embodiments, the protein has a sequence that is encoded by the open reading frame of any of the ESTs shown in Panel A of FIG. 3, or identified by Accession Numbers SGN-E672090, SGN-E66888, SGN-E674017, SGN-E675229, SGN-E665652, SGN-E672683, SGN-E672903, SGN-E670133, SGN-E672992, SGN-E663535, SGN-E662810, SGN-E666064, SGN-E672983, SGN-E668870, SGN-E662813, SGN-E686998, SGN-E673634, SGN-E670105, SGN-E665827, SGN-E673176, SGN-E674082, SGN-E665814, SGN-E675287, SGN-E672031, SGN-E666077, SGN-E662901, SGN-E666018, SGN-E662879, SGN-E670263, SGN-E665622, SGN-E673537, SGN-E675360, SGN-E673357, SGN-E674805, SGN-E674930, SGN-E674897, SGN-E664923, SGN-E672272, SGN-E674785, SGN-E663061, SGN-E671271, SGN-E672918, SGN-E662838, SGN-E672004, SGN-E668988, SGN-E686912, SGN-E673629, SGN-E670622, or SGN-E672335. In another embodiment, the DIP protein is DIP2 protein, such as that encoded by Unigene 121882 of the Coffee EST Database described above. In various embodiments, the protein has a sequence that is encoded by the open reading frame of any of the ESTs shown in Panel B of FIG. 3, or identified by Accession Numbers SGN-E658015, SGN-E625955, SGN-E635071, SGN-E628358, SGN-E651288, SGN-E653705, SGN-E653371, SGN-E653665, SGN-E642419, SGN-E653237, or SGN-E638808.

In various preferred embodiments, the DIP protein has an amino acid sequence that is 50% or more identical to SEQ ID NO:8 or 9. In other embodiments, the protein is 60, 65, 70, 75, 80, or 85% identical to SEQ ID NO:8 or 9. In yet others it is 86, 87, 88, 89, or 90% identical. Embodiments with as much as 91, 92, 93, 94 or 95% identity are also preferred, as are those with more than 95, 96, 97, 98 or 99% identity to SEQ ID NO:8 or 9. In one embodiment, the DIP protein has an amino acid sequence that is SEQ ID NO:8 or 9.

In other embodiments, the nucleic acid comprises any of SEQ ID NOs: 1-4. In preferred embodiments, the nucleic acid has a coding sequence that is 50% or more identical to the coding sequence set forth in SEQ ID NOs:1, 3 or 4. Still other embodiments are provided wherein the coding sequence is 60, 65, 70, 75, 80, or 85% identical to SEQ ID NOs:1, 3, or 4. Embodiments are provided wherein the coding sequence is 86, 87, 88, 89, or 90% identical, as are those with as much as 91, 92, 93, 94 or 95% identity, and embodiments with more than 95, 96, 97, 98 or 99% identity to SEQ ID NOs:1, 3, or 4. In a preferred embodiment, the coding sequence comprises one of SEQ ID NOs:1, 3, or 4. Even more preferred are sequences with precisely the coding sequence of SEQ ID NOs: 1, 3, or 4.

In another embodiment, the nucleic acid molecule encodes a protein comprising the 16 conserved cysteines residues of a pathogenesis-related protein, and a thaumatin domain. In one embodiment, the protein is a pathogenesis-related (PR) protein. Preferably, the PR protein comprises about 200-250 amino acid residues.

In one embodiment, the PR protein is a PR5A protein, such as that encoded by Unigene 119511 of the Coffee EST Database described above. In various embodiments, the protein has a sequence that is encoded by the open reading frame of any of the ESTs shown in Panel C of FIG. 3, or identified by Accession Numbers SGN-E671832, SGN-E664747, SGN-E673245, SGN-E665223, SGN-E675008, SGN-E671194, SGN-E673728, SGN-E670679, SGN-E664849, SGN-E669735, SGN-E670789, SGN-E674134, SGN-E671610, SGN-E665894, SGN-E670620, SGN-E669516, SGN-E670270, SGN-E665775, SGN-E674567, SGN-E664878, SGN-E670125, SGN-E674351, SGN-E670712, SGN-E669983, SGN-E672518, SGN-E668425, SGN-E670453, or SGN-E671330.

The PR protein has an amino acid sequence that is 65% or more identical to SEQ ID NO:10 or 11 in one embodiment. In others it is 70, 75, or even 80% identical to SEQ ID NO:10 or 11. In still others, identities of up to 85, 86, 87, 88, 89, or 90% are seen, while in yet others, as much as 91, 92, 93, 94 or 95% identity is observed. Embodiments with more than 95, 96, 97, 98 or 99% identity to SEQ ID NO:10 or 11 are also provided herein. In one preferred embodiment, an encoding nucleic acid molecule encodes a PR protein that has an amino acid sequence that is SEQ ID NO:10 or 11.

The nucleic acid molecule has a coding sequence that is 50% or more identical to the coding sequence set forth in SEQ ID NO:5 or 7 in various embodiments. Nucleic acids with identities of 60, 65, 70, 75% or more to SEQ ID NO:5 or 7 are also provided. Some molecules have up to 80, 85, and 86, 87, 88, 89, or 90% identity to SEQ ID NO:5 or 7. Sequences with more than 90% identity to SEQ ID NO:5 or 7 are also provided, such as those with 91, 92, 93, 94, 95, 96, 97, 98, or even 99% identity. In a preferred embodiment, the coding sequence of the provided nucleic acid molecule comprises SEQ ID NO:5 or 7.

In other aspects of the invention, provided are nucleic acid molecules, each of which is a gene having an open reading frame that comprises a coding sequence, as described above, for example, of either a DIP or PR related protein. Also provided are mRNA molecules produced by transcription, whether in vivo or in vitro, of such genes.

Another aspect of the invention provides cDNA molecules produced by reverse transcription of the mRNA molecules provided herein. Where the isolated nucleic acid molecules of the invention are themselves RNA, provided herein are cDNA molecules made therefrom. Such molecules are not found in nature as such of course, nor are the isolated RNA molecules from which such cDNA may be made.

In another of its several aspects, the invention provides vectors. The vectors comprise one or more of the nucleic acid molecules described herein. Other vectors comprise one or more promoters as described herein above and below. Still other vectors comprise both an isolated nucleic acid and a promoter as described herein. In one embodiment, the vector provided is an expression vectors, such as, but not limited to, a plasmid, phagemid, cosmid, baculovirus, bacmid, bacterial, yeast, or viral vector. Expression vectors from many such sources are known in the art and the skilled artisan will appreciate how to incorporate the novel nucleic acids provided herein into such vectors.

In one embodiment of the vector, the coding sequence of the nucleic acid molecule is operably-linked to a constitutive promoter, while in others it is operably-linked to an inducible promoter, or a developmentally-regulated promoter. In one embodiment, the developmentally-regulated promoter functions predominantly or exclusively during seed maturation in a plant. Preferably, developmentally-regulated promoter functions predominantly or exclusively during the late stages of seed maturation in a plant, such as during dehydration of the seed, particularly in the seed of a coffee plant. The skilled artisan will appreciate that seeds are the basis of many useful agricultural products, including, of course, seeds for consumption as such, oil seeds, and valuable seeds for planting. Any such seeds, whether or not for consumption may be used herein, including but not limited coffee, cereal crops such as corn, wheat, legume, barley, rye, oats and the like, peanuts and tree nuts of various types used for human or animal consumption, or as sources of oil, including almond, brazil nuts, cashews, filberts, hazelnuts, macadamias, pecans, pepitas, pine nuts, pistachios, and walnuts. Also included are sunflower, safflower, palm, corn, sesame, poppy, grape, coconut, cotton, rapeseed, flax, and other seeds used predominantly for oil purposes.

In other embodiments, the coding sequence of the nucleic acid molecule is operably-linked to a tissue-specific promoter, for example, a seed-specific promoter. In one embodiment, the seed-specific promoter is a seed-specific promoter in coffee.

In a presently preferred embodiment, the promoter is a DIP1 or PR-5A gene promoter. Preferably, the promoter is not substantially-induced by conditions of drought, osmotic stress, or salt stress at 50 mM. The promoter comprises untranslated portions of SEQ ID NO:2, 3, 6, or 7 or in certain embodiments herein. In other embodiments, the promoter has 80, 85, 90, 95, or more percent identity with any of SEQ ID NO:2, 3, 6, or 7, or more preferably, with the untranslated portions thereof More preferred are promoters having at least 80% identity to the untranslated portions of SEQ ID NO: 2, 3, 6, or 7, particularly the portions thereof that are upstream of, or 5' to the start codon. Examples of presently preferred promoters provided herein are exemplified in FIGS. 10, 11, 12, and 13, which also indicate various regulatory elements, motifs, and other features located within preferred embodiments of the promoters.

In various embodiments, the promoters provided herein comprise one or more regulatory sequences that are a TATA box, an E-box motif (CANNTG), an abscisic acid (ABA)-responsive element (ABRE), a gibberellin-responsive element (GARE), an MYB binding site motif, a GA-1 motif, or an ACGT core-containing motif In one presently preferred embodiment, the promoter comprises a sequence of SEQ ID NO:2 or 6.

Also provided herein are host cells transformed with any one or more of the vectors provided herein. In one presently preferred embodiment, the host cell is transformed with the vector comprising SEQ ID NO:2, 3, 6, or 7. The host cell is a plant cell, a bacterial cell, a fungal cell, an insect cell, or a mammalian cell in various embodiments. In various embodiments, the host cell is a plant cell from an alfalfa, almond, Arabidopsis, aster, banana, barley, begonia, beet, black tea, brazil nut, cacao, canola, carrot, cashew, chrysanthemum, clover, coconut, coffee, cucumber, delphinium, eggplant, filbert, hazelnut, lettuce, macadamia, maize, oats, pea, peanut, pecan, pepper, pine, pistachio, potato, pumpkin, rice, rye, safflower, sorghum, soybean, sugar beet, sunflower, tobacco, tomatillo, tomato, a turfgrass, walnut, wheat, or zinnia.

Also provided are fertile transgenic plants. The plants are produced by regenerating the host cells provided hereinabove. In one presently preferred embodiment, the plant is a *Coffea* spp.

Another aspect of the invention provides promoters isolated from a coffee plant gene that encodes a DIP or PR-5A protein. The gene encodes a DIP protein comprising about 300-400 amino acid residues in one embodiment. The encoded DIP protein has an amino acid sequence that is 50% or more identical to SEQ ID NO:8 or 9. In other embodiments, the protein is 60, 65, 70, 75, 80, or 85% identical to SEQ ID NO:8 or 9. In others, the encoded protein is 86, 87, 88, 89, or even 90% identical to those sequences. Embodiments wherein the encoded protein has as much as 91, 92, 93, 94 or 95% identity are also preferred, as are those with more than 95, 96, 97, 98 or 99% identity to SEQ ID NO:8 or 9. In one embodiment, the encoded DIP protein has an amino acid sequence that is SEQ ID NO:8 or 9.

In other embodiments, the gene comprises an open reading frame that is 50% or more identical to the sequence set forth in SEQ ID NO:1, 3, or 4. Other embodiments are provided wherein the open reading frame is 60, 65, 70, 75, 80, or 85% identical to SEQ ID NO:1, 3, or 4. Embodiments are provided wherein the open reading frame is 86, 87, 88, 89, or 90% identical, as are those with as much as 91, 92, 93, 94 or 95% identity, and embodiments with an open reading frame with more than 95, 96, 97, 98 or 99% identity to SEQ ID NO:1, 3, or 4. In a preferred embodiment, the open reading frame comprises one of SEQ ID NO:1, 3, or 4.

Another aspect of the invention provides promoters isolated from a coffee plant gene that encodes a PR-5A protein. In a preferred embodiment, the PR-5A protein comprises about 200-250 amino acid residues.

The gene from which the promoter is isolated encodes a PR-5A protein having an amino acid sequence that is 65% or more identical to SEQ ID NO:10 or 11 in one embodiment. In other embodiments, the encoded protein is 70, 75, or even 80% identical to SEQ ID NO:10 or 11. In still others, identities of up to 85, 86, 87, 88, 89, or 90% are seen. Embodiments wherein the gene encodes a protein with as much as 91, 92, 93, 94 or 95% identity to those specified sequences are also provided. Embodiments encoding a PR-5A with greater than 95, 96, 97, 98 or 99% identity to SEQ ID NO:10 or 11 are also provided herein. In one preferred embodiment the gene from which the promoter is isolated encodes a PR protein that has an amino acid sequence that is SEQ ID NO:10 or 11.

The gene from which the promoter is derived has an open reading frame that is 50% or more identical to the coding sequence set forth in SEQ ID NO:5 or 7 in various embodiments. Nucleic acids with identities of 60, 65, 70, 75% or more to SEQ ID NO:5 or 7 are also provided. Some molecules may also have up to 80, 85, and 86, 87, 88, 89, or 90% identity to SEQ ID NO:5 or 7. Sequences with more than 90% identity to SEQ ID NO:5 or 7 are also known, such as those with 91, 92, 93, 94, 95, 96, 97, 98, or even 99% identity. In a preferred embodiment, the coding sequence of the provided nucleic acid molecule comprises SEQ ID NO:5 or 7.

In another aspect of the invention, provided are chimeric genes comprising one, or more, of the promoters disclosed herein, operably-linked to one or more coding sequences.

Also provided herein are vectors for transforming a cell, comprising a chimeric gene as described above. A cell transformed with the vector, particularly a plant cell, and even more particularly, a cell of a *Coffea* spp., are also provided herein. Fertile transgenic plant produced by regenerating the transformed plant cells are also provided. In one embodiment of such plants, the plant is a *Coffea* spp.

In yet another aspect of the invention, methods of improving one or more quality attributes of a seed, such as a coffee bean are provided. The methods generally comprise modulating the production of one or more proteins produced in the seed, such as a coffee seed, predominantly or exclusively in the late stage of seed maturation. In a presently preferred embodiment, the seed is a coffee seed or other seed whose adequate maturation is important to the quality of an agricultural product.

In one embodiment, the one or more proteins comprise a DIP or PR-5A protein, or both. The quality attribute, in one embodiment, is a subjectively-determined (e.g., by a sensory evaluation panel) or objectively-measured aspect of flavor, aroma, mouthfeel, or in the case of coffee, a perceived or measured "cup quality". As used herein, "subjectively-determined" means that a value or parameter is determined subjectively, and although so determined, the value or parameter has statistical utility because of the number of subjects used and the manner in which the parameter is measured. Valid methods of such subjective analysis are known the art and will be understood by those of skill in sensory evaluation and the like. In other embodiments, the quality attribute is a useful measure of a biologic property of a plant, plant part, or the like, such as seed maturity, fruit ripeness, moisture content, content of protein, oil, chlorophyll, or other analyte at a particular time. Other quality attributes may include stability during storage, susceptibility to pathogen (e.g., insect, fungal, or microbial) deterioration during storage, oxidation, respiration, moisture content, and the like.

In one embodiment, the production of the protein is modulated by using any one or more of a nucleic acid, vector, host cell, or promoter provided herein.

In yet another of its several aspects, the invention provides analytical methods of assessing at least one quality attribute of a plant-derived agricultural product. The methods comprising the steps of:

providing a plant-derived agricultural product, or a batch or lot of such product;

selecting at least two analytes, said analytes including a first analyte, the presence of which is positively-associated with the quality trait, and a second analyte, the presence of which is negatively-associated with the quality the trait;

obtaining a sample of the plant-derived agricultural product, or a representative sample of the batch thereof;

determining, directly or indirectly, the relative amounts said first and second analytes in the sample; and assessing the quality trait based on the relative amounts of each of the first and second analytes, or a ratio therebetween.

While certain methods of assessing plant-derived agricultural products are known in the art, the present method is distinguished in using the ratio of two separate analytes, and further distinguished in requiring that at least one of the analytes is an RNA or a protein. In one embodiment, at least the first and second analytes are independently RNA or protein.

The skilled artisan will appreciate that rapid methods of protein analysis may be useful for rapid tests that can be used by purchasers or producers on-site. Alternatively, samples can be extracted and qualitative and/or quantitative measurements of mRNA indicative of gene expression may be useful. Methods of measuring or analyzing the protein or RNA analyte are known in the art and will be familiar to those of skill in the art. In one embodiment, real-time quantitative methods of measuring mRNA are used. In another embodiment, ELISA or similar detection methods are used form rapid measures of protein. The utility of protein analysis for such methods will of course require proper selection of proteins, for example, whose presence in a batch or lot of mature seeds is indicative of the presence of immature seeds in the batch or lot.

In a presently preferred embodiment of the method, the plant-derived agricultural product is a seed or seed-derived product. As discussed herein above, such seeds include many agricultural products, including cereals, legumes, nuts, cocoa, as well as coffee. For many such products, adequately assessing the quality or acceptability of a lot or batch before purchase, or determining the actual value of a lot or batch to be purchased and subsequently further processed would be of great value to the purchaser, and may help the provider of such products know, for example, the correct time to harvest or how to more adequately demonstrate distinguishing quality attributes of a agricultural product to prospective purchasers or processors. Thus, in one embodiment, the quality attribute relates to the maturity of the plant, or a plant part from which the agricultural product is derived.

As will be appreciated in certain embodiments, the maturity of a product can be related to for example, flavor, aroma or texture development. In one embodiment, the first analyte is indicative of a sufficiently mature plant or plant part, and the second analyte is indicative of an insufficiently mature plant or plant part. In other embodiments, maturity may not be desired in an plant-derived agricultural product, thus the skilled artisan will appreciate how to evaluate the data collected from the method based on the specific application for which it is used. For example, while in coffee, immature beans lead to off-flavor and poor quality, in other products, excess maturity may lead to off-flavors, or tough textures. Thus the skilled artisan will appreciate that such methods are of great value in assessing the quality of other plant-based agricultural products, including certain fruits and vegetables.

In a presently preferred embodiment, the plant is a *Coffea* spp. and the agricultural product is coffee cherries. Preferably, the method is used to determine the acceptability of a batch of coffee, determine the average maturity of the beans, detect the presence of beans from green or yellow cherries, grade the batch of coffee, or set the price of the batch of coffee, based on the relative presence of the first and second analytes.

In one embodiment, the first analyte is a DIP or PR-5A protein, or its encoding RNA, and the second analyte is a OLEO1 or LEA protein or its encoding RNA. In one embodiment, one of the analytes is not a protein or nucleic acid/polynucleotide, but rather a detectable molecule that is well-correlated with maturity (or immaturity) in a agriculture product. The presence of chlorophyll or dichlorogenic acids can be well-correlated with maturity, or lack thereof, in certain agricultural products, for example, coffee. One embodiment of the method employs three analytes including a DIP 1 or PR-5A protein or its encoding RNA, an LEA protein or its encoding RNA, and an OLEO1 protein or its encoding RNA.

The skilled artisan will appreciate that application of such methods may lead to improved attention and even methods of harvest, for example, in the coffee industry. Because these methods can provide the supply chain, from farm to processor, with objective measurements of the quality to the coffee cherries, producers can avoid contaminating otherwise valuable lots of coffee by the inclusion of unripe cherries, and what might otherwise be mediocre or even inferior lots can be improved by better quality control of harvesting, thus benefiting the producers and the processors.

These and other aspects of the invention can be further illustrated by the following examples. It will be understood that these examples are provided for purposes of illustration of specific aspects, and thus, they do not limit the scope of the invention disclosed herein as a whole, unless otherwise specifically indicated.

EXAMPLES

Materials and Methods
Plant Material and RNA Preparation

Fruit and other tissues from *C. arabica* L. cv. Caturra T2308 were obtained from greenhouse-grown trees and stored at −80° C. until use. Fruit from *C. canephora* (robusta) varieties BP409, BP358, Q121 were obtained from field-grown trees cultivated at an Indonesia Coffee and Cocoa Research Institute ("ICCRI") facility in Indonesia and frozen on site at −80° C. This material was then transported to the laboratory at −20° C. and then stored at −80° C. until use. Other tissues of BP409 were either obtained from ICCRI and transported as noted above, or obtained from greenhouse-grown trees.

Total RNA was obtained using phenol-chloroform extraction. An additional DNase treatment was carried out using RQ1-RNase-free DNase following the manufacturer's instructions (Promega, Ref: M6101), followed by repurification of the RNA using columns from the Qiagen RNeasy Plant mini kit. [RNA samples codes: RNA-T2308-2, RNABP409 1, RNA-BP358-1, RNA-Q121-1, respectively]

For the leaf maturity study, leaves were collected from *C. arabica* L. cv. Caturra T-2308 trees grown under greenhouse conditions and stored at −80° C. until use. The four stages of leaf maturity were: very young leaves (first leaves on the newest, non-lignified portion of a growing branch, ~2 cm), young leaves (just behind first leaves on the new branch, these are very green with "tender" tissue, ~4 cm), mature leaves (leaves collected in medium aged branch, these are dark green, "waxy" tissue, ~12 cm), and old leaves (yellowing leaves, ~12 cm). RNA was extracted by grinding the leaf material (stored at −80° C.) with a mortar and pestle. Total RNA was extracted with the Qiagen RNeasy Plant mini kit (#74904) following manufacturer's conditions. The RNA obtained was further treated with DNase using the "Qiagen RNase-Free DNase" kit according to the manufacturer's instructions to remove remaining DNA contamination. [RNA sample code RNA-T2308-leaves-3]

The germinating grain samples were obtained, and the RNA extracted, with DNase treatment as described previously ((Simkin, A. J. et al., 2006b); [RNA sample code RNA-T2308-Germ-1 3, see also (Simkin, A. J. et al., 2006a)].

For the dehydration experiment, small plants (approx 7 months old) of *C. canephora* varieties 'FRTO4' and 'FRT23' were used. These plants have been grown from somatic embryos in pots in the greenhouse. Three plants were selected as controls, and from the start of the experiment, were manually watered daily. Three other plants were not watered and thus subjected to progressive dehydration. Sampling of two leaves (2-3 cm in size) from each plant was carried out every week. When possible, samples were taken from the emerging growth at the top of plant. All samples were frozen directly in liquid nitrogen. RNA was prepared as described above. [RNA sample code—RNA-DS4].

For the salt stress experiment, microcuttings of *C. canephora* variety 'FRT12' propagated on medium B0.3 which is MS medium (Murashige, T. and Skoog F., 1962) containing benzylaminopurine at 0.3 mg/l, sucrose at 40 g/l and solidified with Gelrite 3 g/l. At the start of the experiment, the microcuttings were transferred to B0.3 medium containing an additional 50 mM NaCl.

Microcuttings subjected to salt treatment were sampled after 2, 7 and 10 days of treatment and frozen directly in liquid nitrogen. The same material left on the original plates served as the control and were also sampled at T=0, T=2, T=7, and T=10 days. RNA was prepared as described for the leaf development samples. [RNA sample code—RNA-NaCl]

For the experiments using stored coffee grain, mature red cherries were harvested from *C. canephora* FRT 09, FRT 07, FRT 17, FRT 28, FRT 49, FRT 53, FRT 72 trees grown on a farm in Ecuador. These cherries were then processed on the farm by the dry method. Briefly, ripe red cherries were hand picked and then sun dried on cement until humidity of the grain was approximately 12%. Dehulling was done with a Pinhalense "Descafrica" machine, and cleaning was by hand. The green coffee grain was then transported to the laboratory where it was stored under ambient conditions for over one year (uncontrolled storage conditions). RNA was prepared as described for the leaf development samples using 10 grain for each sample and then using 50 mg of the resulting powder for the RNA extraction. The RNA samples were obtained without DNAse treatment and eluted with 40 μl of RNA water. For the control BP358 RNA used in this experiment, the grain used was from fresh cherries noted above and frozen at −80° C. [RNA sample codes; RNA-FRT09-H1, RNA-FRT09-H2, RNA-FRT09-H3, RNA-FRT09-2005, RNA-BP 358 42W-A, RNA-FRT07-A, RNA-FRT17-A, RNA-FRT28-A, RNAFRT49-A, RNA-FRT53-A, RNA-FRT72-A]

cDNA Synthesis and Gene Expression Analysis Using Quantitive RT-PCR cDNA was prepared as describe by (Lepelley, M. et al., 2007) using poly dT. The method for quantitative RT-PCR was as described in (Simkin, A. J. et al., 2006b), except the cDNA dilution used was either 10-fold [Sample codes: cDNA2-RNA BP409-2; cDNA2-RNA T2308-2; cDNA1-RNA T2308 Germ-1], or 100-fold [Samples codes: cDNA1-RNA BP358-1; cDNA1-RNA Q121-1; cDNA1-RNA T2308-leaves-3; cDNA1-RNA-D54; cDNA1-RNA-NaCl3].

For sample RNA sample codes RNA-FRT09-H1, RNA-FRT09-H2, RNA-FRT09-H3, RNAFRT09-2005, RNA-BP 358 42W, RNA-FRT07-A, RNA-FRT17-A, RNA-FRT28-A, RNA-FRT49-A, RNA-FRT53-A, and RNA-FRT72-A, poly dT was used as the primer.

Note: No DNase I treatment was carried out for the RNA samples from the stored coffee grain samples described here. However, a control experiment using FRT09 RNA samples without RTcDNA synthesis (-RT FRT09) showed no significant amplification of the either OLEO1 or DIP1 gene sequences, indicating that any genomic DNA in the RNA samples are too low to interfere with QRT-PCR analysis of the corresponding transcripts. Thus, it appears that there is not significant level of genomic DNA contamination in the RNA samples described herein.

The cDNA preparations included:
cDNA2-RNA BP409-2
cDNA2-RNA T2308-2
cDNA1-RNA BP358-1
cDNA1-RNA Q121-1
cDNA1-RNA T2308-leaves-3
cDNA1-RNA T2308 Germ-1
cDNA1-RNA-DS4
cDNA1-RNA-NaCl3

The TaqMan primers and probes used are noted in Table 1.

TABLE 1

Primers and probes used in Taqman® real-time quantitative RT-PCR assay.

| Primer | Clone | Primer Sequence 5'-->3 | SEQ ID NO: | Amplicon Length |
|---|---|---|---|---|
| rp139F1 | A5-1750 | GAACAGGCCCATCCCTTATTG | 12 | 69 pb |
| rp139R1 | (CcRPL39) | CGGCGCTTGGCATTGTA | 13 | |
| Probe Rp139MGB | | ATGCGCACTGACAACA | 14 | |
| Fwd124952 | cccs46w20f16 | CCCAAAACACTTGGCTTTCAA | 15 | 64 bp |
| Rev124952 | (CcDIP1) | GAAATGGCAAACAGGAACTTGTC | 16 | |
| Probe 124952 | | TCTGCAGATCAAGCCA | 17 | |
| Cccp21sg1-F1 | cccp21sg1 | TGGCTCGTGCGCATAAACT | 18 | 137 bp |
| Cccp21sg1-R1 | (CcDIP2) | TGGGCATAGGAGTGTTTGGAA | 19 | |
| Probe Cccp21sg1-MGB1 | | TTATGGAATTTCTGAAGCTT | 20 | |
| Fwd119511 | cccs46w16n19 | GGTGCACCGCCGACATA | 21 | 58 bp |
| Rev119511 | (CcPR-5A) | CAACCTCCTGGAGCTTTAAGCA | 22 | |
| Probe 119511 | | TGGGCAGTGCCCAAG | 23 | |
| F851 | Dav1-53 | CCGACTCATGAAGGCGTCTT | 24 | 61 bp |
| R851 | (CcOLE1) | GTCCTGCAGCGCCACTTT | 25 | |
| Probe 851 | | CCAGGAGCAAATGG | 26 | |
| CcLEAP1_F | Dav1-59 | TCTGCTTCAATATCCCCTTCGT | 27 | 67 bp |
| CcLEAP1_R1 | (CcLEA1) | GTGACACAGTCCACTAAACAGTTGGTA | 28 | |
| Probe CcLEAP1-MGB | | TGCCCCTTAGACTGTC | 29 | |

*Primers and probes were designed using PRIMER EXPRESS Software (Applied BioSystems).
All MGB Probes were labelled at the 5' end with the fluorescent reporter dye, 6-carboxy-fluorescein (FAM), and at the 3' end with the quencher dye, 6-carboxy-tetramethyl-rhodamine (TAMRA), except the rp139 probe which was labeled at the 5' end with the fluorescent reporter dye VIC, and at the 3' end with quencher TAMRA. The rp139 primers and probe correspond to a constitutive gene, the primers and probe "124952" correspond to the CcDIP1 gene, "cccp21sg1" correspond to the CcDIP2 gene, "119511" correspond to the CcPR-5A gene, "851' correspond to the CcOLE-1 gene (Oleosin) and "LEAP1" correspond to the CcLEA1 gene.

Promoter DNA Isolation

The DIP-1 and PR-5A promoter sequences described here were isolated using the Genome Walker kit from BD Biosciences and the conditions described by (Simkin, A. J. et al., 2006b). The gene specific primers are given in Table 2.

TABLE 2

Primers for Genome-walking and sequence amplification from genomic DNA

| Unigene/Plasmid | Clone | Primer | Primer Sequence 5'-->3 | SEQ ID NO: |
|---|---|---|---|---|
| CGN-U124952 | pcccs46w20f 16 (DIP1) | GW1 124952 | TCGATAGCTTTCGGCATAGGACTGTTAGGG | 30 |
|  |  | GW2 124952 | TTCCAATATGTCTCAGCAGGTTGTGCTG | 31 |
| CGN-U119511 | pcccs46w16 n19 (PR-5A) | GW1-b 119511 | ATGTTTGGCCTCGGTCTAGCCTTCG | 32 |
|  |  | GW2 119511 | TTTCGGATGTCGAAAGTGGCAGCATGG | 33 |
| Primers from the Universal "GenomeWalker" Kit of BD Biosciences |  | AP1 | GTAATACGACTCACTATAGGGC | 34 |
|  |  | AP2 | ACTATAGGGCACGCGTGGT | 35 |
| pAS22 | — | Dip1A F5 | GAACAATTTTCTATTTGGTG | 36 |
|  |  | Dip1A R5 | TAGCTTTCGGCATAGGAC | 37 |
| pAC1 | — | Dip1AC1 F | GTCAGCCACATTAAGAGCAGG | 38 |
|  |  | Dip1 AC1 R | GGGCAAGCATTTGGAGTTTC | 39 |
| pAC7 | — | AP2 GW | ACTATAGGGCACGCGTGGT | 40 |
|  |  | GSP2 119511 | TTTCGGATGTCGAAAGTGGCAGCATG | 41 |
| pAC17 | — | PRP-F2 | GAAGAGAATACATGGGACG | 42 |
|  |  | PRP-R2a | GCAGATGACGTTATGTGTT | 43 |

Figure 1:
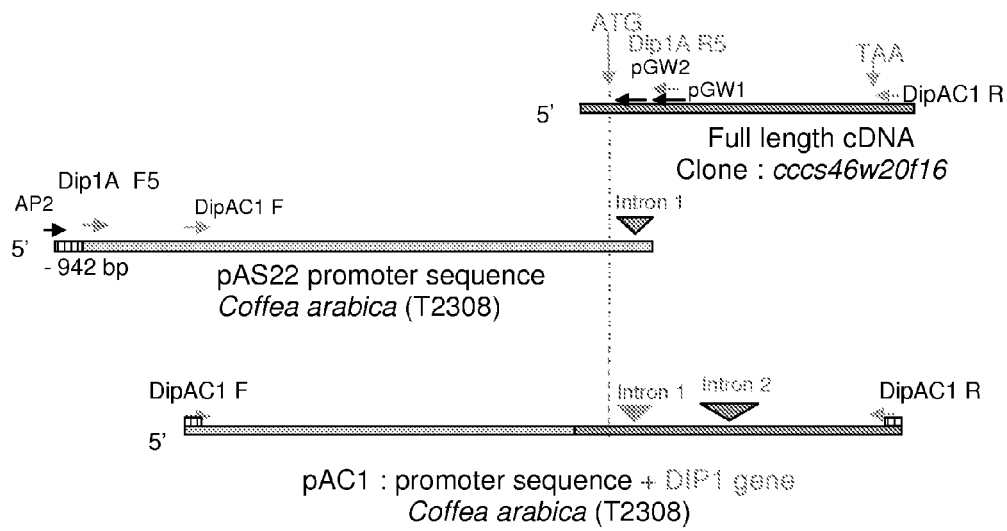
FIG. 1: Strategy for the isolation of the DIP1 promoter sequence from *Coffea arabica* cv. Caturra T2308 using the GenomeWalker technique (Universal GenomeWalker™ Kit, BD Biosciences Clontech). The nested primers GW1 124952 TCGATAGCTTTCGGCATAGGACTGTTAGGG (SEQ ID NO: 30) and GW2 124952 TTCCAATATGTCTCAGCAG-GTTGTGCTG (SEQ ID NO: 31) were designed from the 5' end of the cDNA clone pcccs46w20f16. These were used with the GW kit primers AP1 and AP2 to amplify a genomic DNA fragment of 1136 bp from *C. arabica* cv Caturra T2308 genomic DNA using PCR. This fragment was cloned into pCR4-TOPO to give pAS22 (see methods for details). This plasmid was also called pCR4-GW124952 #4E. The genomic DNA sequence in pAC1 was obtained by PCR amplification from genomic DNA (*Coffea arabica* cv Caturra T2308) using the forward primer DipAC1 F gtcagccacattaagagcagg (SEQ ID NO: 38) designed from 5 end of pAS22 and a reverse primer Dip1AC1 R gggcaagcatttggagtttc (SEQ ID NO: 39) designed from the 3' noncoding region of the cDNA (CcDip1). The size of the fragment obtained was 2242 bp, and was cloned pCR4-TOPO. This genomic sequence contained 3 exons and 2 introns.
Figure 2:
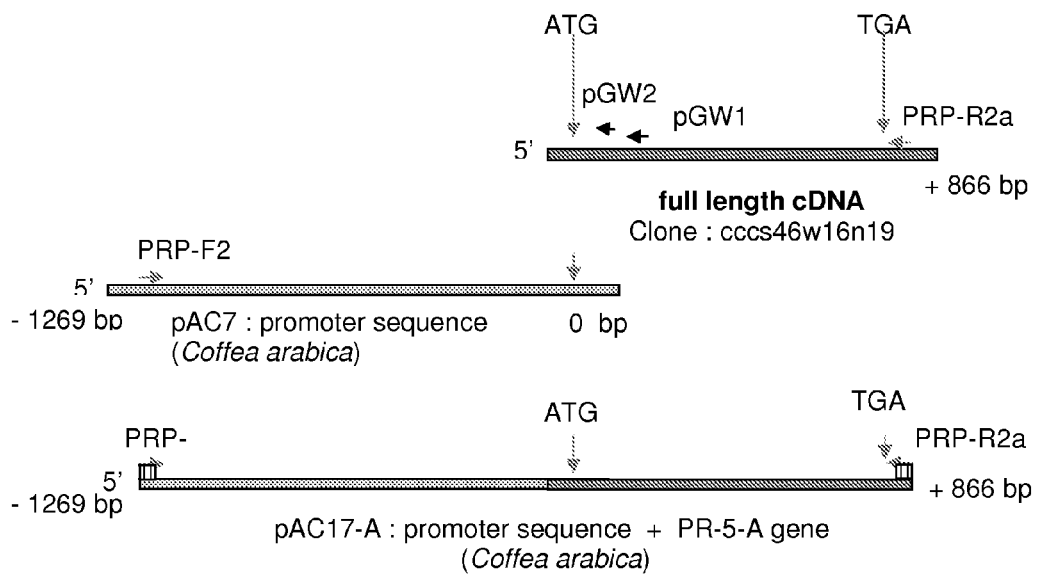
FIG. 2: Strategy for the isolation of the PR-S-A promoter sequence from *Coffea arabica* (T2308) using the GenomeWalker technique. PCR was carried out with genomic DNA from *Coffea arabica* cv. Caturra (T2308), using primers GW1-b 119511 ATGTTTGGCCTCGGTCTAGCCTTCG (SEQ ID NO: 32) and GW2 119511 TTTCGGATGTC-GAAAGTGGCAGCATGG (SEQ ID NO: 33). The primers were designed from the 5' end of the cDNA clone pcccs46w16n19 and the GW primers AP1 and AP2. The 1380 bp fragment obtained was cloned into the vector pCR4-TOPO by PCR amplification producing pAC7 (see methods for details). The insert of pAC17-A containing the promoter and protein coding region was then obtained by PCR amplification from genomic DNA (*Coffea arabica* cv. Caturra (T2308)

The overall strategy used for isolating the contiguous promoter and gene sequences are outlined in FIGS. 1 and 2 for DIP1 and PR-5A, respectively.

Other putative DIP 1 promoter sequences: Another genomic DNA fragment was also recovered from *C. arabica* genomic DNA and cloned into the pCR4-TOPO vector (Invitrogen) to make pCR4-GW124952 #4C (600 bp). A second genomic fragment of approximately 900 bp was also recovered from *C. canephora* and cloned into the pCR4-TOPO vector to make pCR4-GW124952 #3D. These two genomic DNA fragments, and the sequence of pAS22, have very high level of homology at their 3' ends, but the sequences differ significantly at their 5' ends. It remains to be determined if the *C. arabica* genomic sequence pCR4-GW124952 #4C and *C. canephora* (robusta) genomic sequence pCR4-GW124952 #3D represent other DIP genes, or other alleles of the same DIP1 gene.

DNA sequencing and DNA sequence analysis:

Plasmid DNA was purified using Qiagen kits according to the instructions given by the manufacturer and this DNA was sequenced using the dideoxy termination method (Sanger, F. et al., 1992) by GATC Biotech AG (KONSTANZ, Germany) Computer analyses were performed using Laser Gene software package (DNASTAR). Sequence homologies were verified against GenBank databases using BLAST [(Altschul, S. F. et al. 1997)].

Example 1

Isolation and Characterization of cDNA for Genes Which are Strongly Expressed at the End of Grain Development To find genes either primarily, or exclusively, expressed in the grain during the last stage of development (during dehydration phase), we screened the coffee expressed sequence tag (EST) database at the SOL Genetics Network at Cornell University (www.sgn.cornell.edu) for unigene sequences that:

a) are found only in the 46 week grain library, and
b) have more than 5 ESTs (in order to reduce the number of weakly expressed genes that may also be expressed elsewhere in the plant).

Those unigenes which are both relatively strongly expressed, and predominantly, or preferably, exclusively, expressed only in a cDNA library from mature grain, e.g., 46-week coffee grain were selected. Only unigenes with 5 or more copies were selected for further study, taking into account the number of ESTs and annotations of the sequences (not shown). The Unigenes selected are shown Table 1.1.

TABLE 1.1

Overview of two unigenes with very high expression in the 46 week library of the SGN coffee EST database, as described. The annotations given are the best hits found using the automated searches done by the Cornell informatics group

|  | CGN-U124952 | CGN-U119511 |
|---|---|---|
| Number of EST's in 46 week library | 49 | 28 |
| Blast Annotation With NCBI With TAIR | BURP domain-containing protein (*Bruguira gymnorrhiza*) Dehydration induced-protein RD22 (*Arabidopsis thaliana*) | Pathogenesis-related protein 5-1 (*Helianthus annuus*) Osmotin-like protein OSM34 (*Arabidopsis thaliana*) |
| Annotation using inter-protein domain search | BURP domain | Thaumatin, pathogenesis-related domain |
| Given name | DIP1 | PR-5A |

The expression of each of these genes in the grain at 46 weeks was quite high, with unigene CGN-U124952 having 49 EST's (FIG. 3, Panel A) and unigene CGN-U119511 having 28 EST's (FIG. 3, Panel C). One of the longest cDNA of each unigene was isolated and sequenced. When the complete sequence of unigene CGNU124952 was blasted against a coffee gene database, a second very closely related unigene was found (CGN-U121882) with 11 ESTs from either the pericarp or leaf libraries only (FIG. 3, Panel B). One of the longest ESTs of this unigene was also isolated and sequenced.

FIG. 7 shows the optimized alignment of the clones, pcccs46w20f16 from unigene CGN-U124952, and the highly-related pcccp21sg1 from unigene CGN-U121882, with the closest-related sequences in the databases found via a BLAST search. This alignment shows that both encoded proteins contain a well-conserved C-terminal BURP domain (Hattori, J. et al. 1998). One of the most related proteins is the RD22 protein of *Arabidopsis*, which is induced during dehydration (Yamaguchi-Shinozaki K., and Shinozaki K. 1993). Therefore, we have named the corresponding proteins in coffee dehydration induced proteins (DIPs); i.e., *Coffea canephora* DIP1 and *Coffea canephora* DIP2, respectively. So far, there is no significant information in the literature concerning the role of these proteins in the plant. The coffee DIP cDNA also contains repeats of the motifs TXV and VXT, which are found in the other family members, although the number of motifs varies between the different sequences (Van Son Le 2005).

The two related DIP sequences have been aligned with Megalign software using the clustal W program over the complete cDNA sequences, revealing that they are approximately 63.3% identical. The encoded protein sequences are 56.1% identical. DIP2 is not expressed in the grain, but is expressed in several other tissues, with roots, stems, and leaves showing the highest levels. We have also noted that the arabica tissues analysed often appeared to have higher levels of expression than the comparable robusta tissues tested. Further work, with other varieties of these two different species, is necessary to determine if there is a real species-specific difference in the expression of DIP2.

Examination of the optimized alignment of the clone, pcccs46w16n19 from unigene CGN-U119511, and the most-related database sequences, showed that the encoded protein has high similarity to the pathogenesis-related proteins in group 5. This alignment also indicates that this coffee protein sequence contains a motif found in thaumatin-like proteins as well as sixteen highly-conserved cysteine residues (FIG. 8). The high degree of homology of the protein sequence in pcccs46w16n19 led us to name this gene *Coffea canephora* pathogenesis-related protein, PR-5A. There is relatively little information in the literature concerning the role of these proteins in the plant, although different members have been implicated in either pathogen resistance or some undefined role in water management in the plant. Examination of the hydrophobicity plots of the CcDIP1, CcDIP2, and CcPR-5A, (FIG. 9) show that all have a short N-terminal hydrophobic segment, which is a potential leader peptide sequence. The presence of a leader or signal peptide suggests all three of these protein are destined for export from the endoplasmic reticulum. Apart from this putative leader peptide portion, all three proteins are highly hydrophilic. The relevance of this latter observation is not currently known.

Example 2

Expression Analysis of CcDIP1, CcDIP2 and CcPR-5A in Different Tissues of *C. Arabica* and *C. Canephora*

The relative transcript level of the three genes in different coffee tissues was determined by QRTPCR. The results obtained are presented in FIG. 14. A low level of DIP1 transcripts were detected in the small green grain of arabica (RQ 0.31), while in robusta, only very low levels were detected at this stage (RQ 0.03). In the large green stage, when the endosperm begins to form/expand, DIP1 transcript levels increased very significantly (RQ 67.2). In contrast, for robusta, the levels rose only modestly at this stage (RQ 0.019). At the yellow stage, the transcript levels for arabica were relatively similar to those seen at the large green stage (RQ 59.4), but in robusta, the level rose significantly (RQ=6.6). The DIP1 transcript level in the red grain was elevated slightly for arabica, but further rose substantially in the red robusta grain (RQ 37.2). Overall, DIP1 transcripts appeared earlier in arabica versus robusta grain in relation to the development of the cherries of these two species. Very little DIP1 expression was detected in the other tissues examined, although low levels were detected in the large green, yellow, and red pericarp, with the large green stage being highest (RQ 0.36 and 0.043 for robusta and arabica, respectively). It is interesting to note that no DIP1 transcripts were detected in the robusta root, branch, leaf, or flower tissues, but in arabica, low levels of transcripts were detected for three of these tissues (RQ=0.027 branch, 0.005 leaf, and 0.008 flowers).

Expression analysis for DIP2 shows that the tissue expression pattern of this gene is significantly different from that of DIP1 (FIG. 14). In the grain, very low transcript levels were seen at the small green stage in both arabica and robusta. No DIP2 was detected in the red pericarp of robusta, but a low level of expression was detected in the small green to yellow stages, with the small green stage of robusta showing the highest expression (RQ=0.2). However, few DIP2 transcripts were detected in arabica pericarp tissue. DIP2 transcripts were also detected in the other tissues examined, with RQ levels of the arabica roots, branches, leaves and flowers showing RQ values of 0.37, 0.73, 0.65, and 0.04, respectively. Interestingly, in robusta, much lower transcript levels were detected in roots, branches, and leaves (RQ values of 0.012, 0.007, and 0.016 respectively). No expression was detected in the robusta flowers. Given the somewhat unexpected levels of variation between the CcDIP2 expression in some tissues of arabica versus robusta, further experiments, using new RNA samples, are necessary to confirm these differences.

The expression analysis of PR-5A shows that this gene is expressed in the grain, with arabica showing RQ values of 0.04, 0.55, 1.0, and 1.23 for the small green, large green, yellow and red stages of arabica respectively (FIG. 14). Again, expression of a late gene like PR-5A appears to be retarded during robusta grain development. No transcripts were clearly detected in small green or large green robusta grain, but very low levels were detected at yellow stage, and then rose more at the red stage (RQ=0.005 and 0.75 respectively). In the pericarp tissue, there is a low level of PR-5A transcripts present at the small green stage of robusta and arabica (RQ=0.014 and 0.026 respectively) and this level rises as development continues.

The increase in transcript level in arabica started earlier than in robusta. For example, at the yellow stage, the RQ is 0.12 for robusta and 2.62 for arabica, while the values become much closer at the red stage (RQ=2.3 and 2.5 respectively). The fact that PR-5A expression was detected earlier in arabica pericarp versus robusta pericarp indicates that, as previously observed for the grain, the pericarp of robusta appears to mature later than that of arabica (vis-à-vis red color development). While the function of the PR-5A protein is not known, this gene is a member of the gene family Pathogenesis-Related Protein 5 (PR-5, also called thaumatin-like proteins, TLP). Some PR proteins have been found to have antifungal properties (Vigers, A. J. et al. 1991); (Hu, X. and Reddy, A. S. 1997).

The PR-5A transcripts were detected in the root and branch of both robusta and arabica (RQ=0.17 and 0.36, versus RQ=0.27 and 0.0042). More significant differences in transcript levels were observed between robusta and arabica in the leaves (RQ=0.076 versus not detected).

Example 3

Expression Analysis of DIP2 and PR-5A During *C. Arabica* Leaf Development

DIP2 is expressed in the leaves of both arabica and robusta, but PR-5A shows significant differences in leaf expression for the two species (FIG. 14). We decided to examine if the transcript levels of these genes is influenced by the developmental stage of the leaves in arabica.

The data presented in FIG. 15 show that DIP2 transcript levels increase as the leaf develops, with transcript levels rising nearly five fold from the very young leaves (RQ=0.29) to the mature leaves (RQ=1.36). The transcript levels then seem to fall again in the old leaves (RQ=0.91). In contrast, PR-5A transcripts were hardly detectable in the developing leaves (max RQ was 0.0016 in young leaves), confirming the results seen in FIG. 14. Interestingly, the PR-5A transcript levels appear to rise in a relatively significant fashion in the old leaves (RQ=0.043). Because the levels of this protein in developing arabica leaves were nearly undetectable in very young to mature leaves, but showed a low level in old leaves, perhaps this protein plays a role in senescence.

Example 4

Expression Analysis of DIP 1, DIP2 and PR-5A During *C. Arabica* Seed Germination The expression of the three genes in the whole grain during germination (FIG. 16) was examined. DIP1 transcript levels were highest at the start of the experiment (RQ=1.2) and then fell as germination continued up to the 30-day sample, which showed a spike in DIP1 expression. The RQ seen for DIP1 at the start of the germination study was significantly lower than that seen in the mature grain, suggesting that this transcript may have become destabilized during the grain drying and washing steps. DIP2 transcripts were not detectable in the early stages of germination, but become detectable around 60 days into germination (RQ=0.05). PR-5A transcript levels at T=0 (RQ=0.053) were much lower than in the mature arabica grain, again indicating that there appears to be a significant loss of these transcripts during the various washing and drying steps. The levels of PR-5A transcripts were relatively stable during the first 5 days, but then climbed slightly at 30 days, before falling again (60 day sample, RQ=0.03).

Example 5

Expression Analysis of DIP 1, DIP2 and PR-5A in *C. Canephora* Under Osmotic Stress Conditions Expression in Leaves of Drought Stressed Plants The genes DIP1 and PR-5A are strongly expressed during the dehydration phase of late grain development, and thus, could be regulated by the levels of water stress perceived by the cell. To test the possibility that expression is so regulated, the expression of these genes in the leaves of robusta plants undergoing dehydration stress for six weeks was examined. Other analyses had established that the dehydrin CcDH1 gene (Hinniger, C. et al. 2006), a gene which is in a family of potentially ABA-mediated stress genes, was strongly induced in the leaves of drought-stressed plants during weeks 5 and 6 of the drought conditions (data not shown). As seen earlier, DIP1 transcripts were not detected in the leaves of well-watered robusta plants (FIG. 17). However, upon water stress, a low level of DIP1 induction was detected. RQ of 0.01 and 0.005 were observed for the leaves of stressed FRT04 plants, and RQ of 0.012 and 0.01 for leaves of stressed FRT23 plants.

Measurement of DIP2 transcripts in the leaves of the watered controls showed that DIP2 expression varies significantly between the varieties (RQ=0.36 and 3.14, respectively, for FRT04 and FRT23). The levels of DIP2 transcripts in the drought-stressed samples were similar to the controls, indicating that drought stress does not increase DIP2 transcript levels. It is not known if the variation of DIP2 levels observed is variety-specific, or due to some other factor(s).

There was no consistent change in the levels of PR-5A transcripts in the leaves of drought-stressed and non-stressed plants. One variety showed a very slight induction, and the other showed slightly elevated levels in the control, followed by a reduction in the stressed samples. Overall, it appears that PR-5A was not induced by drought stress in the leaves of coffee.

Expression in Microcuttings Subjected to Elevated Salt

Plants exposed to elevated salt levels also exhibit an osmotic stress response (Choudhury, A. et al., 2007; Yamaguchi-Shinozaki, K. and Shinozaki, K., 2006). Therefore, the effect of elevated NaCl on the expression of the DIP1, DIP2, and PR-5A genes were examined. Due to the limited number of small trees available for such a stress experiment, these experiments were carried out using microcuttings. Microcuttings of robusta variety FRT 12 were grown up on plates on B0.3 media (see methods), and then half of the microcuttings were placed on new B0.3 media, and half were placed on the same media containing an additional 50 mM NaCl. Samples of the untreated microcuttings were taken after 2, 7, and 10 days; samples of the treated microcuttings were taken after 7 and 10 days for expression analysis. As expected, no DIP 1 transcripts were detected in the early control material, while a small induction in the control was observed after 10 days, possibly due to the aging of the samples on the original plates (FIG. 18). A small induction of DIP1 expression was also observed in the 7 and 10 day samples. Expression analysis of DIP2 showed no differences in expression between treated and untreated samples.

The RQ values obtained for DIP2, however, were significantly higher (approximately 1.5) than seen for robusta leaves (FIG. 14), but close to those seen for the arabica sample in this experiment. No induction of DIP2 was seen for the salt treatment. Similarly for PR-5A, the control material had somewhat higher transcript levels to those seen previously in leaves, but there was no increase in the levels in the salt-treated material. A water stress-inducible gene (DH1) was previously shown to be induced at +50 mM salt (Sayffer, F., unpublished data) using the same cDNA preparation. Thus, overall, the results in FIG. 18 indicate that there was no major increase in DIP2 or PR-5A transcripts induced by 50 mM NaCl. Microcutting may result in higher baseline expression of the DIP2 or PR-5A genes than in leaves, due perhaps to the less mature nature of the microcut tissues, or to specific tissues existing in high quantities in microcuttings but not in the leaves.

Example 6

Isolation of the 5' Upstream Regulatory Regions of DIP 1 and PR-5A Genes

There are currently no coffee promoter sequences available that enable strong recombinant gene expression during late grain development. The data presented in FIG. 14 show that the genes DIP1 and PR-5A are induced in the grain during the last phase of grain development. The promoter of DIP1 appears to be both stronger, and more specific for grain, than that of PR-5A. In order to have late grain promoters with different strengths, we decided to isolate the promoters of both genes using the genome walking technique.

Only one "genome walking" step was needed to obtain a 1136 bp fragment which putatively contained the DIP1 promoter. This fragment was cloned in to the vector pCR4-Topo to generate the plasmid pAS22 (see FIG. 1). To verify the contiguity of the genomic sequence of pAS22 and the DIP1 cDNA sequence, a genomic fragment containing both the promoter region and the cDNA sequence was also isolated and cloned into vector pCR4-Topo, yielding the plasmid pAC1. The sequence obtained for pAC1 was then aligned with pAS22 and pcccs46w20f16. This alignment showed that the DIP1 gene contains two introns of 104 bp and 396 bp respectively (see FIG. 10). There were eight base changes between the two overlapping sequences in the transcribed region of the gene, six of these changes resulted in amino acid changes, of which at least two were potentially significant changes. There were 10 bp differences found in the DIP1 5' promoter region sequences, and several putative promoter elements were identified (for promoter element details, see FIG. 11).

Only one "genome walking" step was needed as well to clone a 1380 bp fragment which putatively contained the PR-5A promoter. This fragment was cloned into the vector pCR4-Topo to generate the plasmid pAC7 (see FIG. 2). To verify the contiguity of the genomic sequence of pAC7 and PR-5A cDNA, a genomic fragment, containing both the majority of the promoter region and the cDNA sequence, was isolated and cloned into vector pCR4-Topo yielding the plasmid pAC17-A. The sequence obtained for pAC17-A was then aligned with pAC7 and pcccs46w16n19 (see FIG. 12b). This alignment showed that the PR-5A cDNA does not contain any introns (see FIGS. 12a and 12b for details). There were 15 bases changes between the three sequences in the transcribed region of the gene, eight of which resulted in amino acid changes. A major change in the coding region is observed in the pAC17-A sequence relative to the cDNA sequence pcccs46w16n19 generating a new stop codon 66 bases before the Stop codon in sequence pcccs46w16n19 (see FIGS. 12a and 12b). There were 19 bases differences found in the PR-5A 5' promoter region sequences, and several putative promoter elements were identified (see FIG. 13).

Example 7

Comparative Transcript Analysis for Genes Expressed at Different Stages of Grain Development: Transcript Accumulation of LEA1, OLEO1 and DIP1

With the isolation of the DIP1 gene, three different grain-specific coffee genes, LEA1, OLEO1, and DIP1, each expressed only during a limited period of grain development, have been identified. LEA1 is expressed only during the perispenn/endosperm transition (Hinniger, C. et al. 2006; Tanksley, S. et al. 2007; PCT Patent Publication No. WO 2007/005980). OLEO1 is expressed during endosperm development/expansion (Simkin, A. J. et al. 2006b; Simkin, A. J. et al. 2006a, PCT Patent Publication WO 2007/005928). As disclosed herein, DIP1 is expressed during the last phase of development (e.g., dehydration stage). To examine the level of expression overlap for these genes, the relative transcript accumulation for each gene was quantitatively measured using QRT-PCR with RNA/cDNA prepared from several stages of the developing grain in robusta cherries (variety Q121).

The data presented in FIG. 19 confirm that each gene has a distinct developmental expression pattern. LEA1 expression is primarily limited to the period around week 26, reaching an RQ=9.8 (indicative of the perispenn/endosperm transition). OLEO1 expression is first detected at week 26, confirming that the endosperm is beginning to form at this time. The level of OLEO1 transcripts increased further as development continued, reaching the maximum levels during the 30-34 week period (RQ approximately 7.5). The levels then fell gradually to reach RQ=1.6 at 42 weeks. This time represents the mature grain for this fast ripening robusta variety. In this sample set, significant DIP1 expression is detected at 38 weeks, then rises significantly during the last developmental stage, reaching RQ=32.1 in the mature, 42-week grain. The results in FIG. 19 confirm these three genes are expressed during distinct, although somewhat overlapping developmental periods in the coffee grain.

Example 8

Measurement of LEA1, OLEO1 and DIP1 Transcript Levels in Stored Green Coffee Grain Grain maturity is believed to influence the final cup quality, with less mature coffee having inferior "green" off-flavors (Farah A. and Donangelo C. M., 2006). Thus, a method to accurately determine the maturity level of stored grain could be useful to help understand the importance of grain maturity vis-à-vis the basis of optimum coffee quality for each variety, or to identify a potential explanation for specific flaws such as the presence of "green" notes in commercial coffee samples. However, for such an approach to be useful, it is necessary that relatively small amounts of immature grain can be detected in a mixed batch that also contains mature grain. To examine this issue for a robusta coffee, we have analysed mixtures of cDNA made from both 26-week grain (very immature/high LEAP1 transcript level) and mature 42-week grain (high DIP1 transcript level), plus mixtures of cDNA made from the partially-mature 30-week grain (high oleosin) and the mature 42-week grain (high DIP1).

As presented above, the data presented in FIG. 19 demonstrate that quantification of the transcript levels for LEA1, OLEO1, and DIP1 can be used to determine the development stage of a coffee grain. For example, detection of LEA1 transcripts in a single grain would indicate that it is quite immature, while the detection of high levels of DIP1 expression relative to OLEO1 expression would indicate that this grain is near, or, at an acceptable stage of maturity. Moreover, the results shown in FIG. 20 demonstrate that the expression ratio for the three genes is a useful indicator of the maturity of the grains present in a batch, allowing detection, and rejection of batches with unacceptable amounts of immature grain. For example, the expression ratio associated with a mixture of 5% 26-week plus 95% 42-week cDNA is very different to the expression ratio in a mixture of 50% of each cDNA. Similarly, the expression ratio for the three genes in a mixture of 5%

30-week plus 95% 42-week cDNA is very different to the ratio observed for a mixture of 50% of each cDNA.

The results suggest that quantitative expression analysis for three genes expressed predominantly at different stages of grain maturity can reveal in a mixed batch of grain: a) the presence of very low levels of immature grain (e.g., detection of LEAP1 transcripts); b) the presence of mature grain (e.g., detection of DIP1 transcripts); and 3) estimate the average maturity of the grain in the batch, based on the relative transcript levels for all three genes.

The experiments presented above all use high quality RNA extracted from grain stored at −80° C. since harvesting. However, commercial green coffee grain used for roasting and extraction has previously been subjected to various post-harvest treatments, including extensive drying prior to storage (around 11-12% humidity). One would expect these treatments, as well as long-term storage under sub-optimum conditions of temperature and humidity, to dramatically affect the condition of the biological material, including RNA, contained within the grain.

As RNA is particularly sensitive to degradation, it could be anticipated that, a) little or no RNA could be isolated from the stored green grain, b) the RNA isolated would be non-functional (i.e., not suitable for cDNA synthesis), or 3) the RNA obtained would be too degraded to be used for transcript level measurements. These questions have not been previously addressed for coffee, or to our knowledge, for other stored grain, such as rice or corn, to any large extent. In order to address the first question of the RNA status in stored grain, we first extracted RNA from 4 separate samples of a single lot of green coffee that had been produced on an experimental farm in Ecuador. This lot was prepared using the dry process post-harvest treatment at the farm and the dried grain was shipped to the laboratory, where it was stored under ambient conditions for over 1 year. The gel analysis of the four RNA samples is presented in FIG. 21, and indicates that while high-quality RNA was not generated in this experiment, significant amounts of partially degraded RNA can be isolated. The fact that some of the main ribosomal RNA is still intact, suggests that a substantial amount of the degraded RNA molecules isolated are probably cut at fewer that 3-4 sites. Considering the limited damage of the RNA, it can be expected this RNA will be functional in a cDNA synthesis reaction.

To confirm our unexpected observation that only partially-degraded RNA can be isolated from stored, post-harvest processed green coffee grain, we carried out a second RNA extract on samples from 6 other batches of green robusta coffee that were stored for over one year. The results obtained are presented in FIG. 22. The results indicate that partially-degraded RNA can be isolated from the majority of the samples tested, with only sample FRT 28 producing little or no RNA. It is noted that on some occasions we have also been able to isolate even higher-quality RNA from stored grain (see FIG. 23). The source of the quality variability of the RNA isolated is currently unknown, although differences in the storage conditions, and possibly small unidentified variables in the RNA extraction procedure, are suspected. Future studies could investigate this possibility, in particular by looking at the effects of significant fluctuations of the humidity and temperature on the quality of extracted RNA and small adjustments to the RNA purification procedure.

To determine whether transcript quantification could be carried out using partially degraded RNA such as that seen in FIGS. 21 and 22, cDNA was made from several of these RNA samples using poly dT as primer. This cDNA was then used in a quantitative RT-PCR (QRT-PCR) analysis of the OLEO1 and DIP1 transcript levels. For comparative purposes, QRT-PCR analysis for these two genes was also carried out using cDNA prepared from high quality RNA from robusta variety BP358 at two late stages of grain development (42 weeks and the fully mature grain at 46 weeks).

The results obtained (FIG. 24) show that the control BP358 samples exhibit the expected results, that is, a high level of DIP1 transcripts and a medium levels of OLEO1 transcripts in the mature 46-week samples versus a high level of OLEO1 transcripts and a low level of DIP1 transcripts in the less mature 42-week grain, (FIG. 24). The data for the three stored samples, which were made using only mature grain (FRT 09, FRT 49, FRT 53), showed that a) the OLEO1 and DIP1 transcripts can easily be detected from partially-degraded RNA, and b) the ratio of OLEO1 versus DIP1 transcripts was that expected for these mature grain samples. It is important to point out that these grain samples were produced on an experimental farm using hand picking to ensure only mature red grain are harvested. It is noted that the RQ values obtained using samples with partially-degraded RNA were 3.9-5.5 fold lower for the OLEO1 transcripts and 3.9-2.2 fold lower for DIP1 transcripts than the equivalent RQ values of the 46-week BP 358 sample which had intact RNA. This reduction is presumably due to the reduction of polyA+ transcripts containing the regions with the TaqMan probe sequences (see FIGS. 25-28 for the position of the TaqMan primers and probe for each gene discussed here). Nonetheless, we also note that, despite the fall in the level of transcripts, the ratio of the OLEO1 versus DIP1 RQ values from the intact 46 week RNA (ratio=1.17) remains roughly equivalent to the ratios seen for the three degraded RNA samples (ratio's of 0.47, 0.91, and 1.14, respectively for the samples FRT 09, FRT 49, FRT 53). This latter observation strongly suggests that the transcripts of OLEO1, DIP1 and RPL39 degrade similarly during storage, and/or they are degraded similarly during the isolation procedure.

In the specification, there have been disclosed typical preferred embodiments of the invention and, although specific terms are employed, they are used in a generic and descriptive sense only and not for purposes of limitation, the scope of the invention being set forth in the claims. Obviously many modifications and variations of the invention are possible in light of the above teachings. It is therefore to be understood that within the scope of the appended claims the invention may be practiced otherwise than as specifically described.

REFERENCE LIST

Altschul, S. F., Madden, T. L., Schaffer, A. A., Zhang, J., Zhang, Z., Miller, W., and Lipman, D. J. (1997) Gapped BLAST and PSI-BLAST: a new generation of protein database search programs. *Nucl. Acids Res.* 25:3389-3402.

Choudhury, A., Roy, C., and Sengupta, D. Transgenic tobacco plants over expressing the heterologous mlea gene Rab16A from rice during high salt and water deficit display enhanced tolerance to salinity stress. *Plant Cell Reports.* 2007. (In Press)

De Castro, R. D. and Marraccini, P. (2006) Cytology, biochemistry and molecular changes during coffee fruit development. *Braz. J. Plant Physiol.,* 18:175-199.

Fait, A., Angelovici, R., Less, H., Ohad, I., Urbanczyk-Wochniak, E., Fernie, A. R., and Galili, G. (2006) *Arabidopsis* seed development and germination is associated with temporally distinct metabolic switches. *Plant Physiol* 142: 839-854.

Farah, A. and Donangelo, C. M. (2006) Phenolic compounds in coffee. *Braz. J. Plant Physiol.* 18:23-36.

Geromel, C., Ferreira, L. P., Guerreiro, S. M. C., Cavalari, A. A., Pot, D., Ferreira, L. F. P., Leroy, T., Vieira, L. G. E., Mazzafera, P., and Marraccini, P. (2006) Biochemical and genomic analysis of sucrose metabolism during coffee (*Coffea arabica*) fruit development. *J. Exp. Botany:* 1-16.

Girke, T., Todd, J., Ruuska, S., White, J., Benning, C., and Ohlrogge, J. (2000) Microarray analysis of developing *Arabidopsis* seeds. *Plant Physiol* 124:1570-1581.

Hajduch, M., Ganapathy, A., Stein, J. W., and Thelen, J. J. (2005) A systematic proteomic study of seed filling in soybean. Establishment of high-resolution two-dimensional reference maps, expression profiles, and an interactive proteome database. *Plant Physiol* 137:1397-1419.

Hattori, J., Boutilier, K. A., van Lookeren Campagne, M. M., and Mild, B. L. (1998) A conserved BURP domain defines a novel group of plant proteins with unusual primary structures. *Mol. Gen. Genet.* 259:424-428.

Hinniger, C., Caillet, V., Michoux, F., Ben Amor, M., Tanksley, S., Lin, C., and McCarthy, J. (2006) Isolation and characterization of cDNA encoding three dehydrins expressed during *Coffea canephora* (Robusta) grain development. *Ann. Bot. (Lond)* 97:755-765.

Hu, X. and Reddy, A. S. (1997) Cloning and expression of a PR5-like protein from *Arabidopsis*: inhibition of fungal growth by bacterially expressed protein. *Plant Mol. Biol.* 34:949-959.

Jalink, H. (1997) A method for determining the maturity and quality of seeds and an apparatus for sorting seeds. PCT Patent Application Publication No. WO/1997/042489 [PCT/NL1997/000230].

Lepelley, M., Cheminade, G., Tremillon, N., Simkin, A. J., Caillet, V., and McCarthy, J. (2007) Chlorogenic acid synthesis in coffee: An analysis of CGA content and real-time RT-PCR expression of HCT, HQT, C3H1, and CCoAOMT1 genes during grain development in *C. canephora*. *Plant Science Vol #:* 978-996.

Marraccini, P and Rogers J. Coffee storage proteins. (2003) U.S. Pat. No. 6,617,433.

Marraccini, P. and Rogers J. (2006) Leaf specific gene promoter of coffee. U.S. Pat. No. 7,153,953.

Murashige, T., a. S. F. (1962) A revised medium for rapid growth and bioassays with tobacco tissue cultures. *Physiol Plant* 15:473-497.

Privat, I., McCarthy, J., Pétiard, V., Lin, C., and Tanksley, S., (2006) Nucleic acids and proteins associated with sucrose accumulation in coffee. PCT Patent Publication No. WO/2007/022318

Sanger, F., Nicklen, S., and Coulson, A. R. (1992) DNA sequencing with chain-terminating inhibitors. 1977. *Biotechnology* 24:104-108.

Simkin, A. J., McCarthy, J., Petiard, V., Tanksley, S., and Lin, C. (2006a) Oleosin genes and promoter from coffee. United States Patent Application No. US2006/026121, PCT Patent Publication No. WO 2007/005928 A2.

Simkin, A. J., Qian, T., Caillet, V., Michoux, F., Ben, A. M., Lin, C., Tanksley, S., and McCarthy, J. (2006b) Oleosin gene family of *Coffea canephora*: quantitative expression analysis of five oleosin genes in developing and germinating coffee grain. *J Plant Physiol* 163:691-708.

Soeda, Y., Konings, M. C., Vorst, O., van Houwelingen, A. M., Stoopen, G. M., Maliepaard, C. A., Kodde, J., Bino, R. J., Groot, S. P., and van der Geest, A. H. (2005) Gene expression programs during *Brassica oleracea* seed maturation, osmopriming, and germination are indicators of progression of the germination process and the stress tolerance level. *Plant Physiol* 137:354-368.

Tanksley, S., Lin, C., Ben Amor, M., McCarthy, J., and Pétiard, V. (2007) Dehydrin genes and promoter from coffee. United States Patent Application No. US2006/026234; PCT Patent Publication No. WO 2007/005980.

Van Son Le. (2005) The BURP domain protein family of *Arabidopsis*: a novel component related to seed development. [IPK-Gatersleben, Germany. PhD thesis.].

Vigers, A. J., Roberts, W. K., and Selitrennikoff, C. P. (1991) A new family of plant antifungal proteins. *Mol. Plant Microbe Interact.* 4:315-323.

Yamaguchi-Shinozaki K., a. S. K. (1993) The plant hormone abscisic acid mediates the drought-induced expression but not the seed-specific expression of rd22, a gene responsive to dehydration stress in *Arabidopsis thaliana*. *Mol. Gen. Genet.* 238:17-25.

Yamaguchi-Shinozaki, K. and Shinozaki, K. (2006) Transcriptional regulatory networks in cellular responses and tolerance to dehydration and cold stresses. *Ann. Rev. Plant Biol.* 57:781-803.

What is claimed is:

1. A nucleic acid construct comprising a heterologous region, wherein the heterologous region comprises a nucleic acid molecule having a coding sequence that encodes a protein comprising the amino acid sequence that is SEQ ID NO:8 or 9.

2. The nucleic acid construct according to claim 1, which is a gene having an open reading frame that comprises the coding sequence.

3. A vector comprising:
   a nucleic acid construct comprising a heterologous region, wherein the heterologous region comprises a nucleic acid molecule having a coding sequence that encodes a protein comprising the amino acid sequence that is SEQ ID NO:8 or 9,
   wherein the vector comprises at least one coding sequence operably-linked to a promoter.

4. A cell transformed with a nucleic acid molecule that encodes a protein comprising the amino acid sequence that is SEQ ID NO:8 or 9.

5. The transformed cell of claim 4, which is a plant cell.

6. The nucleic acid construct according to claim 1, wherein the protein comprises the amino acid sequence that is SEQ ID NO: 8.

7. The nucleic acid construct according to claim 1, wherein the protein comprises the amino acid sequence that is SEQ ID NO: 9.

\* \* \* \* \*